(12) United States Patent
Christensen et al.

(10) Patent No.: US 9,994,850 B2
(45) Date of Patent: *Jun. 12, 2018

(54) ANTISENSE DESIGN

(71) Applicant: Roche Innovation Center Copenhagen A/S, Basel (CH)

(72) Inventors: Signe M. Christensen, Copenhagen (DK); Nikolaj Dam Mikkelsen, Bronshoj (DK); Miriam Frieden, Copenhagen (DK); Henrik Frydenlund Hansen, Ringsted (DK); Troels Koch, Copenhagen S (DK); Daniel Sejer Pedersen, Valby (DK); Christoph Rosenbohm, Birkerod (DK); Charlotte Albaek Thrue, Hampshire (GB); Majken Westergaard, Birkerod (DK)

(73) Assignee: Roche Innovation Center Copenhagen A/S, Basel (CH)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/619,134

(22) Filed: Jun. 9, 2017

(65) Prior Publication Data

US 2017/0342413 A1 Nov. 30, 2017

Related U.S. Application Data

(63) Continuation of application No. 15/237,307, filed on Aug. 15, 2016, now Pat. No. 9,708,614, which is a continuation of application No. 13/797,913, filed on Mar. 12, 2013, now Pat. No. 9,428,534, which is a continuation of application No. 10/535,472, filed as application No. PCT/DK03/00788 on Nov. 18, 2003, now Pat. No. 9,045,518.

(30) Foreign Application Priority Data

Nov. 18, 2002 (DK) ................................ 2002 01774
Oct. 20, 2003 (DK) ................................ 2003 01540

(51) Int. Cl.
| A61K 31/712 | (2006.01) |
| A61K 48/00 | (2006.01) |
| C12N 15/113 | (2010.01) |
| A61K 31/7088 | (2006.01) |
| C07H 21/00 | (2006.01) |
| C12N 15/11 | (2006.01) |
| C07H 19/04 | (2006.01) |
| C07H 19/06 | (2006.01) |
| C07H 19/16 | (2006.01) |
| C07H 21/02 | (2006.01) |
| C07H 21/04 | (2006.01) |

(52) U.S. Cl.
CPC ........ *C12N 15/113* (2013.01); *A61K 31/7088* (2013.01); *C07H 19/04* (2013.01); *C07H 19/06* (2013.01); *C07H 19/16* (2013.01);

*C07H 21/00* (2013.01); *C07H 21/02* (2013.01); *C07H 21/04* (2013.01); *C12N 15/111* (2013.01); *C12N 15/1137* (2013.01); *C12N 2310/11* (2013.01); *C12N 2310/315* (2013.01); *C12N 2310/3231* (2013.01); *C12N 2310/341* (2013.01); *C12N 2310/344* (2013.01); *C12N 2320/30* (2013.01); *C12N 2320/51* (2013.01)

(58) Field of Classification Search
USPC .......... 435/6.1, 6.11, 91.1, 91.31, 455, 458; 514/44, 1.2, 19.3; 536/23.1, 24.5, 22.1, 536/27.6, 27.81, 28.5, 28.54
See application file for complete search history.

(56) References Cited

U.S. PATENT DOCUMENTS

| 5,623,065 | A | 4/1997 | Cook et al. |
| 5,801,154 | A | 9/1998 | Baracchini et al. |
| 5,955,589 | A | 9/1999 | Cook et al. |
| 6,884,787 | B2 * | 4/2005 | Monia ................ C12N 15/1136 435/325 |
| 7,399,845 | B2 | 7/2008 | Seth et al. |
| 7,589,190 | B2 | 9/2009 | Westergard et al. |
| 7,622,453 | B2 | 11/2009 | Frieden et al. |
| 7,687,617 | B2 | 3/2010 | Thrue et al. |
| 7,713,738 | B2 | 5/2010 | Hansen et al. |
| 7,737,264 | B2 | 6/2010 | Thrue et al. |
| 7,741,457 | B2 | 6/2010 | Seth et al. |
| 8,022,193 | B2 | 9/2011 | Seth et al. |
| 8,026,355 | B2 | 9/2011 | Hansen et al. |

(Continued)

FOREIGN PATENT DOCUMENTS

| EP | 0618925 | 10/1994 |
| EP | 1152009 | 11/2001 |

(Continued)

OTHER PUBLICATIONS

U.S. Appl. No. 14/656,610, filed Mar. 12, 2015, Christensen et al.
U.S. Appl. No. 15/527,765, filed May 18, 2017, Frydenlund Hansen.
U.S. Appl. No. 15/618,650, filed Jun. 9, 2017, Christensen et al.
U.S. Appl. No. 15/618,892, filed Jun. 9, 2017, Christensen et al.
Braasch et al., "Locked nucleic acid (LNA): fine-tuning the recognition of DNA and RNA," Chem. & Bio., 55: 1-7 (2000).
Kvaerno et al., Antisense molecules and furanose conformations— is it really that simple? 2001, Chemical Communications, pp. 1419-1424.
Third Party Observation for European Application No. 14163184.6, dated May 9, 2017, 3 pages.
Third Party Observation for European Application No. 14163184.6, dated Jan. 26, 2017, 8 pages.

(Continued)

Primary Examiner — Jane Zara
(74) Attorney, Agent, or Firm — Fish & Richardson P.C.

(57) ABSTRACT

A novel class of pharmaceuticals which comprises a Locked Nucleic Acid (LNA) which can be used in antisense therapy. These novel oligonucleotides have improved antisense properties. The novel oligonucleotides are composed of at least one LNA selected from beta-D-thio/amino-LNA or alpha-L-oxy/thio/amino-LNA. The oligonucleotides comprising LNA may also include DNA and/or RNA nucleotides.

19 Claims, 25 Drawing Sheets

(56) References Cited

U.S. PATENT DOCUMENTS

| | | | |
|---|---|---|---|
| 8,470,791 | B2 | 6/2013 | Hansen et al. |
| 8,785,617 | B2 | 7/2014 | Thrue et al. |
| 9,045,518 | B2* | 6/2015 | Christensen ....... A61K 31/7088 |
| 9,428,534 | B2* | 8/2016 | Christensen ....... A61K 31/7088 |
| 9,708,614 | B2* | 7/2017 | Christensen ....... A61K 31/7088 |
| 2003/0087853 | A1 | 5/2003 | Crooke |
| 2003/0125241 | A1 | 7/2003 | Wissenbach et al. |
| 2003/0215943 | A1 | 11/2003 | Crooke et al. |
| 2006/0128646 | A1 | 6/2006 | Christensen et al. |
| 2014/0128586 | A1 | 5/2014 | Christensen et al. |
| 2014/0128591 | A1 | 5/2014 | Christensen et al. |
| 2014/0194614 | A1 | 7/2014 | Christensen et al. |
| 2014/0288290 | A1 | 9/2014 | Christensen et al. |
| 2014/0296502 | A1 | 10/2014 | Christensen et al. |
| 2015/0275212 | A1 | 10/2015 | Albaek et al. |
| 2015/0368642 | A1 | 12/2015 | Albaek et al. |
| 2016/0168575 | A1 | 6/2016 | Christensen et al. |
| 2016/0168576 | A1 | 6/2016 | Christensen et al. |
| 2016/0289677 | A1 | 10/2016 | Albaek et al. |
| 2016/0348111 | A1 | 12/2016 | Christensen et al. |

FOREIGN PATENT DOCUMENTS

| | | |
|---|---|---|
| EP | 1222309 | 7/2002 |
| EP | 1251183 | 10/2002 |
| WO | WO 98/39352 | 9/1998 |
| WO | WO 99/14226 | 3/1999 |
| WO | WO 2000/056748 | 9/2000 |
| WO | WO 00/66604 | 11/2000 |
| WO | WO 2001/007457 | 2/2001 |
| WO | WO 01/25248 | 4/2001 |
| WO | WO 01/25478 | 4/2001 |
| WO | WO 01/48190 | 7/2001 |
| WO | WO 2002/028875 | 4/2002 |
| WO | WO 2002/094250 | 11/2002 |
| WO | WO 2003/011887 | 2/2003 |
| WO | WO 2003/085110 | 10/2003 |
| WO | WO 2003/095467 | 11/2003 |
| WO | WO 2004/044181 | 5/2004 |
| WO | WO 2004/063329 | 7/2004 |
| WO | WO 2004/069991 | 8/2004 |

OTHER PUBLICATIONS

Third-Party Submission Under 37 CFR 1.290 for U.S. Appl. No. 13/797,919, dated Sep. 24, 2014, 11 pages.
Third-Party Submission Under 37 CFR 1.290 for U.S. Appl. No. 13/797,919, dated Dec. 23, 2014, 15 pages.
Third-Party Submission Under 37 CFR 1.290 for U.S. Appl. No. 13/841,646, dated Jul. 28, 2014, 12 pages.
Third-Party Submission Under 37 CFR 1.290 for U.S. Appl. No. 13/841,646, dated Dec. 17, 2014, 14 pages.
Third-Party Submission Under 37 CFR 1.290 for U.S. Appl. No. 13/797,913, dated Mar. 25, 2015, 13 pages.
Third-Party Submission Under 37 CFR 1.290 for U.S. Appl. No. 13/797,913, dated Dec. 23, 2014, 12 pages.
Third-Party Submission Under 37 CFR 1.290 for U.S. Appl. No. 13/797,913, dated Oct. 14, 2014, 18 pages.
Third-Party Submission Under 37 CFR 1.290 for U.S. Appl. No. 13/797,913, dated Oct. 14, 2014, 21 pages.
Third-Party Submission Under 37 CFR 1.290 for U.S. Appl. No. 15/237,307, dated Apr. 5, 2017, 6 pages.
Third-Party Submission Under 37 CFR 1.290 for U.S. Appl. No. 15/237,307, dated May 1, 2017, 4 pages.
"Declaration of Christoph Rosenbohm," Exhibit D12 in Opposition Proceedings for European Application No. 14163184.6, dated Oct. 21, 2016, 9 pages.
"Declaration of Eric Swayze," Exhibit D11 in Opposition Proceedings for European Application No. 07762892.3, dated Feb. 14, 2012, 6 pages.
Arzumanov et al., "Inhibition of HIV-1 Tat-Dependent Trans Activation by Steric Block Chimeric 2'-O Methyl/LNA Oligoribonucleotides," Biochemistry 40:14645-1465 (2001).

Bennett et al., "Antisense oligonucleotides as a tool for gene functionalization and target validation," Biochim. Biophys. Acta, 1489:19-30 (1999).
Bolli et al., "Bicyclo/DNA: a Hoogsteen/selectice pairing system", Chemistry & Biology, 3(3):197/206 (1996).
Braasch et al., "Implications of High-Affinity Hybridization by Locked Nucleic Acid Oligomers for Inhibition of Human Telomerase," Biochemistry, 41(14):4503-4510 (2002).
Braasch et al., "Locked nucleic acid (LNA): fine-tuning the recognition of DNA and RNA," Chem. & Bio., 55:1-7 (2001).
Branch, "A good antisense molecule is hard to find", TIBS 23, Feb. 1998 (1998).
Childs et al., "Oligonucleotide directed misfolding of RNA inhibits Candida albicans group I intron splicing," PNAS, 99(17):11091-11096 (2002).
Christensen, et al., "A novel class of oligonucleotides analogues containing . . . ," J. Am chem Society, 120:5458-5463 (1998).
Cook, "Making drugs out of oligonucleotides: a brief review and perspective," Nucleosides & Nucleotides, 18(6&7), 1141-62 (1999).
Cook, "Medicinal Chemistry of Antisense Oligonucleotides", in Antisense Drug Technology, Marcel Dekker Inc. (2001).
Crinelli et al., "Design and characterization of decoy oligonucleotides containing locked nucleic acids," Nucl. Acid Res., 30(11):2435-2443 (2002).
Crooke, "Antisense Therapeutics," Biotechnol. Genet. Eng. Rev., 15:121-57 (1998).
Cummins et al., "Characterization of fully 2'-modified oligoribonucleotide hetero- and homoduplex hybridization and nuclease sensitivity," Nucleic Acids Research, Jun. 1995, 23(11):2019-2024.
Dean et al., "Pharmacology of 2'/O/(2/Methoxy)ethyl/Modified Antisense Oligonucleotides", in Antisense Drug Technology, Marcel Dekker Inc. (2001).
Elayadi et al., "Implications of High-Affinity Hybridization by Locked Nucleic Acid Oligomers for Inhibition of Human Telomerase," Biochemistry, 41:9973-9981 (2002).
Elmén et al., "Locked nucleic acid containing antisense oligonucleotides enhance inhibition of HIV/1 genome dimerization and inhibit virus replication", FEBS Lettters, 578:285/290 (2004).
Examination Report in corresponding Australian Application No. 2013201763, dated Oct. 1, 2014, pp. 1-4.
Fakler et al., "Short Antisense Oligonucleotide/mediated Inhibition Is Strongly Dependent on Oligo Length and Concentration but Almost Independent of Location of the Target Sequence", The Journal of Biological Chemistry, 269(23):16187/16194 (1994).
Flanagan et al., "Effects of oligonucleotide length, mismatches and mRNA levels on C/5 propyne/modified antisense potency", Nucleic Acids Research, 24(15):2936/2941 (1996).
Fluiter et al., "In vivo tumor growth inhibition and biodistribution studies of locked nucleic acid (LNA) antisense oligonucleotides", Nucleic Acids Research, 31(3):953/962 (2003).
Freier et al., "The ups and downs of nucleic acid duplex stability: structure-stability studies on chemically-modified DNA:RNA duplexes," Nucl. Acid Res., 25(22):4429-4443 (1997).
Frieden et al., "Nuclease Stability of LNA oligonucleotides and LNA/DNA chimeras", Poster presented at the IRT2002, Sep. 10/14, 2002; Leuven, Belgium (2002).
Grünweller et al., "Comparison of different antisense strategies in mammalian cells using locked nucleic acids, 2'/O/methyl RNA, hosphorothioates and small interfering RNA", Nucleic Acids Research, 31(12):3185/3193 (2003).
Hakansson et al., "The Adenine Derivative of x-1-LNA (a-L-ribo Configured Locked Nucleic Acid): Synthesis and High-Affinity," Bioorg Med. Chem Lett, 11:935-938 (2001).
Hansen et al., "Antisense Knockdown of PKC/α Using LNA/ Oligos", Nucleosides, Nucleotides & Nucleic Acids, 22(5/8):1607/ 1609 (2003).
Hari et al., Nucleic Acids Research Supplement, No. 2, 147/148 (2002).
Herdewijn, "Targeting RNA with Conformationally Restricted Oligonucleotides", Liebigs Annalen, 1996(9):1337/1348 (1996).

(56) References Cited

OTHER PUBLICATIONS

Imanishi et al., poster P01/101 for Sixteenth International Congress of Heterocyclic Chemistry. Aug. 10/15, 1997.
Jacobsen et al., "LNA-enhanced detection of single nucleotide polymorphisms in the apolipoprotein E," Nucl. Acid Res., 30(19), in press (2002).
Jen et al. (2000) Stem Cells 18:307-319.
Khatsenko et al., "Absorption of Antisense Oligonucleotides in Rat Intestine: Effect of Chemistry and Length", Antisense & Nucleic Acid Drug Development, 10:35/44 (2000).
Koshkin et al., "LNA (Locked Nucleic Acids): Synthesis of the Adenine, Cytosine, Guanine, 5/Methylcytosine, Thymine and Uracil Bicyclonucleoside Monomers, Oligomerisation, and Unprecedented Nucleic Acid Recognition", Tetrahedron, 54:3607/3630 (1998).
Koshkin et al., "Novel Convenient Syntheses of LNA [2.2.1]Bicycle Nueleosides", Tetrahedron Letters, 39:4381/4384 (1998).
Koshkin et al., "Synthesis of Novel 2',3'-Linked Bicyclic Thymine Ribonucleotides," J. Org. Chem., 63(8):2778-2781 (1998).
Koshkin et al., "The First Analogues of LNA (Locked Nucleic Acids): Phosphorothioate-LNA 2'—THIO-LNA," J. Am Chem. Soc., 120(50): 13252-13253.
Kumar et al., "Design and characterization of decoy oligonucleotides containing locked nucleic acids," Bioorg & Med. Chem. Lett., 8:2219-2222 (1998).
Kurreck et al., "Design of antisense oligonucleotides stabilized by locked nucleic acids," Nucl. Acid Res. 30(9), 1911-1918 (2002).
L. Kienicke et al., "alpha-L-RNA (alpha-L-ribo Configured RNA): Synthesis and RNA-Selective Hybridization of alpha-L-RNA/alpha-L-LNA Chimera," Bioorganic & Medicinal Chemistry Letters, vol. 12, 4, 2002 pp. 593-596.
M. Frieden et al., "Expanding the design horizon of antisense oligonucleotides with alpha-L-LNA," Nucleic Acids Research, vol. 31, No. 21, 2003, pp. 6365-6372.
Morita et al., "2'/O,4'/C/Ethylene/Bridged Nucleic Acids (ENA) as Effective Antisense Oligonucleotides", Bioorganic & Medical Chemistry, 11: 2211/2226 (2003).
Morita et al., "2'/O,4'/C/Ethylene/Bridged Nucleic Acids (ENA): Highly Nuclease/Resistant and Thermodynamically Stable Oligonucleotides for Antisense Drug", Bioorganic & Medical Chemistry Letters, 12:73/76 (2002).
Neilsen et al., "Synthesis of 2'-0,3'-C linked bicyclic nuclesides and bicyclic oligonucleotides" J. Chem. Soc., Perkin Trans. 1, pp. 3423-3433 (1997).
Nielsen et al., "NMR structure of an cx,-L-LNA:RNA hybrid: structural implications for RNase H recognition," Nucleic Acids Research, Oct. 2003, 31(20):5858-5867, DOI: 10.1093/nar/gkg800.
Nielsen et al., "NMR Studies of Fully Modified Locked Nucleic Acid (LNA) Hybrids: Solution Structure of an LNA:RNA Hybrid and Characterization of an LNA:DNA Hybrid," Bioconjug Chem., May-Jun. 2004;15(3):449-457.
Nielsen et al., "A novel class of conformationally restricted oligonucleotide analogues: synthesis of 2', 3'-bridged monomers and RNA-selective hybridasation," Chem. Commun., 9:825-826 (1997).
Nielsen et al., "α/L/LNA (α/L/ribo Configured Locked Nucleic Acid) Recognition of DNA: An NMR Spectroscopic Study", Chemistry—A European Journal, 8(13):3001/3009 (2002).
Obika et al., "2'-O,4'-C-Methylened Bridged . . . " Bioorg & Med. Chem., 9:1001-1011 (2001).
Obika et al., "Stabili'/O,4'C/methyleneribonucleosides", Tetrahedron Letters, 39:5401/5404 (1998).
Obika et al., "Synthesis of 2'/O,4'/C/Methyleneuridine and /cytidine. Novel Bicyclic Nucleosides Having a Fixed C3, /endo Sugar Puckering", Tetrahedron Letters, 38(50):8735/8738 (1997).
Pallan et al., "Structure and nuclease resistance of 2',4'-constrained 2'-0-methoxyethyl(cMOE) and 2'-0-ethyl (cEt) modified DNAs," Chem Commun (Camb), Aug. 25, 2012;48(66):8195-7. doi: 10.1039/c2cc32286b. Epub May 22, 2012.
Petersen et al., "a-1-LNA . . . ," J. Am. Chem. Soc., 123"7431-7432 (2001).
Petersen et al., "LNA: a versatile tool for therapeutics and genomics", Trends in Biotechnology, 21(2):74/81 (2003).
Rajwanshi et al., High-affinity nucleic acid recognition using 'LNA'. . . J. Chem. Commun, pp. 2073-2074 (1999).
Rajwanshi et al., "LNA stereoisomers: xylo-LNA . . . ," Chem. Commun., pp. 1395-1396 (1999).
Rajwanshi et al., "Synthesis and restricted furanose conformations of three novel bicyclic thymine nucleosides: a xylo/LNA nucleoside, a 3'/O,5'/C/methylene/linked nucleoside, and a 2'/O,5'C/methylene/linked nucleoside", Journal of the Chemical Society, Perkin Transactions I, pp. 1407/1414 (1999).
Rajwanshi et al., "The Eight Stereoisomers of LNA (Locked Nucleic Acid): A Remarkable Family of Strong RNA Binding Molecules," Angew Chem. Int. Ed., 39(9):1656-1659 (2000).
Sec. 715.05, Manual of Patent Examining Procedure, Nov. 2015 revision, US Patent and Trademark Office, 2 pages.
Simeonov et al., "Single nucleotide polymorphism genotyping using short, flourescently labeled locked . . . " Nucleic Acids Research, 30(17), in press (2002).
Singh et al., "LNA (locked nucleic acids): synthesis and high/ affinity nucleic acid recognition", Chemical Communications, pp. 455/456 (1998).
Singh et al., "Synthesis of 2'-Amino-LNA: A Novel Conformationally Restricted High-Affinity Oligonucleotide Analogue with a Handle," J. Org. Chem. 63:10035-10039 (1998).
Singh et al., "Universality of LNA/mediated high/affinity nucleic acid recognition", Chemical Communications, 12:1247/1248 (1998).
Singh, "Synthesis of Novel Bicyclo . . . ," J. Org. Chem. 63:6078-6079 (1998).
Sorensen et al., "a-L-ribo-Configured Locked Nucleic Acid (a-L-LNA):Synthesis and Properties," J. Am Chem. Soc., 124(10):2164-2176 (2002).
Third Party Observation for European Application No. 13791808.2, submitted Apr. 4, 2016, 7 pages.
Third Party Observation for European Application No. 14163184.6, submitted Feb. 1, 2017, 8 pages.
Third Party Observation for European Application No. 14163184.6, submitted May 11, 2015, 4 pages.
Third Party Observation for European Application No. 14163184.6, submitted Jan. 12, 2016, 7 pages.
Third Party Observation for European Application No. 14163184.6, submitted Dec. 23, 2014, 4 pages.
Third Party Observation for European Application No. 14163184.6, submitted Nov. 25, 2016, 10 pages.
Vester et al., "Chemically modified oligonucleotides with efficient RNase H response" J. Bioorg. Med. Chem. Lett. 18:2296-2300, 2008.
Vester et al., "LNAzymes: Incorporation of LNA-Type Monomers into DNAzymes Markedly Increases RNA Cleavage," J. Am Chem. Soc., 124(46)L13682-13683.
Wagner et al., "Potent and selective inhibition of gene expression by an antisense heptanucleotide", Nature Biotechnology, 14(7):840/844 (1996).
Wahlestedt et al., "Potent and nontoxic antisense oligonucleotides containing locked nucleic acids," PNAS, 97 (10):5633-5638 (2000).
Wengel et al., "LNA (Locked Nucleic Acid) and the Diastrereoisomeric . . . ," Nucleotides & Nucleic Acids, 20(4-7):389-396 (2001).
Wengel, "LNA (Locked Nucleic Acids): Synthesis and high/affinity nucleic acid recognition—Stop the twisting!", National seminar on Perspectives in Interfacial Areas of Chemistry and Biology, Jan. 20/22, 1998.
Wengel, J., "LNA (Locked Nucleic Acid," In Antisense Drug Technology: Principles, pp. 339-355 (2001).
Westergaard et al., "in vivo Comparison of Cholesteryl Modified siRNA and LNA Antisense Downregulation of ApoB/100", Poster (2002).
Woolf et al., "The stability, toxicity and effectiveness of unmodified and phosphorthioate antisense oligodeoxynucleotides in Xenopus oocytes and embryos", Nucleic Acids Research 18(7):1763/1769 (1990).

(56) References Cited

OTHER PUBLICATIONS

Zamecnik et al., "Inhibition of Rous sarcoma virus replication and cell transformation," PNAS, 75(1):280-284 (1978).
Chen et al., "A Safety and Pharmacokinetic Study of a Mixed-Backbone Oligonucleotide (GEM231) Targeting the Type I Protein Kinase a by Two-hour Infusions in Patients with Refractory Solid Tumors," Clinical Cancer Research, Apr. 2000, 6(4):1259-1266.
Horie et al., "Hepatocyte-specific Pten deficiency results in steatohepatitis and hepatocellular carcinomas," J Clin Invest, Jun. 15, 2004, 113(12):1774-1783.
Levin et al., Antisense Drug Technology, 2001, chapter 9, pp. 201-268.
Monia et al.. "Evaluation of 2'-modified oligonucleotides containing 2'-deoxy gaps as antisense of gene expression," J Biol Chem, Jul. 5, 1993, 268(19):14514-14522.
Office Action dated Sep. 12, 2014, in U.S. Appl. No. 14/073,722, 13 pages.
Sewell et al., "Phase I trial of ISIS 104838, a 2'-methoxyethyl modified antisense oligonucleotide targeting tumor necrosis factor-alpha," J Pharmacol Exp Ther, Dec. 2002, 303(3):1334-1343.
Third-Party Submission Under 37 CFR 1.290 for U.S. Appl. No. 15/618,650, dated Oct. 2, 2017, 7 pages.

\* cited by examiner beta-D-oxy-LNA; 2740 alpha-L-oxy-LNA; 2774 beta-D-amino-LNA; 2752 beta-D-thio-LNA; 2746

| Lane | Input | Ha-Ras | 28S | | %Ha-Ras |
|---|---|---|---|---|---|
| 1 | mock | 1295 | 341598 | 0,003791 | 100 |
| 2 | 5nm 2754 | 579 | 314264 | 0,001842 | 37,33333 |
| 3 | 10nm 2754 | 191 | 264155 | 0,000723 | 14,65168 |
| 4 | 20nm 2754 | 149 | 346839 | 0,00043 | 8,705048 |
| 5 | 40nm 2754 | 142 | 358302 | 0,000396 | 8,030673 |
| 6 | 20nm2756 | 1082 | 389683 | 0,002777 | 56,26375 |
| 13 | mock | 2038 | 331165 | 0,006154 | 100 |
| 14 | 5nm 2742 | 386 | 276874 | 0,001394 | 28,24997 |
| 15 | 10nm 2742 | 250 | 259534 | 0,000963 | 19,51905 |
| 16 | 20nm 2742 | 182 | 369254 | 0,000493 | 9,987551 |
| 17 | 40nm 2742 | 227 | 392719 | 0,000578 | 11,71269 |
| 18 | 20nm 2744 | 1069 | 480037 | 0,002227 | 45,12486 |
| 19 | mock | 1534 | 466543 | 0,003288 | 100 |
| 20 | 5nm 2776 | 364 | 474676 | 0,000767 | 15,53878 |
| 21 | 10nm 2776 | 167 | 519707 | 0,000321 | 6,511346 |
| 22 | 20nm 2776 | 53 | 411881 | 0,000129 | 2,607456 |
| 23 | 40nm 2776 | 105 | 375591 | 0,00028 | 5,684831 |
| 24 | 20nm 2778 | 703 | 184089 | 0,003819 | 77,38207 |

FIG. 6

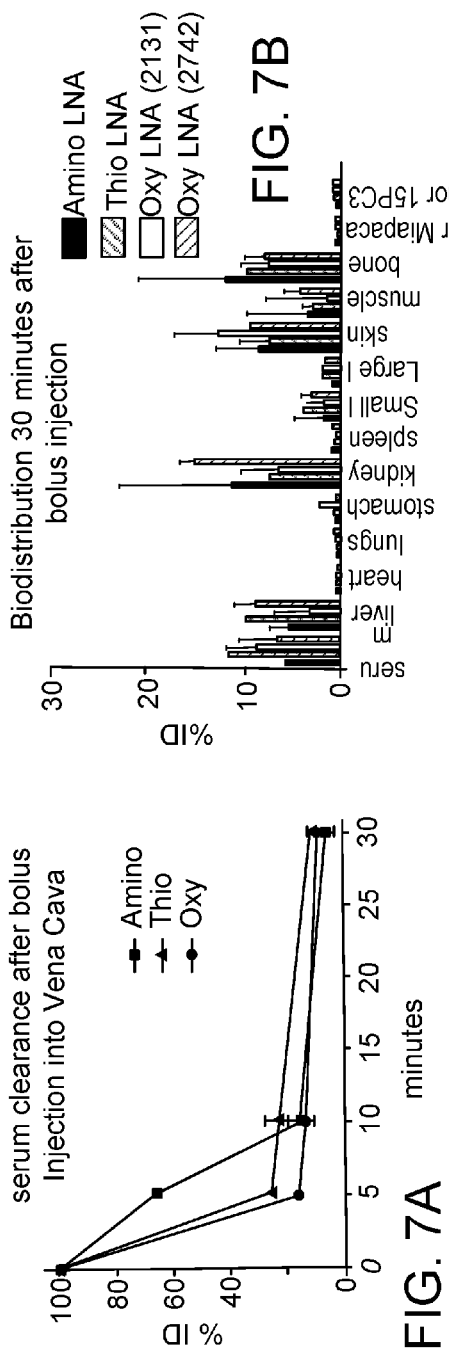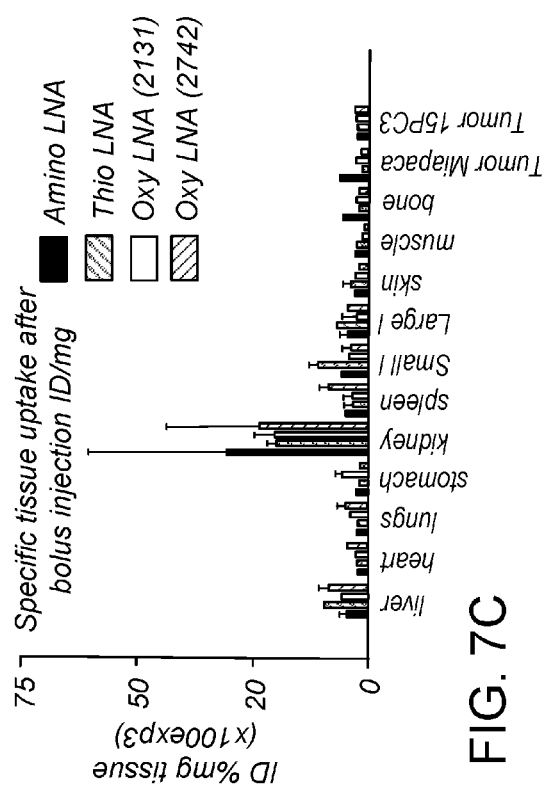
FIG. 7A
FIG. 7B
FIG. 7C

1. DNA/PO
2. oxy-LNA
   PS-gap/PO-flanks
3. thio-LNA
   all-PO
4. thio-LNA
   PS-gap/PO-flanks
5. DNA/PS

| | | |
|---|---|---|
| Group 1 | saline | |
| Group 2 | 2.5 mg | 2742 |
| Group 3 | 1 mg | 2742 |
| Group 4 | 2.5 mg | 2744 |
| Group 5 | 1 mg | 2744 |
| Group 6 | 2.5 mg | 2776 |
| Group 7 | 1 mg | 2776 |
| Group 8 | 2.5 mg | 2778 |
| Group 9 | 1 mg | 2778 |
| Group 10 | 5 mg | 2713 |
| Group 11 | 5 mg | 2722 | ically derivatised. Thus, the

SEQUENCE LISTING

<160> NUMBER OF SEQ ID NOS: 33

<210> SEQ ID NO 1
<211> LENGTH: 16
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-amino-LNA
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: modified_base
<222> LOCATION: (13)..(15)
<223> OTHER INFORMATION: Beta-D-amino-LNA

<400> SEQUENCE: 1
tccgtcatcg ctcctc                                                   16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiolated bond
<220> FEATURE:
<221> NAME/KEY: modified_base
<222> LOCATION: (1)..(3)
<223> OTHER INFORMATION: Beta-D-amino-LNA
<220> FEATURE:
<221> NAME/KEY: misc_feature
<222> LOCATION: (2)..(3)
<223> OTHER INFORMATION: Thiolated bond
<220> FEATURE:
<221> NAME/KEY: misc_feature
<222> LOCATION: (3)..(4)
<223> OTHER INFORMATION: Thiolated bond
<220> FEATURE:
<221> NAME/KEY: misc_feature
<222> LOCATION: (4)..(5)
<223> OTHER INFORMATION: Thiolated bond
```

```
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (13)..(15)
<223> OTHER INFORMATION: Beta-D-amino-LNA
<220> FEATURE:
<221> NAME/KEY: misc_feature
<222> LOCATION: (14)..(15)
<223> OTHER INFORMATION: Thiolated bond
<220> FEATURE:
<221> NAME/KEY: misc_feature
<222> LOCATION: (15)..(16)
<223> OTHER INFORMATION: Thiolated bond

<400> SEQUENCE: 2
tccgtcatcg ctcctc                                                    16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiolated bond
<220> FEATURE:
<221> NAME/KEY: modified_base
<222> LOCATION: (1)..(3)
<223> OTHER INFORMATION: Beta-D-oxy-LNA
<220> FEATURE:
<221> NAME/KEY: misc_feature
<222> LOCATION: (2)..(3)
<223> OTHER INFORMATION: Thiolated bond
<220> FEATURE:
<221> NAME/KEY: misc_feature
<222> LOCATION: (3)..(4)
<223> OTHER INFORMATION: Thiolated bond
<220> FEATURE:
<221> NAME/KEY: misc_feature
```

```
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (13)..(15)
<223> OTHER INFORMATION: Beta-D-oxy-LNA
<220> FEATURE:
<221> NAME/KEY: misc_feature
<222> LOCATION: (14)..(15)
<223> OTHER INFORMATION: Thiolated bond
<220> FEATURE:
<221> NAME/KEY: misc_feature
<222> LOCATION: (15)..(16)
<223> OTHER INFORMATION: Thiolated bond

<400> SEQUENCE: 3
tccgtcatcg ctcctc                                                     16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: Beta-D-amino-LNA
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
```

```
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: modified_base
<222> LOCATION: (12)..(16)
<223> OTHER INFORMATION: Beta-D-oxy-LNA

<400> SEQUENCE: 4
ttttgtcatc gtcttt                                                       16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: Beta-D-oxy-LNA
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: modified_base
<222> LOCATION: (12)..(16)
<223> OTHER INFORMATION: Beta-D-oxy-LNA

<400> SEQUENCE: 5
ttttgtcatc gtcttt                                                       16

<210> SEQ ID NO 6
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-amino-LNA
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: modified_base
<222> LOCATION: (13)..(15)
<223> OTHER INFORMATION: Beta-D-amino-LNA

<400> SEQUENCE: 6
tccgtcatcg ctcctc                                                   16

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiolated bond
<220> FEATURE:
<221> NAME/KEY: modified_base
<222> LOCATION: (1)..(3)
<223> OTHER INFORMATION: Beta-D-amino-LNA
<220> FEATURE:
<221> NAME/KEY: misc_feature
<222> LOCATION: (2)..(3)
<223> OTHER INFORMATION: Thiolated bond
<220> FEATURE:
<221> NAME/KEY: misc_feature
<222> LOCATION: (3)..(4)
<223> OTHER INFORMATION: Thiolated bond
<220> FEATURE:
<221> NAME/KEY: misc_feature
<222> LOCATION: (4)..(5)
```

```
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (13)..(15)
<223> OTHER INFORMATION: Beta-D-amino-LNA
<220> FEATURE:
<221> NAME/KEY: misc_feature
<222> LOCATION: (14)..(15)
<223> OTHER INFORMATION: Thiolated bond
<220> FEATURE:
<221> NAME/KEY: misc_feature
<222> LOCATION: (15)..(16)
<223> OTHER INFORMATION: Thiolated bond

<400> SEQUENCE: 7
tccgtcatcg ctcctc                                                    16

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
```

```
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: modified_base
<222> LOCATION: (13)..(15)
<223> OTHER INFORMATION: Beta-D-oxy-LNA

<400> SEQUENCE: 8
tccgtcatcg ctcctc                                                     16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiolated bond
<220> FEATURE:
<221> NAME/KEY: modified_base
<222> LOCATION: (1)..(3)
<223> OTHER INFORMATION: Beta-D-oxy-LNA
<220> FEATURE:
<221> NAME/KEY: misc_feature
<222> LOCATION: (2)..(3)
<223> OTHER INFORMATION: Thiolated bond
<220> FEATURE:
<221> NAME/KEY: misc_feature
<222> LOCATION: (3)..(4)
<223> OTHER INFORMATION: Thiolated bond
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
```

-continued

<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (13)..(15)
<223> OTHER INFORMATION: Beta-D-oxy-LNA
<220> FEATURE:
<221> NAME/KEY: misc_feature
<222> LOCATION: (14)..(15)
<223> OTHER INFORMATION: Thiolated bond
<220> FEATURE:
<221> NAME/KEY: misc_feature
<222> LOCATION: (15)..(16)
<223> OTHER INFORMATION: Thiolated bond

<400> SEQUENCE: 9
tccgtcatcg ctcctc                                                    16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-amino-LNA
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:

```
<221> NAME/KEY: misc_feature
<222> LOCATION: (12)..(13)
<223> OTHER INFORMATION: Thiolated bond
<220> FEATURE:
<221> NAME/KEY: modified_base
<222> LOCATION: (13)..(15)
<223> OTHER INFORMATION: Beta-D-amino-LNA

<400> SEQUENCE: 10
tctgtaatag cccccc                                                    16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiolated bond
<220> FEATURE:
<221> NAME/KEY: modified_base
<222> LOCATION: (1)..(3)
<223> OTHER INFORMATION: Beta-D-amino-LNA
<220> FEATURE:
<221> NAME/KEY: misc_feature
<222> LOCATION: (2)..(3)
<223> OTHER INFORMATION: Thiolated bond
<220> FEATURE:
<221> NAME/KEY: misc_feature
<222> LOCATION: (3)..(4)
<223> OTHER INFORMATION: Thiolated bond
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (13)..(15)
```

-continued

```
<223> OTHER INFORMATION: Beta-D-amino-LNA
<220> FEATURE:
<221> NAME/KEY: misc_feature
<222> LOCATION: (14)..(15)
<223> OTHER INFORMATION: Thiolated bond
<220> FEATURE:
<221> NAME/KEY: misc_feature
<222> LOCATION: (15)..(16)
<223> OTHER INFORMATION: Thiolated bond

<400> SEQUENCE: 11
tctgtaatag cccccc                                                 16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: modified_base
<222> LOCATION: (13)..(15)
<223> OTHER INFORMATION: Beta-D-oxy-LNA

<400> SEQUENCE: 12
tctgtaatag cccccc                                                 16

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: misc_feature
<222> LOCATION: (1)..(2)
<223> OTHER INFORMATION: Thiolated bond
<220> FEATURE:
<221> NAME/KEY: modified_base
<222> LOCATION: (1)..(3)
<223> OTHER INFORMATION: Beta-D-oxy-LNA
<220> FEATURE:
<221> NAME/KEY: misc_feature
<222> LOCATION: (2)..(3)
<223> OTHER INFORMATION: Thiolated bond
<220> FEATURE:
<221> NAME/KEY: misc_feature
<222> LOCATION: (3)..(4)
<223> OTHER INFORMATION: Thiolated bond
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (13)..(15)
<223> OTHER INFORMATION: Beta-D-oxy-LNA
<220> FEATURE:
<221> NAME/KEY: misc_feature
<222> LOCATION: (14)..(15)
<223> OTHER INFORMATION: Thiolated bond
<220> FEATURE:
<221> NAME/KEY: misc_feature
<222> LOCATION: (15)..(16)
<223> OTHER INFORMATION: Thiolated bond

<400> SEQUENCE: 13
tctgtaatag cccccc                                                      16

<210> SEQ ID NO 14
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-thio-LNA
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: modified_base
<222> LOCATION: (13)..(15)
<223> OTHER INFORMATION: Beta-D-thio-LNA

<400> SEQUENCE: 14
tccgtcatcg ctcctc                                                      16

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiolated bond
<220> FEATURE:
<221> NAME/KEY: modified_base
<222> LOCATION: (1)..(3)
<223> OTHER INFORMATION: Beta-D-thio-LNA
<220> FEATURE:
<221> NAME/KEY: misc_feature
<222> LOCATION: (2)..(3)
<223> OTHER INFORMATION: Thiolated bond
<220> FEATURE:
<221> NAME/KEY: misc_feature
<222> LOCATION: (3)..(4)
<223> OTHER INFORMATION: Thiolated bond
<220> FEATURE:
<221> NAME/KEY: misc_feature
<222> LOCATION: (4)..(5)
<223> OTHER INFORMATION: Thiolated bond
```

```
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (13)..(15)
<223> OTHER INFORMATION: Beta-D-thio-LNA
<220> FEATURE:
<221> NAME/KEY: misc_feature
<222> LOCATION: (14)..(15)
<223> OTHER INFORMATION: Thiolated bond
<220> FEATURE:
<221> NAME/KEY: misc_feature
<222> LOCATION: (15)..(16)
<223> OTHER INFORMATION: Thiolated bond

<400> SEQUENCE: 15
tccgtcatcg ctcctc                                                       16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: Beta-D-thio-LNA
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
```

```
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: modified_base
<222> LOCATION: (12)..(16)
<223> OTHER INFORMATION: Beta-D-oxy-LNA

<400> SEQUENCE: 16
ttttgtcatc gtcttt                                                  16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-thio-LNA
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: modified_base
<222> LOCATION: (13)..(15)
<223> OTHER INFORMATION: Beta-D-thio-LNA

<400> SEQUENCE: 17
tccgtcatcg ctcctc                                                  16
```

```
<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiolated bond
<220> FEATURE:
<221> NAME/KEY: modified_base
<222> LOCATION: (1)..(3)
<223> OTHER INFORMATION: Beta-D-thio-LNA
<220> FEATURE:
<221> NAME/KEY: misc_feature
<222> LOCATION: (2)..(3)
<223> OTHER INFORMATION: Thiolated bond
<220> FEATURE:
<221> NAME/KEY: misc_feature
<222> LOCATION: (3)..(4)
<223> OTHER INFORMATION: Thiolated bond
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (13)..(15)
<223> OTHER INFORMATION: Beta-D-thio-LNA
<220> FEATURE:
<221> NAME/KEY: misc_feature
<222> LOCATION: (14)..(15)
<223> OTHER INFORMATION: Thiolated bond
<220> FEATURE:
<221> NAME/KEY: misc_feature
<222> LOCATION: (15)..(16)
<223> OTHER INFORMATION: Thiolated bond

<400> SEQUENCE: 18
```
tccgtcatcg ctcctc                                                        16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-thio-LNA
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: modified_base
<222> LOCATION: (13)..(15)
<223> OTHER INFORMATION: Beta-D-thio-LNA

<400> SEQUENCE: 19
tctgtaatag cccccc                                                        16

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiolated bond
<220> FEATURE:
<221> NAME/KEY: modified_base
<222> LOCATION: (1)..(3)
<223> OTHER INFORMATION: Beta-D-thio-LNA
<220> FEATURE:
<221> NAME/KEY: misc_feature
<222> LOCATION: (2)..(3)

```
<223> OTHER INFORMATION: Thiolated bond
<220> FEATURE:
<221> NAME/KEY: misc_feature
<222> LOCATION: (3)..(4)
<223> OTHER INFORMATION: Thiolated bond
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (13)..(15)
<223> OTHER INFORMATION: Beta-D-thio-LNA
<220> FEATURE:
<221> NAME/KEY: misc_feature
<222> LOCATION: (14)..(15)
<223> OTHER INFORMATION: Thiolated bond
<220> FEATURE:
<221> NAME/KEY: misc_feature
<222> LOCATION: (15)..(16)
<223> OTHER INFORMATION: Thiolated bond

<400> SEQUENCE: 20
tctgtaatag cccccc                                                    16

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Alpha-L-oxy-LNA
<220> FEATURE:
<221> NAME/KEY: misc_feature
<222> LOCATION: (4)..(5)
<223> OTHER INFORMATION: Thiolated bond
<220> FEATURE:
```

```
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: modified_base
<222> LOCATION: (13)..(15)
<223> OTHER INFORMATION: Alpha-L-oxy-LNA

<400> SEQUENCE: 21
tccgtcatcg ctcctc                                                 16

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiolated bond
<220> FEATURE:
<221> NAME/KEY: modified_base
<222> LOCATION: (1)..(3)
<223> OTHER INFORMATION: Alpha-L-oxy-LNA
<220> FEATURE:
<221> NAME/KEY: misc_feature
<222> LOCATION: (2)..(3)
<223> OTHER INFORMATION: Thiolated bond
<220> FEATURE:
<221> NAME/KEY: misc_feature
<222> LOCATION: (3)..(4)
<223> OTHER INFORMATION: Thiolated bond
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
```

```
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (13)..(15)
<223> OTHER INFORMATION: Alpha-L-oxy-LNA
<220> FEATURE:
<221> NAME/KEY: misc_feature
<222> LOCATION: (14)..(15)
<223> OTHER INFORMATION: Thiolated bond
<220> FEATURE:
<221> NAME/KEY: misc_feature
<222> LOCATION: (15)..(16)
<223> OTHER INFORMATION: Thiolated bond

<400> SEQUENCE: 22
tccgtcatcg ctcctc                                                        16

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: Beta-D-oxy-LNA
<220> FEATURE:
<221> NAME/KEY: misc_feature
<222> LOCATION: (5)..(6)
<223> OTHER INFORMATION: Thiolated bond
<220> FEATURE:
<221> NAME/KEY: modified_base
<222> LOCATION: (6)..(6)
<223> OTHER INFORMATION: Alpha-L-oxy-LNA
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
```

<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: modified_base
<222> LOCATION: (12)..(12)
<223> OTHER INFORMATION: Alpha-L-oxy-LNA
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (14)..(16)
<223> OTHER INFORMATION: Beta-D-oxy-LNA

<400> SEQUENCE: 23
ttccgtcatc gtcttt                                                    16

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: Alpha-L-oxy-LNA
<220> FEATURE:
<221> NAME/KEY: misc_feature
<222> LOCATION: (5)..(6)
<223> OTHER INFORMATION: Thiolated bond
<220> FEATURE:
<221> NAME/KEY: modified_base
<222> LOCATION: (6)..(6)
<223> OTHER INFORMATION: Alpha-L-oxy-LNA
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: modified_base
<222> LOCATION: (12)..(12)
<223> OTHER INFORMATION: Alpha-L-oxy-LNA
<220> FEATURE:
<221> NAME/KEY: misc_feature
<222> LOCATION: (12)..(13)

```
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (14)..(15)
<223> OTHER INFORMATION: Alpha-L-oxy-LNA
<220> FEATURE:
<221> NAME/KEY: modified_base
<222> LOCATION: (16)..(16)
<223> OTHER INFORMATION: Beta-D-oxy-LNA

<400> SEQUENCE: 24
ttccgtcatc gtcttt                                                  16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: Beta-D-oxy-LNA
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: modified_base
<222> LOCATION: (8)..(8)
<223> OTHER INFORMATION: Alpha-L-oxy-LNA
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: modified_base
<222> LOCATION: (12)..(16)
<223> OTHER INFORMATION: Beta-D-oxy-LNA

<400> SEQUENCE: 25
ttccgtcatc gtcttt                                                  16

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(3)
<223> OTHER INFORMATION: Beta-D-oxy-LNA
<220> FEATURE:
<221> NAME/KEY: modified_base
<222> LOCATION: (4)..(4)
<223> OTHER INFORMATION: Alpha-L-oxy-LNA
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: modified_base
<222> LOCATION: (8)..(8)
<223> OTHER INFORMATION: Alpha-L-oxy-LNA
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: modified_base
<222> LOCATION: (12)..(12)
<223> OTHER INFORMATION: Alpha-L-oxy-LNA
<220> FEATURE:
<221> NAME/KEY: modified_base
<222> LOCATION: (13)..(16)
<223> OTHER INFORMATION: Beta-D-oxy-LNA

<400> SEQUENCE: 26
ttccgtcatc gtcttt                                                   16

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Alpha-L-oxy-LNA
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
```

<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: modified_base
<222> LOCATION: (13)..(15)
<223> OTHER INFORMATION: Alpha-L-oxy-LNA

<400> SEQUENCE: 27
tccgtcatcg ctcctc                                                     16

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiolated bond
<220> FEATURE:
<221> NAME/KEY: modified_base
<222> LOCATION: (1)..(3)
<223> OTHER INFORMATION: Alpha-L-oxy-LNA
<220> FEATURE:
<221> NAME/KEY: misc_feature
<222> LOCATION: (2)..(3)
<223> OTHER INFORMATION: Thiolated bond
<220> FEATURE:
<221> NAME/KEY: misc_feature
<222> LOCATION: (3)..(4)
<223> OTHER INFORMATION: Thiolated bond
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond

```
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (13)..(15)
<223> OTHER INFORMATION: Alpha-L-oxy-LNA
<220> FEATURE:
<221> NAME/KEY: misc_feature
<222> LOCATION: (14)..(15)
<223> OTHER INFORMATION: Thiolated bond
<220> FEATURE:
<221> NAME/KEY: misc_feature
<222> LOCATION: (15)..(16)
<223> OTHER INFORMATION: Thiolated bond

<400> SEQUENCE: 28
tccgtcatcg ctcctc                                                      16

<210> SEQ ID NO 29
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Alpha-L-oxy-LNA
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
```

<222> LOCATION: (12)..(13)
<223> OTHER INFORMATION: Thiolated bond
<220> FEATURE:
<221> NAME/KEY: modified_base
<222> LOCATION: (13)..(15)
<223> OTHER INFORMATION: Alpha-L-oxy-LNA

<400> SEQUENCE: 29
tctgtaatag cccccc                          16

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiolated bond
<220> FEATURE:
<221> NAME/KEY: modified_base
<222> LOCATION: (1)..(3)
<223> OTHER INFORMATION: Alpha-L-oxy-LNA
<220> FEATURE:
<221> NAME/KEY: misc_feature
<222> LOCATION: (2)..(3)
<223> OTHER INFORMATION: Thiolated bond
<220> FEATURE:
<221> NAME/KEY: misc_feature
<222> LOCATION: (3)..(4)
<223> OTHER INFORMATION: Thiolated bond
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (13)..(15)
<223> OTHER INFORMATION: Alpha-L-oxy-LNA

```
<220> FEATURE:
<221> NAME/KEY: misc_feature
<222> LOCATION: (14)..(15)
<223> OTHER INFORMATION: Thiolated bond
<220> FEATURE:
<221> NAME/KEY: misc_feature
<222> LOCATION: (15)..(16)
<223> OTHER INFORMATION: Thiolated bond

<400> SEQUENCE: 30
tctgtaatag cccccc                                                       16

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: Beta-D-oxy-LNA
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: modified_base
<222> LOCATION: (13)..(15)
<223> OTHER INFORMATION: Beta-D-oxy-LNA

<400> SEQUENCE: 31
ttccgtcatc gtcttt                                                       16

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(3)
<223> OTHER INFORMATION: Beta-D-oxy-LNA
<220> FEATURE:
<221> NAME/KEY: misc_feature
<222> LOCATION: (4)..(5)
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: modified_base
<222> LOCATION: (13)..(15)
<223> OTHER INFORMATION: Beta-D-oxy-LNA
<220> FEATURE:
<221> NAME/KEY: misc_feature
<222> LOCATION: (15)..(16)
<223> OTHER INFORMATION: Thiolated bond

<400> SEQUENCE: 32
ttccgtcatc gtcttt                                                    16

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Thiolated bond
<220> FEATURE:
<221> NAME/KEY: modified_base
<222> LOCATION: (1)..(3)
<223> OTHER INFORMATION: Beta-D-oxy-LNA
<220> FEATURE:
<221> NAME/KEY: misc_feature
<222> LOCATION: (2)..(3)
<223> OTHER INFORMATION: Thiolated bond
<220> FEATURE:
<221> NAME/KEY: misc_feature
<222> LOCATION: (3)..(4)
<223> OTHER INFORMATION: Thiolated bond
<220> FEATURE:
<221> NAME/KEY: misc_feature
<222> LOCATION: (4)..(5)
```

```
<223> OTHER INFORMATION: Thiolated bond
<220> FEATURE:
<221> NAME/KEY: misc_feature
<222> LOCATION: (5)..(6)
<223> OTHER INFORMATION: Thiolated bond
<220> FEATURE:
<221> NAME/KEY: misc_feature
<222> LOCATION: (6)..(7)
<223> OTHER INFORMATION: Thiolated bond
<220> FEATURE:
<221> NAME/KEY: misc_feature
<222> LOCATION: (7)..(8)
<223> OTHER INFORMATION: Thiolated bond
<220> FEATURE:
<221> NAME/KEY: misc_feature
<222> LOCATION: (8)..(9)
<223> OTHER INFORMATION: Thiolated bond
<220> FEATURE:
<221> NAME/KEY: misc_feature
<222> LOCATION: (9)..(10)
<223> OTHER INFORMATION: Thiolated bond
<220> FEATURE:
<221> NAME/KEY: misc_feature
<222> LOCATION: (10)..(11)
<223> OTHER INFORMATION: Thiolated bond
<220> FEATURE:
<221> NAME/KEY: misc_feature
<222> LOCATION: (11)..(12)
<223> OTHER INFORMATION: Thiolated bond
<220> FEATURE:
<221> NAME/KEY: misc_feature
<222> LOCATION: (12)..(13)
<223> OTHER INFORMATION: Thiolated bond
<220> FEATURE:
<221> NAME/KEY: misc_feature
<222> LOCATION: (13)..(14)
<223> OTHER INFORMATION: Thiolated bond
<220> FEATURE:
<221> NAME/KEY: modified_base
<222> LOCATION: (13)..(15)
<223> OTHER INFORMATION: Beta-D-oxy-LNA
<220> FEATURE:
<221> NAME/KEY: misc_feature
<222> LOCATION: (14)..(15)
<223> OTHER INFORMATION: Thiolated bond
<220> FEATURE:
<221> NAME/KEY: misc_feature
<222> LOCATION: (15)..(16)
<223> OTHER INFORMATION: Thiolated bond

<400> SEQUENCE: 33
ttccgtcatc gtcttt                                                         16
```

ANTISENSE DESIGN

RELATED APPLICATIONS

This application is a continuation of U.S. Ser. No. 15/237,307, which was filed Aug. 15, 2016, which is a continuation of U.S. Ser. No. 13/797,919, which was filed on Mar. 12, 2013, which claims priority to U.S. application Ser. No. 10/535,472, which was filed on Dec. 19, 2005, which is a National Phase Application of PCT/DK2003/00788, which was filed Nov. 18, 2003 and Application No. PA2002/01774, filed Nov. 18, 2002, and Application No. PA2003/01540, filed Oct. 20, 2003.

FIELD OF INVENTION

The present invention relates to pharmaceuticals comprising antisense oligonucleotides, and novel oligonucleotides having improved antisense properties.

BACKGROUND OF THE INVENTION

The Professors Imanishi and Wengel independently invented Locked Nucleic Acid (LNA) in 1997 (International Patent Applications WO 99/14226, WO 98/39352; P. Nielsen et al, *J. Chem. Soc., Perkin Trans.* 1, 1997, 3423; P. Nielsen et al., *Chem. Commun.*, 1997, 9, 825; N. K. Christensen et al., *J. Am. Chem. Soc.*, 1998, 120, 5458; A. A. Koshkin et al., *J. Org. Chem.*, 1998, 63, 2778; A. A Koshkin et al. *J. Am. Chem. Soc.* 1998, 120, 13252-53; Kumar et al. *Bioorg, & Med. Chem. Lett.*, 1998, 8, 2219-2222; and S. Obika et al., *Bioorg. Med. Chem. Lett.*, 1999, 515). The first LNA monomer was based on the 2'-O—CH$_2$-4' bicyclic structure. Due to the configuration of this structure it is called: beta-D-oxy-LNA. This oxy-LNA has since then showed promising biological applications (Braasch & Corey, *Biochemistry*, 2002, 41(14), 4503-19; Childs et al. *PNAS*, 2002, 99(17), 11091-96; Crinelli et al., *Nucl. Acid. Res.*, 2002, 30(11), 2435-43; Elayadi et al., *Biochemistry*, 2002, 41, 9973-9981; Jacobsen et al., *Nucl. Acid. Res.*, 2002, 30(19), in press; Kurreck et al., *Nucl. Acid. Res.*, 2002, 30(9), 1911-1918; Simeonov & Nikiforov, *Nucl. Acid. Res.*, 2002, 30(17); Alayadi & Corey, *Curr. opinion in Inves. Drugs.*, 2001, 2(4), 558-61; Obika et al., *Bioorg. & Med. Chem.*, 2001, 9, 1001-11; Braasch & Corey, *Chem. & Biol.*, 2000, 55, 1-7; Wahlestedt et al., *PNAS*, 2000, 97(10), 5633-38), Freier & Altmann, *Nucl. Acid Res.*, 1997, 25, 4429-43; Cook, 1999, *Nucleosides & Nucleotides*, 18(6&7), 1141-62.

Right after the discovery of oxy-LNA the bicyclic furanosidic structure was chemically derivatised. Thus, the 2'-S—CH$_2$-4' (thio-LNA) and the 2'-NH—CH$_2$-4' (amino-LNA) bicyclic analogues were disclosed (Singh, S. K., *J. Org. Chem.*, 1998, 63, 6078-79; Kumar et al. *Bioorg, & Med. Chem. Lett.*, 1998, 8, 2219-2222; Singh et al. *J. Org. Chem.*, 1998, 63, 10035-39). The synthesis of the thio-LNA containing uridine as nucleobase has been shown (Singh, S. K., *J. Org. Chem.*, 1998, 63, 6078-79). For amino-LNA the synthesis of the thymidine nucleobase has been disclosed (Kumar et al. *Bioorg, & Med. Chem. Lett.*, 1998, 8, 2219-2222; Singh et al. *J. Org. Chem.*, 1998, 63, 10035-39). A series of LNA-diastereoisomers have been prepared (Rajwanshi et al., *J. Chem Commun.* 1999; 2073-2074; Hakansson & Wengel, *Bioorg Med Chem Lett* 2001; 11(7):935-938; Rajwanshi et al., *Chem Commun.*, 1999; 1395-1396; Wengel at al., *Nucleosides Nucleotides Nucleic Acids*, 2001; 20(4-7):389-396; Rajwanshi et al., *Angew. Chem. Int. Ed.*, 2000; 39:1656-1659; Petersen et al., *J. Amer. Chem. Soc.*, 2001, 123(30), 7431-32; Sørensen et al., *J. Amer. Chem. Soc.*, 2002, 124(10), 2164-76; Vester et al., *J. Amer. Chem. Soc.*, 2002, 124(46), 13682-13683). In the prior art the synthesis of alpha-L-xylo, xylo-LNA, and alpha-L-oxy-LNA containing thymidine bases have been shown. For the alpha-L-oxy-LNA also the 5-methyl and adenine nucleosides have been synthesised. The melting temperature (Tm) of duplexes containing the LNA distereoisomers have been presented. It turned out that the alpha-L-oxy-LNA has interesting properties. It was shown that the alpha-L-oxy-LNA can be incorporated in complex chimerae comprising DNA/RNA residues and be adapted in the oligo structure and increase the binding. This property of being incorporated in oligonucleotides containing several other monomeric classes and act co-operatively is a property that the alpha-L-oxy-LNA shares with the parent oxy-LNA. Furthermore, it has been demonstrated that a segment of 4 consecutive alpha-L-T monomers can be incorporated in conjunction with a segment of 4 consecutive oxy-LNA-T monomers (Rajwanshi et al., *Chem. Commun.*, 1999, 2073-74). Increased stability of oligonucleotides containing alpha-L-oxy-LNA monomers ($^{Me}$C, A, T-monomers) have been demonstrated. The alpha-L-oxy-LNA monomers were incorporated into oligonucleotides with alternating alpha-L-oxy-LNA and DNA monomers (mix-mers) and in fully modified alpha-L-oxy-LNA oligomers. The stability was compared to oxy-LNA and to DNA and it was found that alpha-L-oxy-LNA monomers displaced the same protection pattern as oxy-LNA (Sørensen, et al., J. Amer. Chem. Soc., 2002, 124(10), 2164-76). The same alpha-L-oxy-LNA containing oligonucleotides were tested in RNase H assays and it was found that the designs disclosed were not efficiently recruiting RNase H. When these examples are taken together also in combination with the data published by Arzumanov et al (Biochemistry 2001, 40, 14645-54) it has not been shown that alpha-L-oxy-LNA containing oligonucleotides efficiently recruits RNase H.

Oligonucleotides containing any combination of the diastereoisomers and any other LNA family member has not been demonstrated.

Natural dsDNA exists at physiological pH as a B-form helix, whereas dsRNA exists as an A-form helix. A helix formed by DNA and RNA exists in an intermediate A/B-form. This morphological difference is originated in the difference in the preferred sugar conformations of the deoxyriboses and the riboses. The furanose ring of deoxyribose exists at room temperature in an equilibrium between C2'-endo (S-type) and C3'-endo (N-type) conformation with an energy barrier of ~2 kcal/mol (FIG. 3). For deoxyribose the S-type conformation is slightly lowered in energy (~0.6 kcal/mol) compared to the N-type and explains why DNA is found in the S-type conformation. The conformation leads to the B-form helix. For ribose, and RNA, the preference is for the N-type that leads to the A-form helix. The A-form helix is associated with higher hybridisation stability. The oxy-LNA and the LNA analogues are locked in the N-conformation and consequently the oligonucleotides they are forming will be RNA-like. The alpha-L-oxy-LNA is locked in a S-type and therefore the oligonucleotides that it will form will be more DNA like (Sørensen et al., *J. Amer. Chem. Soc.*, 2002, 124(10), 2164-76; Rajwanshi et al., *Angew. Chem. Int. Ed.*, 2000; 39:1656-1659). Molecular strategies are being developed to modulate unwanted gene expression that either directly causes, participates in, or aggravates a disease state. One such strategy involves inhibiting gene expression with oligonucleotides complementary in sequence to the messenger RNA of a target gene. The messenger RNA strand is a copy of the coding DNA strand and is therefore, as the DNA strand, called the sense strand. Oligonucleotides that hybridise to the sense strand are called antisense oligonucleotides. Binding of these strands to mRNA interferes with the translation process and consequently with gene expression. Zamecnik and co-workers originally described the Antisense strategy and the principle has since then attracted a lot of interest (Zamecnik & Stephenson, PNAS, 1978, 75(1), 280-4; Bennet & Cowset, Biochim. Biophys. Acta, 1999, 1489, 19-30; Crooke, 1998, Biotechnol. Genet. Eng Rev., 15, 121-57; Wengel, J. In Antisense Drug Technology; Principles, Strategies, and Applications; Edited by Crooke, S. T., Ed.; Marcel Dekker, Inc.: New York, Basel, 2001; pp 339-357).

It has been a long sought goal to develop drugs with the capacity to destroy malignant genes base specifically. The applications of such drugs in e.g. cancer and infections diseases are self-evident. Native oligonucleotides cannot be employed as such mainly due to their instability in cellular media and to too low affinity for the target genes. The wish to develop nucleic acid probes with improved properties in this regard has been the main driver behind the massive synthesis effort in the area of nucleic acid analogue preparation. The most important guideline in this work has been to design the DNA analogues in such a way that the DNA analogue would attain the N-type/"RNA"-like conformation that is associated with the higher affinity of the oligonucleotides to nucleic acids.

One of the important mechanisms involved in Antisense is the RNase H mechanism. RNase H is an intra cellular enzyme that cleaves the RNA strand in RNA/DNA duplexes. Therefore, in the search for efficient Antisense oligonucleotides, it has been an important hallmark to prepare oligonucleotides that can activate RNase H. However, the prerequisite for an oligonucleotide in this regard is therefore that the oligo is DNA-like and as stated above most high affinity DNA analogues induces RNA-like oligonucleotides. Therefore, to compensate for the lack of RNase H substrate ability of most DNA analogues (like e.g. 2'-OMe DNA analogue and oxy-LNA) the oligonucleotides must have segments/consecutive stretches of DNA and/or phosphorothioates. Depending on the design of the segments of such oligonucleotides they are usually called Gap-mers, if the DNA segment is flanked by the segments of the DNA analogue, Head-mers, if the segment of the DNA analogue is located in the 5' region of the oligonucleotide, and Tail-mers, if the segment of the DNA analogue is located in the 3' region of the oligonucleotide.

It should be mentioned that other important mechanisms are involved in Antisense that are not dependent on RNase H activation. For such oligonucleotides the DNA analogues, like LNA, can be placed in any combination design (Childs et al. PNAS, 2002, 99(17), 11091-96; Crinelli et al., Nucl. Acid. Res., 2002, 30(11), 2435-43; Elayadi et al., Biochemistry, 2002, 1, 9973-9981; Kurreck et al., Nucl. Acid. Res., 2002, 30(9), 1911-1918; Alayadi & Corey, Curr. opinion in Inves. Drugs., 2001, 2(4), 558-61; Braasch & Corey, Chem. & Biol., 2000, 55, 1-7).

In contrast to the beta-D-oxy-LNA the alpha-L-oxy-LNA has a DNA-like locked conformation and it has been demonstrated that alpha-L-oxy-LNA can activate RNase H (Sørensen et al., J. Amer. Chem. Soc., 2002, 124(10), 2164-76). However, the cleavage rate of RNase H is much lower compared to DNA in the disclosed designs and thus, the oligonucleotides in the disclosed designs have not been shown to be efficient Antisense reagents.

SUMMARY OF THE INVENTION

The present inventors have found a novel class of pharmaceuticals which can be used in antisense therapy. Also, the inventors disclose novel oligonucleotides with improved antisense properties. The novel oligonucleotides are composed of at least one Locked Nucleic Acid (LNA) selected from beta-D-thio/amino-LNA or alpha-L-oxy/thio/amino-LNA. The oligonucleotides comprising LNA may also include DNA and/or RNA nucleotides.

The present inventors have demonstrated that α-L-oxy-LNA surprisingly provides the possibility for the design of improved Antisense oligonucleotides that are efficient substrates for RNase H. These novel designs are not previously described and the guidelines developed broaden the design possibilities of potent Antisense oligonucleotides. Also comprised in this invention is the disclosure of Antisense oligonucleotides having other improved properties than the capability of being RNase H substrates. The oligonucleotides comprise any combination of LNA-relatives with DNA/RNA, and their analogues, as well as oxy-LNA. The design of more potent Antisense reagents is a combination of several features. Among the features of these novel oligonucleotide designs are increased enzymatic stability, increased cellular uptake, and efficient ability to recrute RNase H. Also important is the relation between the length and the potency of the oligonucleotides (e.g. a 15-mer having the same potency as a 21-mer is regarded to be much more optimal). The potency of the novel oligonucleotides comprised in this invention is tested in cellular in vitro assays and in vivo assays. It is furthermore showed that the novel designs also improves the in vivo properties such as better pharmacokinetic/pharmacological properties and toxicity profiles.

Beta-D-Oxy-LNA and the Analogues Thio- and Amino LNA:

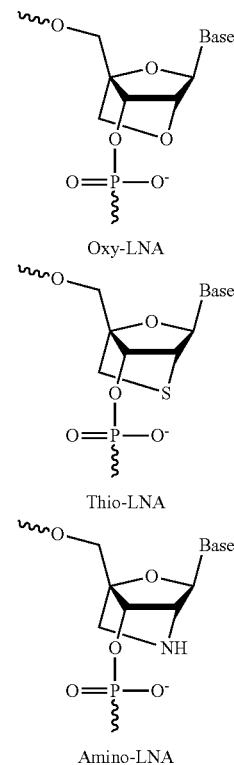

Lna Diastereoisomers:

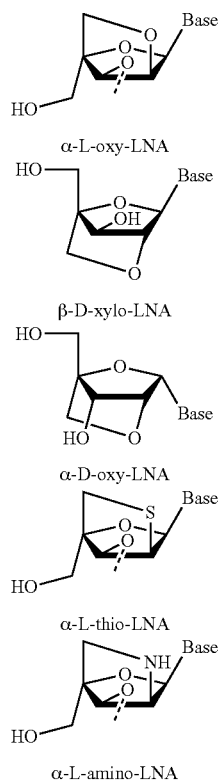

Sugar Conformations in DNA:

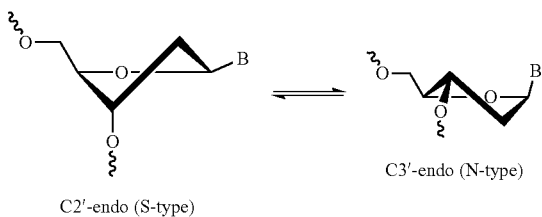

DESCRIPTION OF THE DRAWINGS

FIG. 6: Northern blot analysis of oligonucleotides containing beta-D-amino-LNA (2754), beta-D-thio-LNA (2748), alpha-L-oxy-LNA (2776) or beta-D-oxy-LNA (2742) at 50-400 nM in 15PC3 cells transfected with Lipofectamine2000; comparison with the corresponding mismatch control at 400 nM. Mismatch controls (thio=2750; amino=2756; alpha=2778) were also analyzed at 30-90 nM and compared with the corresponding match at 30 nM. Table containing Northern blot analysis of oligonucleotides containing beta-D-amino-LNA (2754), alpha-L-oxy-LNA (2776) and beta-D-oxy-LNA (2742) at 5-40 nM in 15PC3 cells transfected with Lipofectamine2000; comparison with the corresponding mismatch controls at 20 nM.

FIG. 7A: Serum clearance of titriated 2754=amino, 2748=thio and 2742=oxy after 30 min of intravenous bolus injection. 2131 is an oligonucleotide gapmer containing beta-D-oxy-LNA used as a reference.

FIG. 7B: Biodistribution of titriated 2754=amino, 2748=thio and 2742=oxy after 30 min of intravenous bolus injection. 2131 is an oligonucleotide gapmer containing beta-D-oxy-LNA used as a reference.

FIG. 7C: Specific tissue uptake of titriated 2754=amino, 2748=thio and 2742=oxy after 30 min of intravenous bolus injection. 2131 is an oligonucleotide gapmer containing beta-D-oxy-LNA used as a reference.

DETAILED DESCRIPTION

Figure 1:
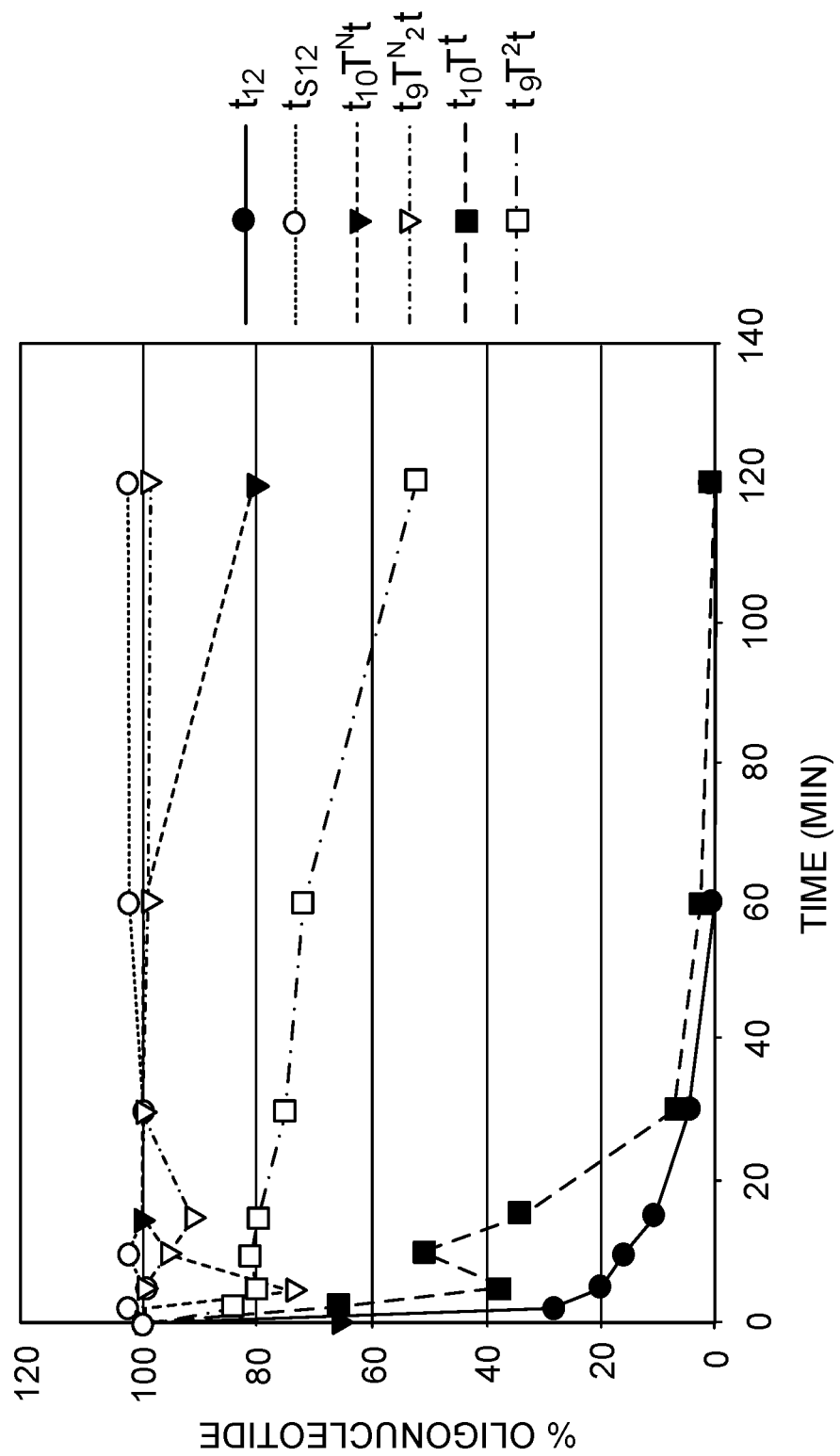
FIG. 1: Stability of oligonucleotides containing beta-D-amino-LNA against SVPD. (Capital letters are LNA, $T^N$ stands for beta-D-amino-LNA and small letters are DNA. The oligonucleotide is synthesized on deoxynucleoside-support.
Figure 2A:
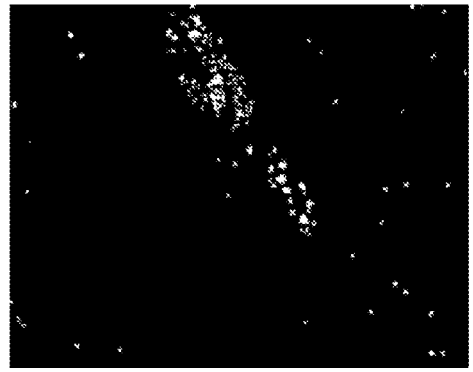
FIG. 2A: Subcellular distribution in MiaPacaII cells of FAM-labeled oligonucleotide 2740 transfected with Lipofectamine2000.
Figure 2B:
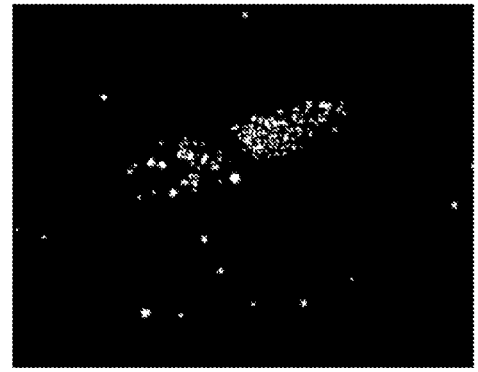
FIG. 2B: Subcellular distribution in MiaPacaII cells of FAM-labeled oligonucleotide 2774 transfected with Lipofectamine2000.
Figure 2C:
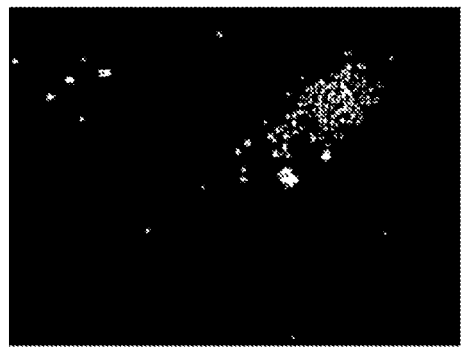
FIG. 2C: Subcellular distribution in MiaPacaII cells of FAM-labeled oligonucleotide 2752 transfected with Lipofectamine2000.
Figure 2D:
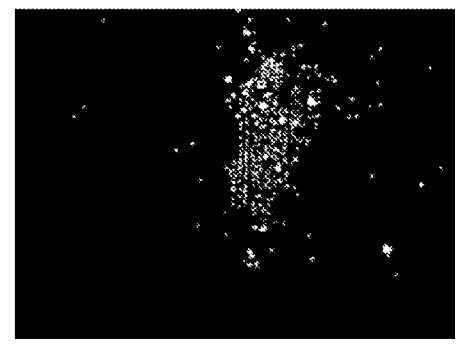
FIG. 2D: Subcellular distribution in MiaPacaII cells of FAM-labeled oligonucleotide 2746 transfected with Lipofectamine2000.

Thus, the present invention in it broadest scope relates to a pharmaceutical composition comprising a therapeutically active antisense oligonucleotide construct which (i) comprises at least one locked nucleic acid unit selected from the group consisting of amino-LNA and thio-LNA and derivatives thereof; or (ii) comprises at least two consecutively located locked nucleotide units of which at least one is selected from the group consisting of alpha-L-oxy-LNA and derivatives thereof. The antisense construct can be in the form of a salt or in the form of prodrug or salts of such prodrug. The invention thus relates to pharmaceutical compositions in which an active ingredient is a pharmaceutically acceptable salt, prodrug (such as an ester) or salts of such prodrug of the above oligonucleotide construct. Both amino- and thio-LNA can be either alpha or beta configuration, and in (i), the oligonucleotide construct encompasses constructs with at least one (such as 1, 2, 3, 4, 5, 6, 7, 8, 9, or 10) units selected from the group consisting of: alpha-L-thio-LNA, beta-D-thio-LNA, beta-D-amino-LNA, alpha-L-amino-LNA and derivatives thereof; optionally in combination with at least one (such as 1, 2, 3, 4, 5, 6, 7, 8, 9, 10, 11, 12, 13, 14, 15, 16, 17, 18, 19, 20 or more) further independently selected locked or non-locked nucleotide units. Examples on these further units are oxy-LNA (such as alpha-L or beta-D), thio/amino LNA (such as alpha-L or beta-D), a nucleotide unit which has a 2'-deoxy-erythro-pentofuranosyl sugar moiety (such as a DNA nucleotide), a nucleotide unit which has a ribo-pentofuranosyl sugar moiety (such as a RNA nucleotide); and derivatives thereof. In (ii), the oligonucleotide construct encompasses constructs with at least two (such as 2, 3, 4, 5, 6, 7, 8, 9, 10 or more) consecutively located nucleotide units, of which at least one (such as 1, 2, 3, 4, 5, 6, 7 or more) is alpha-L-oxy LNA units or derivatives thereof. In addition to the alpha-L-oxy LNA units or derivatives thereof, the sequence of consecutively located locked nucleotide units optionally comprises other locked nucleotide units (such as the units defined herein). Besides the essential two consecutively located locked nucleotide units, the construct in (ii) optionally comprises one or more (such as 1, 2, 3, 4, 5, 6, 7, 8, 9, 10, 11, 12, 13, 14, 15, 16, 17, 18, 19, 20 or more) independently selected locked or non-locked nucleotide units (such as the units defined herein).

In an interesting embodiment, the invention relates to a pharmaceutical composition in which the antisense oligonucleotide construct comprises two adjacently located nucleotide sequences A and B, where A represents a sequence of nucleotide units comprising (i) at least one locked nucleotide unit selected from the group consisting of thio-LNA, amino-LNA (both in either alpha-L or beta-D configuration) and derivatives thereof, or (ii) at least two consecutively located locked nucleotide units of which at least one is selected from the group consisting of alpha-L-oxy-LNA and derivatives thereof; and B represents one nucleotide unit or a sequence of nucleotide units, with the proviso that at least one nucleotide unit in B has a 2'-deoxy-erythro-pentofuranosyl sugar moiety or a ribo-pentofuranosyl sugar moiety. Sequence A can additionally comprise at least one further locked nucleotide unit (such as 2, 3, 4 or 5 units), preferably selected independently from the group consisting of amino-LNA, thio-LNA (both in either alpha-L or beta-D configuration), alpha-L-oxy-LNA and derivatives thereof.

In an other interesting embodiment, the invention relates to a pharmaceutical composition comprising an oligonucleotide construct which contains three adjacently located nucleotide sequences, A, B and C, in the following order (5' to 3'):

A-B-C or C-B-A, in which

A represents a sequence comprising at least two consecutively located locked nucleotide units, at least one of which is an alpha-L-oxy-LNA unit, and which sequence optionally contains one or more (such as 2, 3, 4 or 5) non-locked nucleotide units (such as deoxyribonucleotide units, ribonucleotide units or derivatives thereof) and/or optionally contains one or more (such as 2, 3, 4 or 5) locked nucleotide units, such as a unit selected from the group consisting of oxy-LNA, thio-LNA, amino-LNA (all in either alpha-L or beta-D configuration) and derivatives thereof;

B represents one nucleotide unit or a sequence of nucleotide units, with the proviso that at least one nucleotide unit in B has a 2'-deoxy-erythro-pentofuranosyl sugar moiety or a ribo-pentofuranosyl moiety; and C represents a sequence comprising at least two consecutively located locked nucleotide units, at least one of which is an alpha-L-oxy-LNA unit, and which sequence optionally contains one or more (such as 2, 3, 4 or 5) non-locked nucleotide units (such as deoxyribonucleotide units, ribonucleotide units or derivatives thereof) and/or optionally contains one or more (such as 2, 3, 4 or 5) locked nucleotide units, such as a unit selected from the group consisting of oxy-LNA, thio-LNA, amino-LNA (all in either alpha-L or beta-D configuration) and derivatives thereof.

The invention also relates to an oligonucleotide construct which comprises at least one nucleotide sequence comprising one or more nucleotide units selected from the group consisting of amino-LNA, thio-LNA (in all configurations) and derivatives thereof; with the proviso that the following oligonucleotide constructs are excluded:

(i) 5'-d(GTGAVATGC), 5'-d(GVGAVAVGC), 5'-d(GTGAXATGC), 5'-d(GXGAXAXGC), 5'-d(GXGVXVXGC), in which sequences V represents a beta-D-amino-LNA thymine unit, and X represents a beta-D-methylamino-LNA thymine unit; and (ii) 5'-d(GTGAYATGC), 5'-d(GYGAYAYGC) and 5'-d(GYGYYYYGC) in which sequences Y represents a beta-D-thio-LNA uracil unit.

The excluded oligonucleotides are previously disclosed by Singh et al and Kumar et al. (Kumar et al. *Bioorg, & Med. Chem. Lett.,* 1998, 8, 2219-2222; Singh et al. *J. Org. Chem.,* 1998, 63, 10035-39). It has collectively for the excluded LNA-relatives been shown that they can be incorporated into oligonucleotides. However, no biological properties have not been demonstrated or suggested.

A presently preferred group of oligonucleotide constructs of the invention comprises two adjacently located nucleotide sequences, A and B, where A represents a sequence of nucleotide units comprising at least one locked nucleotide unit selected from the group consisting of amino-LNA, thio-LNA (both in either alpha-L or beta-D) configuration, and derivatives thereof; and B represents one nucleotide unit or a sequence of nucleotide units, with the proviso that at least one nucleotide unit in B has a 2'-deoxy-erythro-pentofuranosyl sugar moiety or a ribo-pentofuranosyl moiety; especially constructs in which B represents a sequence of nucleotide units, said sequence contains a subsequence of at least three nucleotide units having 2'-deoxy-erythro-pentofuranosyl sugar moieties, such as 4, 5, 6, 7, 8, 9 or 10 nucleotide units, said subsequence optionally being spiked with an other nucleotide, preferably an alpha-L-oxy-LNA unit selected from the group consisting of alpha-L-amino-LNA, alpha-L-thio-LNA, alpha-L-oxy-LNA and derivatives thereof.

Also interesting is a construct according which comprises three adjacently located nucleotide sequences in the following order (5' to 3'):A-B-C, in which the nucleotide sequences A and B are as defined as above, and C represents a sequence of nucleotide units, which comprises at least one locked nucleotide unit selected from the group consisting of amino-LNA, thio-LNA (both in either alpha-L or beta-D configuration) and derivatives thereof.

In the above constructs, it is preferred that A has a length of 2-10 (preferably 2-8, such as 3, 4, 5, 6, 7) nucleotide units; B has a length of 1-10 (preferably 5-8, such as 6 or 7) nucleotide units; and C (if present) has a length of 2-10 (preferably 2-8, such as 3, 4, 5, 6, or 7) nucleotide units; so that the overall length of the construct is 6-30 (preferably 10-20, more preferably 12-18, such as 13, 14, 15, 16 or 17) nucleotide units.

A preferred embodiment of the above construct according to the invention is a construct in which A represents a sequence of nucleotide units comprising at least two consecutively located locked nucleotide units (such as 3, 4, 5, 6, 7, 8, 9 or 10 units), at least one of said locked nucleotide units being selected from the group consisting of amino-LNA, thio-LNA and derivatives thereof; C represents a sequence of nucleotide units comprising at least two consecutively located locked nucleotide units (such as 3, 4, 5, 6, 7, 8, 9 or 10 units), at least one of said locked nucleotide units being selected from the group consisting of amino-LNA, thio-LNA (in all configurations) and derivatives thereof, and/or B represents a sequence of least 2 nucleotide units (such as 3, 4, 5, 6, 7, 8, 9 or 10 units), which sequence in addition to the nucleotide unit(s) having 2'-deoxy-erythro-pentofuranosyl sugar moiety(ies) and/or ribo-pentofuranosyl moiety(ies), comprises nucleotides units which are selected independently from the group consisting of: locked nucleotide units (such as alpha-L-oxy-, -thio-, or -amino-nucleotide units) and derivatives thereof.

An other embodiment of the invention relates to an oligonucleotide construct which contains three adjacently located nucleotide sequences, A, B and C, in the following order (5' to 3'): A-B-C or C-B-A, in which A represents a sequence comprising at least two consecutively located locked nucleotide units, at least one of which is an alpha-L-oxy-LNA unit, and which sequence optionally contains one or more (such as 2, 3, 4 or 5) non-locked nucleotide units (such as deoxyribonucleotide units, ribonucleotide units or derivatives thereof) and/or optionally contains one or more (such as 2, 3, 4 or 5) locked nucleotide units, such as a unit selected from the group consisting of oxy-LNA, thio-LNA, amino-LNA (all in either alpha or beta configuration) and derivatives thereof;

B represents one nucleotide unit or a sequence of nucleotide units, with the proviso that at least one nucleotide unit in B has a 2'-deoxy-erythro-pentofuranosyl sugar moiety or a ribo-pentofuranosyl moiety; and C represents a sequence comprising at least two consecutively located locked nucleotide units, at least one of which is an alpha-L-oxy-LNA unit, and which sequence optionally contains one or more (such as 2, 3, 4 or 5) non-locked nucleotide units (such as deoxyribonucleotide units, ribonucleotide units or derivatives thereof) and/or optionally contains one or more (such as 2, 3, 4 or 5) locked nucleotide units, such as a unit selected from the group consisting of oxy-LNA, thio-LNA, amino-LNA (all in either alpha or beta configuration) and derivatives thereof. It is preferred that A has a length of 2-10 (preferably 2, 3, 4, 5, 6, 7, or 8) nucleotide units; B has a length of 1-10 (preferably 5, 6, 7, or 8) nucleotide units;

C has a length of 2-10 (preferably 2, 3, 4, 5, 6, 7, or 8) nucleotide units; so that the overall length of the construct is 8-30 (preferably 10, 11, 12, 13, 14, 15, 16, 17, 18, 19 or 20) nucleotide units.

An other interesting embodiment is a construct in which A represents a sequence of nucleotide units comprising at least three consecutively located locked nucleotide units, at least one of said locked nucleotide units being selected from the group consisting of alpha-L-oxy-LNA and derivatives thereof; C represents a sequence of nucleotide units comprising at least three consecutively located locked nucleotide units, at least one of said locked nucleotide units being selected from the group consisting of alpha-L-oxy-LNA and derivatives thereof; and/or B represents a sequence of least 2 nucleotide units (such as 3, 4, 5, 6, 7, 8, 9 or 10 units), which sequence in addition to the nucleotide unit(s) having 2'-deoxy-erythro-pentofuranosyl sugar moiety(ies) and/or ribo-pentofuranosyl moiety(ies), comprises nucleotide units which are selected independently from the group consisting of: locked nucleotide units (such as alpha-L-oxy-, -thio-, or -amino-nucleotide units) and derivatives thereof. Especially preferred is a construct in which A and C comprises at least one alpha-L-oxy-LNA or alpha-L-thio-LNA unit located adjacent to B.

In a further embodiment, the invention relates to an oligonucleotide which has the formula (in 5' to 3' order): A-B-C-D, in which A represents a sequence of locked nucleotide units; B represents a sequence of non-locked nucleotide units, preferably at least one unit has a 2'-deoxy pentofuranose sugar moiety, in which sequence 1 or 2 nucleotide units optionally are substituted with locked nucleotide units, preferably alpha-L-oxy-LNA; C represents a sequence of locked nucleotide units; and D represents a non-locked nucleotide unit or a sequence of non-locked nucleotide units. It is preferred that A has a length of 2-6 (preferably 3, 4 or 5) nucleotide units; B has a length of 4-12 (preferably 6, 7, 8, 9, 10 or 11) nucleotide units; C has a length of 1-5 (preferably 2, 3, or 4) nucleotide units; D has a length of 1-3 (preferably 1-2) nucleotide units; and that the overall length of the construct is 8-26 (preferably 12-21) nucleotide units. In presently preferred construct, A has a length of 4 nucleotide units; B has a length of 7-9, preferably 8, nucleotide units; C has a length of 3 nucleotide units; D has a length of 1 nucleotide unit; and the overall length of the construct is 15-17 (preferably 16) nucleotide units. It is further preferred that the locked nucleotide units in A and C are beta-D-oxy-LNA units or derivatives thereof.

The oligonucleotide constructs according to the invention can contain naturally occurring phosphordiester internucleoside linkages, as well as other internucleoside linkages as defined in this specification. Examples on internucleoside linkages are linkages selected from the group consisting of —O—P(O)$_2$—O—, —O—P(O,S)—O—, —O—P(S)$_2$—O—, —NR$^H$—P(O)$_2$—O—, —O—P(O,NR$^H$)—O—, —O—PO(R")—O—, —O—PO(CH$_3$)—O—, and —O—PO(NHR$^N$)—O—, where R$^H$ is selected form hydrogen and C$_{1-4}$-alkyl, and R" is selected from C$_{1-6}$-alkyl and phenyl.

In a further embodiment, the invention relates to an oligonucleotide construct which comprises at least one locked nucleotide unit selected from the group consisting of amino-LNA, thio-LNA (both in either alpha-L or beta-D configuration), alpha-L-oxy-LNA, and derivatives thereof; wherein at least one of the linkages between the nucleotide units is different from the natural occurring phosphordiester (—O—P(O)$_2$—O—) linker. Constructs in which the internucleoside linkage (between 3' carbon and 5' carbon on adjacent (3', 5' dideoxy) nucleosides) selected from the group consisting of: —O—P(O,S)—O—, —O—P(S)$_2$—O—, —NR$^H$—P(O)$_2$—O—, —O—P(O,NR$^H$)—O—, —O—PO(R")—O—, —O—PO(CH$_3$)—O—, and —O—PO(NHR$^N$)—O—, where R$^H$ is selected form hydrogen and C$_{1-4}$-alkyl, and R" is selected from C$_{1-6}$-alkyl and phenyl, is presently preferred, and the phoshorothioate internucleoside linkage is presently most preferred.

An embodiment of the oligonucleotide constructs according to the invention relates to such constructs that are able to mediate enzymatic inactivation (at least partly) of the target nucleic acid (eg. a RNA molecule) for the construct. Constructs that mediate RNase H cutting of the target are within the scope of the present invention. Thus, the present invention relates to constructs that are able to recruit RNase, especially constructs in which sequence B represents a sequence of nucleotide units that makes the construct able to recruit RNase H when hybridised to a target nucleic acid (such as RNA, mRNA).

It should be understood that the invention also relates to a pharmaceutical composition which comprises a least one antisense oligonucleotide construct of the invention as an active ingredient. It should be understood that the pharmaceutical composition according to the invention optionally comprises a pharmaceutical carrier, and that the pharmaceutical composition optionally comprises further antisense compounds, chemotherapeutic compounds, antiinflammatory compounds and/or antiviral compounds.

The pharmaceutical compositions of the present invention may be administered in a number of ways depending upon whether local or systemic treatment is desired and upon the area to be treated. Administration may be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, sprays, suppositories, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Compositions and formulations for oral administration include but is not restricted to powders or granules, microparticulates, nanoparticulates, suspensions or solutions in water or non-aqueous media, capsules, gel capsules, sachets, tablets or minitablets. Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels and suppositories. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

The antisense nucleotide constructs of the invention encompass, in their brodest scope, any pharmaceutically acceptable salts, esters, or salts of such esters. Furthermore encompasses the invention any other compound, which, upon administration to an animal or a human, is capable of directly or indirectly providing the biologically active metabolite or residue thereof. The invention therefore also encompasses prodrugs of the compounds of the invention and pharmaceutically acceptable salts of such prodrugs, and other bioequivalents. The term prodrug indicates a therapeutic agent that is prepared in an inactive form and that is converted to an active form, a drug, within the body or cells thereof. The pharmaceutically acceptable salts include but are not limited to salts formed with cations; acid addition salts formed with inorganic acids salts formed with organic acids such as, and salts formed from elemental anions.

In one embodiment, the present invention employs various penetration enhancers to effect the efficient delivery of nucleic acids, particularly oligonucleotides, to the skin of animals or humans. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Pharmaceutical compositions of the invention include a pharmaceutical carrier that may contain a variety of components that provide a variety of functions, including regulation of drug concentration, regulation of solubility, chemical stabilization, regulation of viscosity, absorption enhancement, regulation of pH, and the like. The pharmaceutical carrier may comprise a suitable liquid vehicle or excipient and an optional auxiliary additive or additives. The liquid vehicles and excipients are conventional and commercially available. Illustrative thereof are distilled water, physiological saline, aqueous solutions of dextrose, and the like. For water soluble formulations, the pharmaceutical composition preferably includes a buffer such as a phosphate buffer, or other organic acid salt. For formulations containing weakly soluble antisense compounds, micro-emulsions may be employed. Other components may include antioxidants, such as ascorbic acid, hydrophilic polymers, such as, monosaccharides, disaccharides, and other carbohydrates including cellulose or its derivatives, dextrins, chelating agents, and like components well known to those in the pharmaceutical sciences. The oligonucleotides may be encapsulated in liposomes for therapeutic delivery.

In a certain embodiment, the present invention provides pharmaceutical compositions containing (a) one or more antisense compounds and (b) one or more other chemotherapeutic agents which function by a non-antisense mechanism. When used with the compounds of the invention, such chemotherapeutic agents may be used individually (e.g., mithramycin and oligonucleotide), sequentially (e.g., mithramycin and oligonucleotide for a period of time followed by another agent and oligonucleotide), or in combination with one or more other such chemotherapeutic agents or in combination with radiotherapy.

Anti-inflammatory drugs, including but not limited to nonsteroidal anti-inflammatory drugs and corticosteroids, and antiviral drugs, may also be combined in compositions of the invention. Two or more combined compounds may be used together or sequentially.

In another embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially.

Dosing is dependent on severity and responsiveness of the disease state to be treated, and the course of treatment lasting from several days to several months, or until a cure is effected or a diminution of the disease state is achieved. Optimal dosing schedules can be calculated from measurements of drug accumulation in the body of the patient.

Optimum dosages may vary depending on the relative potency of individual oligonucleotides. Generally it can be estimated based on EC50s found to be effective in in vitro and in vivo animal models. In general, dosage is from 0.01 ug to 25 g per kg of body weight, and may be given once or more daily, weekly, monthly or yearly, or even once every 2 to 10 years. The repetition rates for dosing can be estimated based on measured residence times and concentrations of the drug in bodily fluids or tissues. Following successful treatment, it may be desirable to have the patient undergo maintenance therapy to prevent the recurrence of the disease state.

The LNA containing antisense compounds of the present invention can be utilized for diagnostics, therapeutics, prophylaxis and as research reagents and kits. For therapeutics, an animal or a human, suspected of having a disease or disorder, which can be treated by modulating the expression of a gene by administering antisense compounds in accordance with this invention. Further provided are methods of treating an animal and humans, suspected of having or being prone to a disease or condition, associated with expression of a target gene by administering a therapeutically or prophylactically effective amount of one or more of the antisense compounds or compositions of the invention. Examples of such a diseases are for example different types of cancer, infectious and inflammatory diseases.

In a certain embodiment, the present invention relates to a method of synthesis of a pharmaceutical compositions, a oligonucleotides or a construct according to the present invention.

Definitions

The term "nucleotide sequence" or "sequence" comprises a plurality (ie. more than one) nucleosides (or derivatives thereof), in which sequence each two adjacent nucleosides (or derivatives thereof) are linked by an internucleoside linker. When the length of a sequence are defined by a range (such as from 2-10 nucleotide units), the range are understood to comprise all integers in that range, i.e. "a sequence of 2-10 nucleotide units" comprises sequences having 2, 3, 4, 5, 6, 7, 8, 9, or 10 nucleotide units.

In the present context, the term "oligonucleotide" (or oligo, oligomer) means a successive chain of nucleoside units (i.e. glycosides of heterocyclic bases) connected via internucleoside linkages.

By the term "unit" is understood a monomer.

The term "at least one" comprises the integers larger than or equal to 1, such as 1, 2, 3, 4, 5, 6, 7, 8, 9, 10, 11, 12, 13, 14, 15, 16, 17 and so forth.

The term "locked nucleotide" comprises nucleotides in which the 2' deoxy ribose sugar moiety is modified by introduction of a structure containing a heteroatom bridging from the 2' to the 4' carbon atoms. The term includes nucleotides having the following substructures (the oxygen at the 3' and 5' ends illustrates examples of the starting point of the internucleoside linkages):
Beta-D-LNA Derivatives:

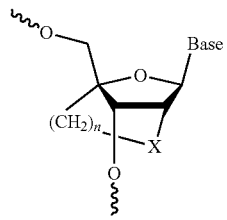

Alpha-L-LNA Derivatives

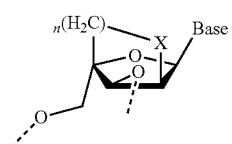

In both structures, X represents O, S or N—R (R=H; C1-C6 alkyl such as methyl, ethyl, propyl, i-propyl, butyl, i-butyl, t-butyl and pentyl); and n is an integer 1, 2 or 3, so that the group —(CH2)n- comprises methylen, ethylen or propylen groups. In these alkylene groups (and the —N(C1-C6 alkyl)- group), one or more H atoms can be replaced with substituents, such as one or more substituents selected from the group consisting of halogen atoms (Cl, F, Br, I), Nitro, C1-6 alkyl or C1-6 alkoxy, both optionally halogenated.

In the present context, the term "$C_{1-6}$-alkyl" means a linear, cyclic or branched hydrocarbon group having 1 to 6 carbon atoms, such as methyl, ethyl, propyl, iso-propyl, butyl, tert-butyl, iso-butyl, pentyl, cyclopentyl, hexyl, cyclohexyl, in particular methyl, ethyl, propyl, iso-propyl, tert-butyl, iso-butyl and cyclohexyl. "$C_{1-6}$-alkoxy" means —O—(C1-6-alkyl).

The term "non-locked nucleotide" comprises nucleotides that do not contain a bridging structure in the ribose sugar moiety. Thus, the term comprises DNA and RNA nucleotide monomers (phosphorylated adenosine, guanosine, uridine, cytidine, deoxyadenosine, deoxyguanosine, deoxythymidine, deoxycytidine) and derivatives thereof as well as other nucleotides having a 2'-deoxy-erythro-pentofuranosyl sugar moiety or a ribo-pentofuranosyl moiety.

The term "thio-LNA" comprises a locked nucleotide in which X in the above formulas represents S, and n is 1. Thio-LNA can be in both beta-D and alpha-L-configuration.

The term "amino-LNA" comprises a locked nucleotide in which X in the above formulas represents —NR—, and n is 1. Amino-LNA can be in both beta-D and alpha-L-configuration.

The term "oxy-LNA" comprises a locked nucleotide in which X in the above formulas represents O and n is 1. Oxy-LNA can be in both beta-D and alpha-L-configuration.

By the term "alpha-L-LNA" as used herein is normally understood alpha-L-oxy-LNA (n=1 in the bridging group), and by the term "LNA" as used herein is understood beta-D-oxy-LNA monomer wherein n in the bridging group is 1.

However, derivatives of the above locked LNA's comprise nucleotides in which n is an other integer than 1.

By the term "derivatives thereof" in connection with nucleotides (e.g. LNA and derivatives thereof) is understood that the nucleotide, in addition to the bridging of the furan ring, can be further derivatized. For example, the base of the nucleotide, in addition to adenine, guanine, cytosine, uracil and thymine, can be a derivative thereof, or the base can be substituted with other bases. Such bases includes heterocyclic analogues and tautomers thereof. Illustrative examples of nucleobases are xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynylcytosine, 5-fluorouracil, 5-bromouracil, pseudoisocytosine, 2-hydroxy-5-methyl-4-triazolopyridin, isocytosine, isoguanin, inosine, $N^6$-alylpurines, $N^6$-acylpurines, $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^4$-alkylpyrimidines, $N^4$-acylpyrimidines, $N^4$-benzylpurine, $N^4$-halopyrimidines, $N^4$-vinylpyrimidines, $N^4$-acetylenic pyrimidines, $N^4$-acyl pyrimidines, $N^4$-hydroxyalkyl pyrimidines, $N^6$-thioalkyl pyrimidines, thymine, cytosine, 6-azapyrimidine, including 6-azacytosine, 2- and/or 4-mercaptopyrimidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimdine, $N^2$-alkylpurines, $N^2$-alkyl-6-thiopurines, 5-azacytidinyl, 5-azauracilyl, trazolopyridinyl, imidazolopyridinyl, pyrrolopyrimidinyl, and pyrazolopyrimidinyl. Functional oxygen and nitrogen groups on the base can be protected as necessary or desired. Suitable protecting groups are well known to those skilled in the art, and included trimethylsilyl, dimethylhexylsilyl, t-butyldimenthylsilyl, and t-butyldiphenylsilyl, trityl, alkyl groups, acyl groups such as acetyl and propionyl, methanesulfonyl, and p-toluenesulfonyl. Preferred bases include cytosine, methyl cytosine, uracil, thymine, adenine and guanine. In addition to the derivatisation of the base, both locked and non-locked nucleotides can be derivatised on the ribose moiety. For example, a 2' substituent can be introduced, such as a substituent selected from the group consisting of halogen (such as fluor), C1-C9 alkoxy (such as methoxy, ethoxy, n-propoxy or i-propoxy), C1-C9 aminoalkoxy (such as aminomethoxy and aminoethoxy), allyloxy, imidazolealkoxy, and polyethyleneglycol, or a 5' substituent (such as a substituent as defined above for the 2' position) can be introduced.

By the terms "internucleoside linkage" and "linkage between the nucleotide units" (which is used interchangeably) are to be understood the divalent linker group that forms the covalent linking of two adjacent nucleosides, between the 3' carbon atom on the first nucleoside and the 5' carbon atom on the second nucleoside (said nucleosides being 3', 5' dideoxy). The oligonucleotides of the present invention comprises sequences in which both locked and non-locked nucleotides independently can be derivatised on the internucleoside linkage which is a linkage consisting of preferably 2 to 4 groups/atoms selected from —$CH_2$—, —O—, —S—, —$NR^H$—, >C=O, >C=$NR^H$, >C=S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where $R^H$ is selected form hydrogen and $C_{1-6}$-alkyl, and R" is selected from $C_{1-6}$-alkyl and phenyl. Illustrative examples of such internucleoside linkages are —$CH_2$—$CH_2$—$CH_2$—, —$CH_2$—CO—$CH_2$—, —$CH_2$—CHOH—$CH_2$—, —O—$CH_2$—, —O—$CH_2$—$CH_2$—, —O—$CH_2$—CH(R5)-, —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—, —O—CO, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N(R5)-, —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH(R5)-, —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—SO$_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$—, —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHR$^N$)—O—, —O—P(O)$_2$—$NR^H$—, —$NR^H$—P(O)$_2$—O—, —O—P(O,$NR^H$)—O—, —$CH_2$—P(O)$_2$—O—, —O—P(O)$_2$—$CH_2$—, and —O—Si(R")$_2$—O—; where R5 is selected from hydrogen and $C_{1-6}$-alkyl, $R^H$ is selected form hydrogen and $C_{1-6}$-alkyl, and R" is selected from $C_{1-6}$-alkyl and phenyl. —$CH_2$—CO—$NR^H$—, —$CH_2$—$NR^H$—O—, —S—$CH_2$—O—, —O—P(O)$_2$—O—, —O—P(O,S)O—, —O—P(S)$_2$—O—, —$NR^H$—P(O)$_2$—O—, —O—P(O,$NR^H$)—O—, —O—PO(R")—O—, —O—PO(CH$_3$)—O—, and —O—PO(NHR$^N$)—O—, where $R^H$ is selected from hydrogen and $C_{1-6}$-alkyl, and R" is selected from $C_{1-6}$-alkyl and phenyl, are especially preferred.

The nucleotides units may also contain a 3'-Terminal group or a 5'-terminal group, preferably —OH.

By the term "able to recruit RNase H" is understood that the an oligonucleotide construct, in order to elicit RNase H enzyme cleavage of a target nucleic acid (such as target mRNA), must include a segment or subsequence that is of DNA type. This means that at least some nucleotide units of the oligonucleotide construct (or a subsequence thereof) must have 2'-deoxy-erythro-pentofuranosyl sugar moieties. A subsequence having more than three consecutive, linked 2'-deoxy-erythro-pentofuranosyl containing nucleotide units likely is necessary in order to elicit RNase H activity upon hybridisation of an oligonucleotide construct of the invention with a target nucleic acid, such as a RNA. Preferably, a sequence which is able to recruit RNase H contains more than three consecutively located nucleotides having 2'-deoxy-erythro-pentofuranosyl sugar moieties, such as 4, 5, 6, 7, 8 or more units. However, such a subsequence of consecutively located nucleotides having 2'-deoxy-erythro-pentofuranosyl sugar moieties can by spiked (ie. one or more (such as 1, 2, 3, 4, or more) nucleotides being replaced) with other nucleotides, preferably alpha-L-oxy, thio- or amino-LNA units or derivatives thereof.

The term "pharmaceutically acceptable salt" is well known to the person skilled in the art.

Examples of such pharmaceutically acceptable salts are the iodide, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, g-hydroxybutyrate, b-hydroxybutyrate, butyne-1,4-dioate, hexyne-1,4-dioate, hexyne-1,6-dioate, caproate, caprylate, chloride, cinnamate, citrate, decanoate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, propanesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

Experimental

Oligonucleotide Synthesis

Oligonucleotides were synthesized using the phosphoramidite approach on an Expedite 8900/MOSS synthesizer (Multiple Olionucleotide Synthesis System) at 1 μM scale. At the end of the synthesis (DMT-on) the oligonucleotides were cleaved from the solid support using aqueous ammonia for 1 h at room temperature, and further deprotected for 4 h at 65° C. The crudes were purified by reverse phase HPLC. After the removal of the DMT-group, the oligonucleotides were characterized by AE-HPLC or RP-HPLC, and the structure further confirmed by ESI.

3'-Exonuclease Stability Study

Snake venom phosphodiesterase (SVPD, Amersham Pharmacia) assays were performed using 26 µg/mL oligonucleotide, 0.3 µg/mL enzyme at 37° C. in a buffer of 50 mM Tris-HCl, 10 mM $MgCl_2$, pH 8. The enzyme was shown to maintain its activity under these conditions for at least 2 h. Aliquots of the enzymatic digestion were removed at the indicated times, quenched by heat denaturation for 3 min and stored at −20° C. until analysis by RP-HPLC.

S1—Endonuclease Stability Study

S1 endonuclease (Amersham Pharmacia) assays were performed using 1.5 µmol oligonucleotide and 16 U/mL enzyme at 37° C. in a buffer of 30 mM NaOAc, 100 mM NaCl, 1 mM $ZnSO_4$, pH 4.6. The enzyme was shown to maintain its activity under these conditions for at least 2 h. Aliquots of the enzymatic digestion were removed at the indicated times, quenched by freezing-drying, and stored at −20° C. until analysis by either RP-HPLC and ES-MS or polyacrylamide electrophoresis.

Luciferase Assay

The X1/5 Hela cell line (ECACC Ref. No: 95051229), which is stably transfected with a "tet-off" luciferase system, was used. In the absence of tetracycline the luciferase gene is expressed constitutively. The expression can be measured as light in a luminometer, when the luciferase substrate, luciferin has been added.

The X1/5 Hela cell line was grown in Minimun Essential Medium Eagle (Sigma M2279) supplemented with 1× Non Essential Amino Acid (Sigma M7145), 1× Glutamax I (Invitrogen 35050-038), 10% FBS calf serum, 25 µg/ml Gentamicin (Sigma G1397), 500 µg/ml G418 (Invitrogen 10131-027) and 300 µg/ml Hygromycin B (invitrogen 10687-010). The X1/5 Hela cells were seeded at a density of 8000 cells per well in a white 96 well plate (Nunc 136101) the day before the transfection. Before the transfection, the cells were washed one time with OptiMEM (Invitrogen) followed by addition of 40 µl of OptiMEM with 2 µg/ml of Lipofectamine2000 (Invitrogen). The cells were incubated for 7 minutes before addition of the oligonucleotides. 10 µl of oligonucleotide solutions were added and the cells were incubated for 4 hours at 37° C. and 5% $CO_2$. After the 4 hours of incubation the cells were washed once in OptiMEM and growth medium was added (100 µl). The luciferase expression was measure the next day.

Luciferase expression was measured with the Steady-Glo luciferase assay system from Promega. 100 µl of the Steady-Glo reagent was added to each well and the plate was shaken for 30 s at 700 rpm. The plate was read in Luminoskan Ascent instrument from ThermoLabsystems after 8 min of incubation to complete total lysis of the cells. The luciferase expression is measured as Relative Light Units per seconds (RLU/s). The data was processed in the Ascent software (v2.6) and graphs were drawn in SigmaPlot2001.

RNaseH Assay 25 nM RNA was incubated in the presence of a 10-fold excess of various complementary oligonucleotides in 1×TMK-glutamate buffer (20 mM Tris acetate, 10 mM magnesium acetate and 200 mM potassium glutamate, pH 7.25) supplied with 1 mM DTT in a reaction volume of 40 µl. The reactions were preincubated for 3 minutes at 65° C. followed by 15 minutes at 37° C. before addition of RNase H (Promega, Cat.#4285). 0.2 U of RNase H was added, and samples were withdrawn (6 µl) to formamide dye (3 µl) on ice at the time points 0, 10, 20 and 30 minutes after RNase H addition. 3 µl of the 0, 10, 20 and 30 minutes samples were loaded on a 15% polyacrylamide gel containing 6M urea and 0.9× Tris borate/EDTA buffer. The gel was 0.4 mm thick and ran at 35 watt as the limiting parameter for 2 hours. The gel was dried for 60 minutes at 80° C., followed by ON exposure on Kodak phosphorscreen. The Kodak phosphorscreen was read in a Bio-Rad FX instrument and the result was analysed in Bio-Rad software Quantity One.

Cellular Assay: Luciferase Target

Cell Culture: Cell lines 15PC3 (human prostate cancer) and X1/5 (HeLa cells stably transfected with a Tet-Off luciferase construct) were used, 15PC3 were kindly donated by F. Baas, Neurozintuigen lab, Amsterdam, The Netherlands, X1/5 were purchased from ECACC. 15PC3 were maintained in DMEM+10% FCS+glutamax+gentamicin and X1/5 were maintained in DMEM+10% FCS+glutamax+gentamicin+hygromycin+G418 and both cell lines were passaged twice weekly.

Transfection: Cells were seeded at 150000 cells pr. well in 12-well plates the day before transfection. For transfection with lipid, Lipofectamine 2000 (GIBCO BRL) was mixed with OptiMem and 300 µl of the mixture was added to each well and incubated for 7 min. before addition of 100 µl oligo diluted in OptiMem. For each cell line, the optimal Lipofectamine 2000 was determined, for X1/5, the optimal Lipofectamine concentration was 2 µg/ml and for 15PC3 the optimal concentration was 10 µg/ml.

For transfection without lipid, the cells were washed in OptiMem (GIBCO BRL) and 300 µl OptiMem was added to each well. Working stocks of 200 µM were prepared of each oligonucleotide to be tested and added to each well obtaining the desired concentration. For mock controls, oligonucleotide was substituted with water in both protocols.

The cells were incubated with the oligonucleotide for 4 h at 37° C. and 5% $CO_2$ in a humidified atmosphere and subsequently washed in OptiMem before complete growth medium was added. The cells were incubated for an additional 20 h.

For FACS analysis, cells were harvested by trypsination and washed twice in Cell Wash (BD) and resuspended in 1× Cell Fix (BD).

FACS analysis: FACS analysis was performed on a FACSCalibur (BD), settings were adjusted on mock controls. Data analysis was performed using the Cell Quest Pro software (BD).

Assisted Cellular Uptake

Transfections were performed in 6 well culture plates on microscope glass coverslips with FAM-labeled oligonucleotides at 400 nM. Transfections were done with either DAC30 (Eurogentec) or Lipofectamine 2000 as liposomal transfection agents for 5 h in serum free DMEM at 37° C. Immediately after the transfection period, the cells were washed with PBS and fixed with 4% paraformaldehyde.

Cell Lines: Ha-Ras Target

Prostate cancer cell line 15PC3 and pancreatic carcinoma cell line MiaPacaII were maintained by serial passage in Dulbecco's modified Eagle's medium (DMEM). Cells were grown at 37° C. and 5% $CO_2$. Media were supplemented with 10% fetal calf serum, 2 mM L-glutamine, 100 U/mL penicillin and 100 µg/mL streptomycin.

Transfections: Ha-Ras Target

Cell transfections were performed with 15PC3 cells plated in 6 well culture plates. The cells were plated (70% confluent) the day before transfection. The transfections were usually performed using lipofectamine 2000 (Invitrogen) according to the manufacturer's instructions, except for using serum free DMEM. Cells were transfected for 5 hours. Afterwards the medium was replaced with fresh DMEM. We also compared Lipofectamine 2000 with DAC30 (Eurogentec). When DAC30 was used the protocol described in Ten Asbroek et al. (NAR 28, 1133-1138) was followed.

For Fluorescence studies the cells were plated on glass cover slips in 6 well culture plates. Transfections were performed as described above but using FAM labeled oligonucleotides. At the time of analysis, the cells were fixed on the glass in 4% paraformaldehyde and sealed on microscope glass in Vectashield mounting medium (Vector Laboratories Inc.). Fluorescence microscopy was done with a Vanox Microscope and appropriate filtres.

mRNA Analysis: Ha-Ras Target

After 20 hours the cells were harvested in TRIZOL (Invitrogen), 1 ml per well. The RNA was isolated according to the manufacturer's instructions for TRIZOL. The RNA was separated on glyoxal gels containing 1% agarose following standard protocols. RNA was subsequently blotted onto Hybond N+ membrane (Amersham) in 20×SSC. After the transfer, the RNA was UV cross-linked, and then the membrane was baked for 2 hours at 80° C. Hybridizations and post-hybridization washes were done according to Church and Gilbert (PNAS 81, 1991-1995). The Ha-Ras probe used was generated using Ha-Ras primers according to Sharpe et al. (J. AM. Soc. Nephrol. 11 1600-1606) cloned into pGEM-T Easy vector (Promega). The loadings of the Ha-Ras mRNA levels were corrected by using a 28S probe as described in Ten Asbroek et al. (NAR 28, 1133-1138).

Biodistribution Studies

The animal experiments were approved by the ethical committee and are registered under No. DNL19.

Tritium labeling of oligonucleotides was performed using the heat exchange method described by Graham et al. (Graham, M. J., Freier, S. M., Crooke, R. M., Ecker, D. J., Maslova, R. N., and Lesnik, E. A. (1993). Tritium labeling of antisense oligonucleotides was carried out by exchange with tritiated water. *Nucleic Acids Res.*, 21: 3737-3743). The only two introduced differences to the protocol were that only 1 mg was labeled per oligonucleotide and that the separation of free tritium from the labeled oligonucleotide was done by 3× G10 30 cm Sephadex columns (the columns were made using 10 ml plastic pipettes). Radioactivity in all samples was counted after dissolving the samples in Ultima Gold (Packard) scintillation fluid, and using a scintillation counter.

For the biodstribution studies, female nude mice (NMRI nu/nu, Charles River Netherlands, Maastricht, The Netherlands) with 15PC3 and MiapacaII xenografts were used. See the in vivo experiment section for further details.

Tissue distribution studies of tritiated oligonucleotides were performed according to Bijsterbosch et al. (Bijsterbosch, M. K., Manoharan, M., Rump, E. T., De Vrueh, R. L., van Veghel, R., Tivel, K. L., Biessen, E. A., Bennett, C. F., Cook, P. D., and van Berkel T. J. (1997) In vivo fate of phosphorothioate antisense oligodeoxynucleotides: predominant uptake by scavenger receptors on endothelial liver cells. *Nucleic Acids Res.*, 25: 3290-3296). The radioactivity in the different organs was corrected for serum present at the time of sampling as determined by the distribution of $^{125}$I-BSA (personal communication K. Kruijt, University of Leiden, the Netherlands).

The oligonucleotides were either administrated by bolus injection in the lower vena cava (circulation for 30 minutes) or using Alzet osmotic minipumps (see in vivo experiment section), for a prolonged systemic circulation. Tissue samples were dissolved in 5 M NaOH at 65° C. and subsequently mixed with 10 volumes of Ultima Gold scintillation fluid. Serum and urine can be counted by mixing directly with Ultima gold.

In Vivo Experiment

The animal experiments were approved by the ethical committee and are registered under No. DNL19. The detailed protocols of the animal studies are described in two publications: Tumor genotype-specific growth inhibition in vivo by antisense oligonucleotides against a polymorphic site of the large subunit of human RNA polymerase II. Fluiter K, ten Asbroek A L, van Groenigen M, Nooij M, Aalders M C, Baas F. Cancer Res 2002 Apr. 1; 62(7):2024-2028

In vivo tumor growth inhibition and biodistribution studies of locked nucleic acid (LNA) antisense oligonucleotides. Fluiter K, ten Asbroek A L, de Wissel M B, Jakobs M E, Wissenbach M, Olsson H, Olsen O, Oerum H, Baas F. Nucleic Acids Res 2003 Feb. 1; 31(3):953-962

Mice: Female NMRI nu/nu (Charles River Netherlands, Maastricht, The Netherlands). Xenografts: MiaPaca II injected in the right flank s.c. with Matrigel (collaborative biomedical products Bedford, Mass.); 15PC3 injected in the left flank s.c. with Matrigel. Osmotic pumps: Alzet 1002 (DURECT Corporation, Cupertino, Calif.) lot no. 10045-02 Dosage for 2776, 2778 (alpha-L-oxy-LNA), 2742 and 2744 (beta-D-oxy-LNA): 1 and 2.5 mg/kg/day. Control: physiological saline.

Temperature and animal ID was monitored using: ELAM chips (IPTT 200) using a DAS 5002 chip reader (BMDS, Seaford, Del.).

Serum samples were taken for ASAT/ALAT and Alkaline Phosphatase determination. Aspartate aminotransferase (ASAT) and alanine aminotransferase (ALAT) levels and alkaline phosphatase in serum were determined using standard diagnostic procedures with the H747 (Hitachi/Roche) with the appropriate kits (Roche Diagnostics). The ALAT/ASAT and Alkaline phosphatase Levels were determined approx 20 hours post extraction of serum from the animal.

Results

Beta-D-Amino-LNA

Nuclease Stability

One of the major difficulties encountered using the naturally occurring phosphodiester oligonucleotides as antisense probes is their rapid degradation by various nucleolytic activities in cells, serum, tissues or culture medium. Since the phosphorus center is the site of nucleolytic attack, many modifications have been introduced in the internucleoside linkage to prevent enzymatic degradation. To date, the most commonly employed synthetic modification is the backbone phosphorothioate analogue, made by replacing one of the non-bridging oxygen atoms of the internucleoside linkage by sulfur.

We wanted to evaluate the effect of introducing the novel LNA within an oligonucleotide in the presence of nucleases, and to compare it with the well-studied phosphorothioate oligonucleotides. The study was carried out with oligothymidylates by blocking the 3'-end with the novel LNA relatives. The oligonucleotide is synthesized on deoxynucleoside-support (t).

From FIG. 1, we can appreciate the stability properties, which confer beta-D-amino-LNA. Oligonucleotides containing T-monomer of 2'-beta-D-amino-LNA ($T^N$) present a remarkable stability against a 3'-exonuclease. Blocking the 3'-end with just two $T^N$ stops the enzyme from degrading the oligonucleotide at least for 2 h. See FIG. 1.

Assisted Cellular Uptake and Subcellular Distribution

The uptake efficiency of FAM-labeled oligonucleotide containing beta-D-amino-LNA was measured as the mean fluorescence intensity of the transfected cells by FACS analysis. Two different transfection agents were tested (Lipofectamine 2000 and DAC30) in two different cell lines (MiaPacaII and 15PC3).

TABLE 1

Oligonucleotides (SEQ ID NOS 1-3, respectively, in order of appearance) containing beta-D-amino-LNA used in cellular uptake and subcellular distribution experiments. Residue c is metilyl-c both for DNA and LNA.

| Ref | oligonucleotides | DAC30 | | Lipofectamine 2000 | |
|---|---|---|---|---|---|
| | | % cells | % uptake | % cells | % uptake |
| 2753 | $T^N C^N C^N g_s t_s c_s a_s t_s c_s g_s c_s t_s C^N C^N T^N c$-FAM | — | — | 100 | 100 |
| 2752 | $T^N_s C^N_s C^N_s g_s t_s c_s a_s t_s c_s g_s c_s t_s C^N_s C^N_s T^N_s c$-FAM | 30 | 30 | 100 | 100 |
| 2740 | $T_s C_s C_s g_s t_s c_s a_s t_s c_s g_s c_s t_s C_s C_s T_s c$-FAM | 80 | 30 | 100 | 100 |

Oligonucleotides both fully thiolated (PS, 2752) and partially thiolated (PO in the flanks and PS in the gap, 2753) containing beta-D-amino-LNA listed in table 1 were transfected with good efficiency, see table 1. Both transfection agents, DAC30 and Lipofectamine, presented good transfection efficiency; however, Lipofectamine was superior.

Lipofectamine showed 100% efficiency in all cases: for both oligonucleotides (2753 and 2752) and in both cell lines. Moreover, no significant differences in assisted transfection efficiency were observed between 2752 and 2753.

The FAM-labeled oligonucleotide 2752 was also used to assay the subcellular distribution of oligonucleotides containing beta-D-amino-LNA, see FIG. 2. Most of the staining was detected as nuclear fluorescence that appeared as bright spherical structures (the nucleoli is also stained) in a diffuse nucleoplasmic background, as well as some cytoplasmic staining in bright punctate structures. The observed distribution patterns were similar for 15PC3 and MiaPacaII.

The subcellular distribution of beta-D-amino-LNA was comparable to the one observed with beta-D-oxy-LNA, 2740.

Figure 3A:
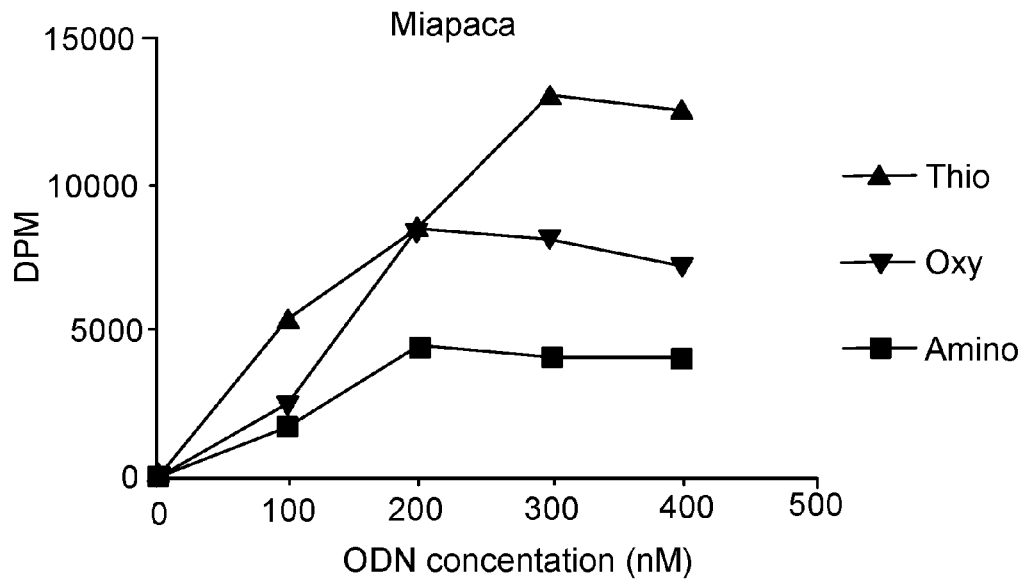
FIG. 3A: Uptake of titriated oligonucleotides (thio=2748; amino=2754; oxy=2742) in MiaPacaII cells at different oligonucleotide concentration with Lipofectamine2000 as transfection agent.
Figure 3B:
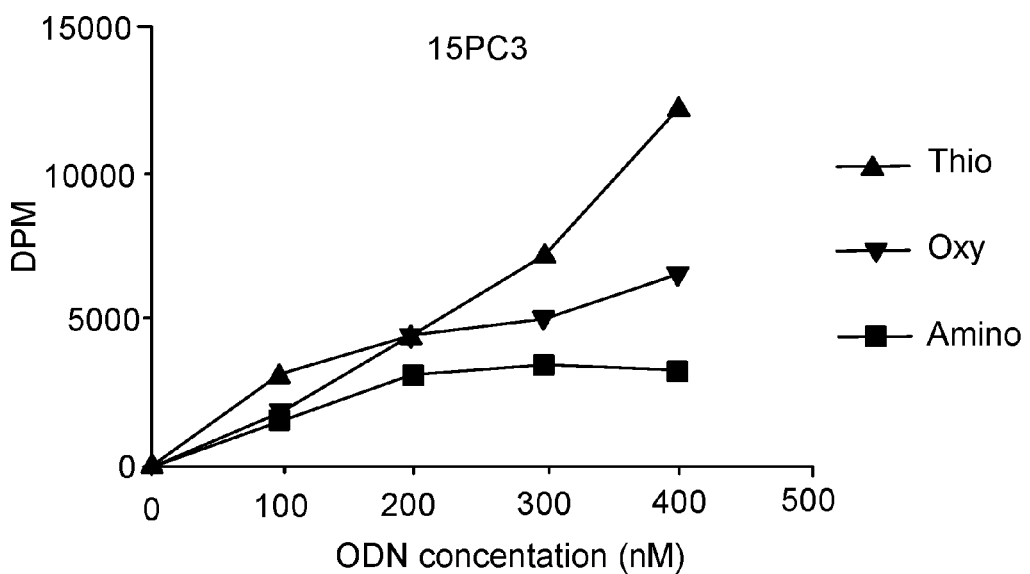
FIG. 3B: Uptake of titriated oligonucleotides (thio=2748; amino=2754; oxy=2742) in 15PC3 cells at different oligonucleotide concentration with Lipofectamine2000 as transfection agent.

The uptake efficiency was also measured with tritium-labeled oligonucleotide 2754 (see table 3 and FIG. 3) at different concentrations 100, 200, 300 and 400 nM, using Lipofectamine2000 as transfection agent, both in MiaPacaII and 15PC3 cells, and compared with the equivalent beta-D-oxy-LNA, 2742 (see table 3). 2754 shows lower uptake than 2742.

Antisense Activity Assay: Luciferase Target

It has been shown that beta-D-oxy-LNA does not elicit RNaseH activity, which is the most common mode of action for an antisense oligonucleotide targeting the down-stream region of the mRNA. However, this disadvantage can be overcome by creating chimeric oligonucleotides composed of beta-D-oxy-LNA and a DNA gap positioned in the middle of the sequence. A gapmer is based on a central stretch of 4-12 DNA (gap) typically flanked by 1 to 6 residues of 2'-O modified nucleotides (beta-D-oxy-LNA in our case, flanks). It was of our interest to evaluate the antisense activity of oligonucleotides, which contain beta-D-amino-LNA in a gapmer design, and compare them with beta-D-oxy-LNA/DNA gapmers.

The oligonucleotides from table 2 were prepared. We decided to carry out the study with gapmers of 16 nt in length and a gap of 7 nt, which contain 4 residues of beta-D-amino-LNA in one flank and 4 residues of beta-D-oxy-LNA in the other flank, and a thiolated gap. The FAM group was shown not to affect the antisense ability of the oligonucleotides. Therefore, we prepared a FAM-labelled oligonucleotide to be both tested in the Luciferase assay, and in the Cellular uptake (unassisted).

The oligonucleotide, which targets a motif of the mRNA of the Firefly Luciferase, contains two mismatches in the flanks. Two C residues of the 5'-end LNA flank were substituted for two Ts for synthetic reasons. At that point in time, only the T residues were available. Therefore and in order to be able to establish a correct comparison, the corresponding beta-D-oxy-LNA control was also included in the assay. No FAM labeling was necessary in this case.

TABLE 2

Oligonucleotide (SEQ ID NOS. 4-5, respectively, in order of appearance) containing beta-D-amino-LNA used in the antisense activity assay and the oxy-LNA control (Capital letters for LNA and small letters for DNA, $T^N$ is beta-D-amino-LNA). Residue c is methyl-c both for LNA.

| ref | sequence | design | size |
|---|---|---|---|
| U-14 | FAM-$T^N T^N T^N T^N g_s t_s c_s a_s t_s c_s g_s$TCTTT | Amino-LNA in one flank/PS gap of 7 | 16 mer |
| 2023-m; 02579 | TTTT$g_s t_s c_s a_s t_s c_s g_s$TCTTT | Control with oxy-LNA | 16 mer |

Figure 4:
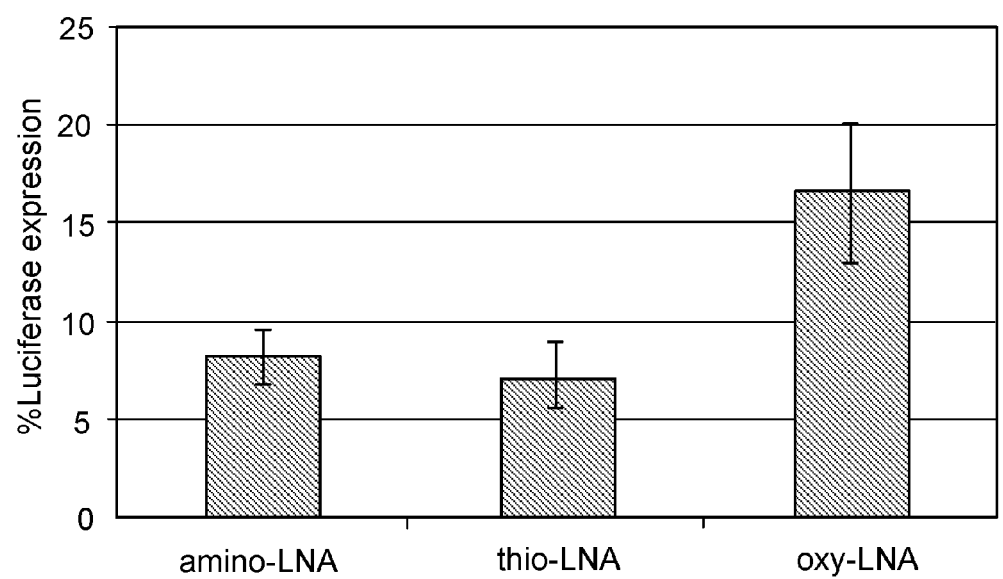
FIG. 4: Down-regulation of Luciferase expression of oligonucleotides gapmers containing beta-D-amino-LNA or beta-D-thio-LNA and the corresponding beta-D-oxy-LNA gapmer control at 50 nM oligonucleotide concentration.

From FIG. 4, we can see that the oligonucleotide with beta-D-amino-LNA presents good antisense activity at 50 nM oligonucleotide concentration. The inclusion of beta-D- amino-LNA in the flanks of an oligonucleotide results in good down-regulation. We can conclude that the antisense activity of an oligonucleotide containing beta-D-amino-LNA is at least as good as the parent all beta-D-oxy-LNA gapmer.

Antisense Activity Assay: Ha-Ras Target

It was of our interest to further evaluate the antisense activity of oligonucleotides containing beta-D-amino-LNA in a gapmer design, and compare them with beta-D-oxy-LNA gapmers.

The oligonucleotides from table 3 were prepared. We decided to carry out the study with oligonucleotides of 16 nt in length and a gap of 8 nt, which contain 3 residues of beta-D-amino-LNA in each flank and a different extent of thiolation. 2754 is fully thiolated (PS), while 2755 is only thiolated in the gap (PO in the flanks and PS in the gap). The oligonucleotides were designed to target a motif of the mRNA of Ha-Ras. Different mismatch controls were also included, 2756 is fully thiolated and 2757 presents thiolation only in the gap, see table 3. Moreover, the corresponding beta-D-oxy-LNA gapmers (see table 3, 2742 is all PS, 2744 is the corresponding mismatch control; 2743 has PS in the gap, 2745 is the corresponding mismatch control) were also tested.

TABLE 3

Oligonucleotides (SEQ ID NOS 6-13, respectively, in order of appearance) containing beta-D-amino-LNA and beta-D-oxy-LNA used in the antisense activity experiments. Residue c is methyl-c both for DNA and LNA.

| ref | oligonucleotides | |
|---|---|---|
| 2755 | $T^NC^NC^Ng_sc_sa_st_sc_sg_sc_st_sC^NC^NT^Nc$ | PO/PS |
| 2754 | $T^N_sC^N_sC^N_sg_sc_sa_st_sc_sg_sc_st_sC^N_sC^N_sT^N_sc$ | All PS |
| 2743 | $TCCg_st_sc_sa_st_sc_sg_sc_st_sCCTc$ | PO/PS |
| 2742 | $T_sC_sC_sg_st_sc_sa_st_sc_sg_sc_st_sC_sC_sT_sc$ | All PS |
| 2757 | $T^NC^NT^Ng_st_sa_sa_st_sa_sg_sc_sc_sC^NC^NC^Nc$ | Mismatch control |
| 2756 | $T^N_sC^N_sT^N_sg_st_sa_sa_st_sa_sg_sc_sc_sc_sC^N_sC^N_sC^N_sc$ | Mismatch control |
| 2745 | $TCTg_st_sa_sa_st_sa_sg_sc_sc_sCCCc$ | Mismatch control |
| 2744 | $T_sC_sT_sg_st_sa_sa_st_sa_sg_sc_sc_sC_sC_sC_sc$ | Mismatch control |

The Ras family of mammalian proto-oncogenes includes three well-known isoforms termed Ha-Ras (Ha-Ras), Ki-Ras (K-Ras) and N-Ras. The ras proto-oncogenes encode a group of plasma membrane associated G-proteins that bind guanine nucleotides with high affinity and activates several effectors including raf-1, PI3-K etc. that are known to activate several distinct signaling cascades involved in the regulation of cellular survival, proliferation and differentiation.

Several in vitro (and in vivo) studies have demonstrated that the Ras family of proto-oncogenes are involved in the induction of malignant transformation. Consequently, the Ras family is regarded as important targets in development of anticancer drugs, and it has been found that the Ras proteins are either over-expressed or mutated (often leading to constitutive active Ras proteins) in approximately 25% of all human cancers.

Interestingly, the ras gene mutations in most cancer types are frequently limited to only one of the ras genes and are dependent on tumor type and tissue. Mutations in the Ha-Ras gene are mainly restricted to urinary tract and bladder cancer.

The inclusion of beta-D-amino-LNA in the flanks of an oligonucleotide results in good down-regulation levels. From FIG. 5, we can see that oligonucleotides with beta-D-amino-LNA present good antisense activity at two different concentrations, 400 and 800 nM. No significant difference in down-regulation can be seen between oligonucleotides 2755 and 2754, which present a different degree in thiolation. We can conclude that the antisense activity of an oligonucleotide containing beta-D-amino-LNA is at least as good as the parent beta-D-oxy-LNA gapmer. From FIG. 6, a wider range of concentration was tested. There is a potent down-regulation between 50-400 nM for 2754. The specificity was also tested; at 30 nM there is a significant difference in down-regulation between the mismatch 2756 (less potent) and the match 2754. Lower concentrations (5-40 nM) were also included from the table in FIG. 6. Potent down-regulation is observed even at 5 nM for 2754, and these levels of down-regulation are comparable to the corresponding beta-D-LNA control, 2742. The specificity is also remarkable, if we compare the antisense activity for 2754 at 20 nM (8.7% down-regulation) in comparison with the mismatch containing control 2756 (56.2% down-regulation).

Biodistribution

The biodistribution of oligonucleotides containing beta-D-amino-LNA (tritiated 2754) was also studied, both after i.v. injection and using Alzet osmotic minipumps. 2754 was administered to xenografted mice with 15PC3 tumors on the left side and MiaPacaII tumors on the right side as an intraveneous injection, and the analysis was carried out after 30 min circulation. From FIG. 7, the serum clearance for 2754 is very rapid, and the biodistribution looks very similar to the biodistribution pattern presented by the reference containing beta-D-oxy-LNA; the kidney and the liver (to lesser extent) are the main sites of uptake, when corrected for tissue weight.

Figure 8A:
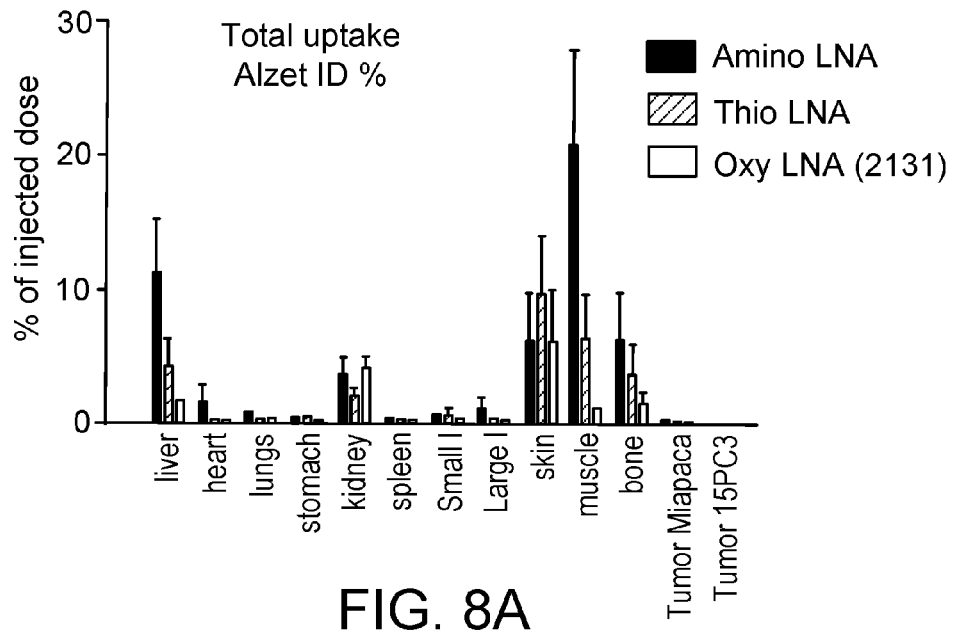
FIG. 8A: Total uptake of titriated 2754=amino, 2748=thio and 2742=oxy after 14 days of continuous administration at a 2.5 mg/Kg/day dosage using Alzet osmotic minipumps.
Figure 8B:
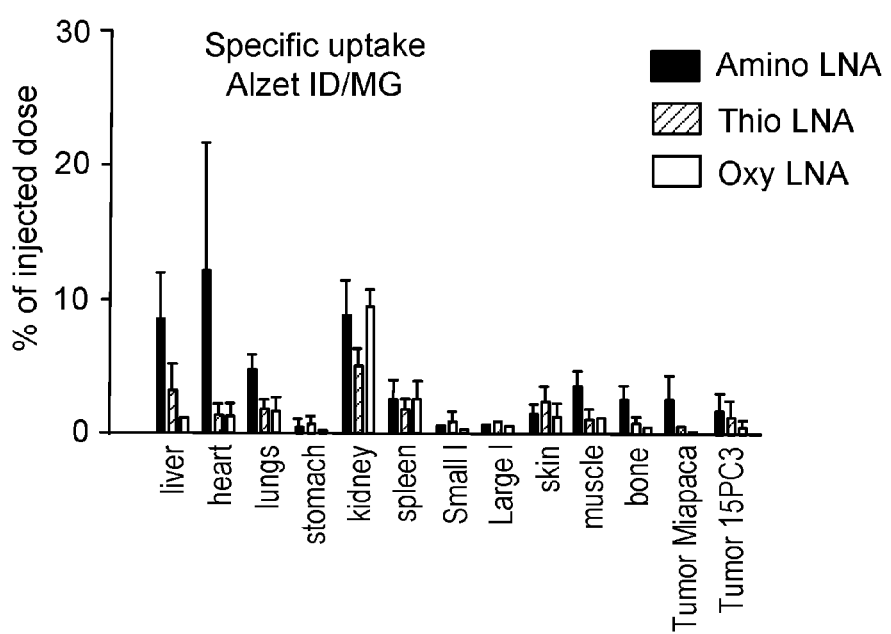
FIG. 8B: Specific uptake of titriated 2754=amino, 2748=thio and 2742=oxy after 14 days of continuous administration at a 2.5 mg/Kg/day dosage using Alzet osmotic minipumps.

Moreover, a group of 4 nude mice xenografted with 15PC3 tumors on the left side and MiaPacaII tumors on the right side were treated for 72 h with Alzet osmotic minipumps with a 2.5 mg/Kg/day dosage of tritiated 2754. After the treatment, the radioactivity present in the different tissues was measured. FIG. 8 shows the distribution of 2754 in the tissues as a total uptake and as a specific uptake. It seems that the tissue takes up significantly better amino-LNA than beta-D-oxy LNA. The main sites of uptake were liver, muscle, kidney, skin, bone and heart. When corrected for tissue weight, kidney, heart and liver (lungs and muscle in a lower extent) were the main uptake sites. This pattern differs to a certain extent from the one observed for beta-D-oxy-LNA. It is also noteworthy that the uptake of amino-LNA is significantly better in tumor tissue than for e.g. beta-D-oxy LNA (see FIGS. 7 and 8).

RNase H Assay

Rnase H is a ubiquitous cellular enzyme that specifically degrades the RNA strand of DNA/RNA hybrids, and thereby inactivates the mRNA toward further cellular metabolic processes. The inhibitory potency of some antisense agents seems to correlate with their ability to elicit ribonuclease H (RNaseH) degradation of the RNA target, which is considered a potent mode of action of antisense oligonucleotides. As such, understanding the mechanisms of catalytic function and substrate recognition for the RNaseH is critical in the design of potential antisense molecules.

It was our aim to evaluate the RNaseH activity of gapmers containing beta-D-amino-LNA. From FIG. 9, we can appreciate a good cleavage activity for an oligonucleotide containing beta-D-amino-LNA, as in table 2.

Beta-D-Thio-LNA

Nuclease Stability

As we did for beta-D-amino-LNA, beta-D-thio-LNA was also evaluated against a 3'-exonuclease (SVPD). The oligonucleotide is synthesized on deoxynucleoside-support (t). The study was carried out with oligothymidylates by blocking the 3'-end with beta-D-thio-LNA.

Figure 10:
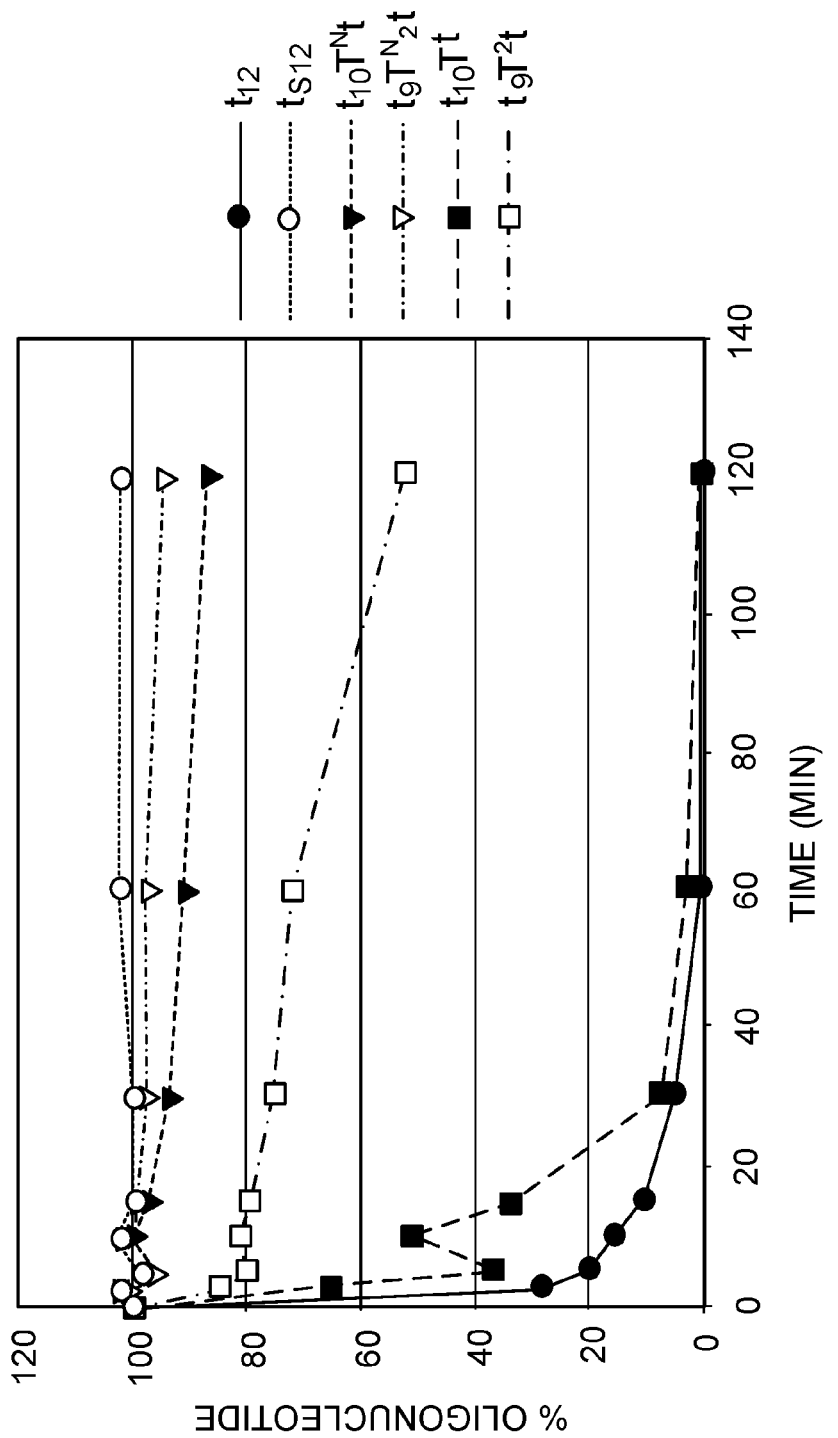
FIG. 10: Stability of oligonucleotides containing beta-D-thio-LNA against SVPD. (Capital letters are LNA, $T^S$ stands for beta-D-thio-LNA and small letters are DNA. The oligonucleotide is synthesized on deoxynucleoside-support, t.)

From FIG. 10, we can see that the incorporation of just one T-monomer of 2'-beta-D-thio-LNA (Ts) has a significant effect in the nucleolytic resistance of the oligonucleotide towards SVPD. After 2 h digestion more than 80% of the oligonucleotide remains, while the corresponding beta-D-oxy-LNA oligonucleotide is digested by the exonuclease, see FIG. 10.

Unassisted Cellular Uptake

The efficiency of FAM-labelled oligonucleotide uptake was measured as the mean fluorescence intensity of the transfected cells by FACS analysis.

The transfection without lipid showed distinct differences between the tested oligonucleotides. The uptake as measured from mean fluorescence intensity of transfected cells was dose dependent.

Figure 11:
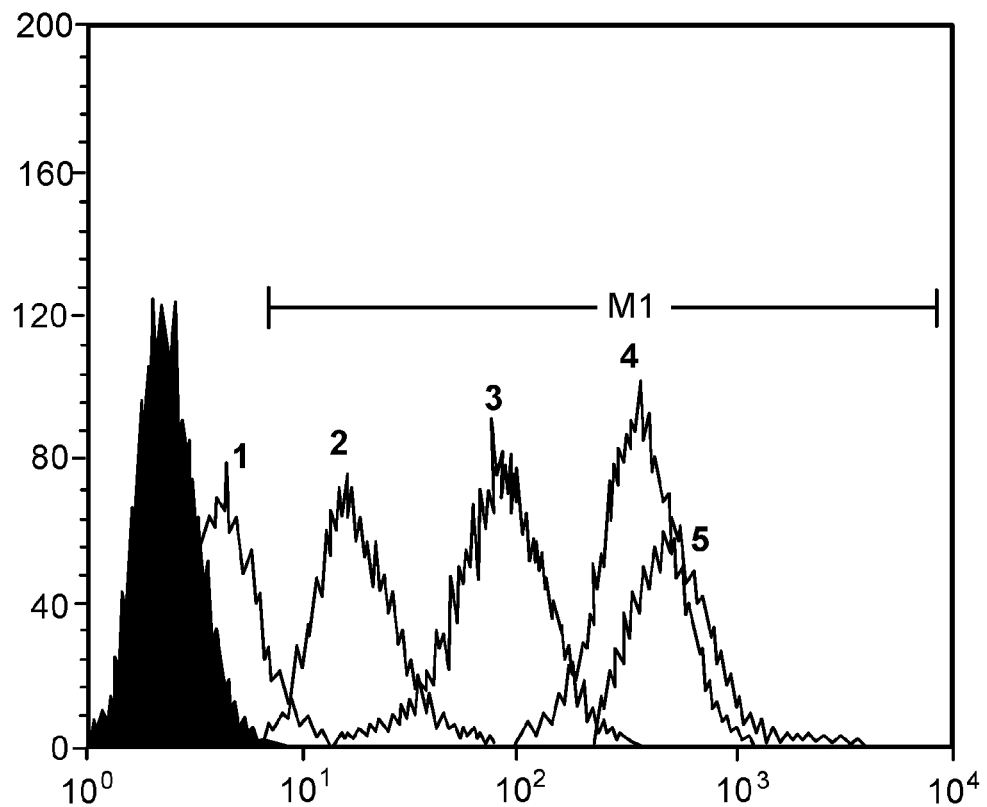
FIG. 11: FACS analysis of oligonucleotides containing beta-D-thio-LNA and the corresponding controls.

Gapmers (16 nt in length and gap of 7 nt) containing beta-D-thio-LNA in the flanks were analysed and compared with the corresponding beta-D-oxy-LNA gapmers. Beta-D-thio-LNA (one flank with beta-D-thio-LNA and the other one with oxy-LNA, as in table 5) showed higher uptake than oligonucleotides containing only oxy-LNA. The beta-D-thio-LNA oligonucleotides (both all-PO gapmer and gapmer with PS-gap and PO-flanks) had good uptake efficiency. Specially, the all-PO gapmer containing beta-D-thio-LNA was far superior to other all-PO oligonucleotides tested so far, as it can be appreciated from FIG. 11.

Assisted Cellular Uptake and Subcellular Distribution

The uptake efficiency of FAM-labeled oligonucleotide containing beta-D-thio-LNA was measured as the mean fluorescence intensity of the transfected cells by FACS analysis. Two different transfection agents were tested (Lipofectamine 2000 and DAC30) in two different cell lines (MiaPacaII and 15PC3).

Oligonucleotides both fully thiolated (PS, 2746) and partially thiolated (PO in the flanks and PS in the gap, 2747) containing beta-D-thio-LNA listed in table 4 were transfected with good efficiency, see table 4. Both transfection agents, DAC30 and Lipofectamine, presented good transfection efficiency; however, Lipofectamine was superior. Lipofectamine showed 100% efficiency in all cases: for both oligonucleotides (2746 and 2747) and in both cell lines. Moreover, no significant differences in assisted transfection efficiency were observed between 2746 and 2747.

The FAM-labeled oligonucleotide 2746 was also used to assay the subcellular distribution of oligonucleotides containing beta-D-thio-LNA, see FIG. 2. Most of the staining was detected as nuclear fluorescence that appeared as bright spherical structures (the nucleoli is also stained) in a diffuse nucleoplasmic background, as well as some cytoplasmic staining in bright punctate structures. The observed distribution patterns were similar for 15PC3 and MiaPacaII.

The subcellular distribution of beta-D-thio-LNA was comparable to the one observed with beta-D-oxy-LNA, 2740.

The uptake efficiency was also measured with tritium-labeled oligonucleotide 2748 (see table 6 and FIG. 3) at different concentrations 100, 200, 300 and 400 nM, using Lipofectamine2000 as transfection agent, both in MiaPacaII and 15PC3 cells, and compared with the equivalent beta-D-oxy-LNA, 2742 (see table 6). 2748 shows superior uptake than 2742.

Antisense Activity Assay: Luciferase Target

We also introduced beta-D-thio-LNA in a gapmer design, and evaluated it in terms of antisense activity.

The oligonucleotides from table 5 were prepared. We decided to carry out the study with gapmers of 16 nt in length and a gap of 7 nt, which contain 4 residues of beta-D-thio-LNA in one flank and 4 residues of oxy-LNA in the other flank, and a thiolated gap.

The FAM group was shown not to affect the antisense ability of the oligonucleotides. Therefore, we prepared a FAM-labelled oligonucleotide to be both tested in the Luciferase assay, and in the Cellular uptake (unassisted).

The oligonucleotide, which is directed against a motif of the mRNA of the firefly luciferase, contains two mismatches in the flanks. Two C residues of the 5'-end LNA flank were substituted for two Ts for synthetic reasons. At that point in time, only the T residues were available. Therefore and in order to be able to establish a correct comparison, the corresponding oxy-LNA control was also included in the assay. No FAM labeling was necessary in this case.

TABLE 4

Oligonucleotides (SEQ ID NOS 14-15 & 3, respectively, in order of appearance) containing beta-D-thio-LNA used in cellular uptake and subcellular distribution experiments. Residue c is methyl-c both for DNA and LNA.

| ref | oligonucleotides | DAC30 | | Lipofectamine 2000 | |
| --- | --- | --- | --- | --- | --- |
| | | % cells | % uptake | % cells | % uptake |
| 2747 | T$^S$C$^S$C$^S$g$_s$t$_s$c$_s$a$_s$t$_s$c$_s$g$_s$c$_s$t$_s$C$^S$C$^S$T$^S$c-FAM | — | — | 100 | 100 |
| 2746 | T$^S_s$C$^S_s$C$^S_s$g$_s$t$_s$c$_s$a$_s$t$_s$C$_s$g$_s$c$_s$t$_s$C$^S_s$C$^S_s$T$^S_s$c-FAM | 80 | 50 | 100 | 100 |
| 2740 | T$_s$C$_s$C$_s$g$_s$t$_s$c$_s$a$_s$t$_s$c$_s$g$_s$c$_s$t$_s$C$_s$C$_s$T$_s$c-FAM | 80 | 30 | 100 | 100 |

TABLE 5

Oligonucleotide (SEQ ID NOS 16 & 5, respectively, in order of appearance containing beta-D-thio-LNA used in the antisense activity assay and the corresponding oxy-LNA control (Capital letters for LNA and small letters for DNA, $T^S$ is beta-D-thio-LNA). Residue c is methyl-c both for LNA.

| ref | sequence | design | size |
|---|---|---|---|
| U-16 | $T^S T^S T^S T^S g_s t_s c_s a_s t_s c_s g_s$TCTTT-FAM | Thio-LNA in one flank/PS gap of 7 | 16 mer |
| 2023-m; 02579 | TTTTg$_s$t$_s$c$_s$a$_s$t$_s$c$_s$g$_s$TCTTT | Control with oxy-LNA | 16 mer |

From FIG. 4, it can be seen that the oligonucleotide with beta-D-thio-LNA presents good antisense activity at 50 nM oligonucleotide concentration. Therefore, the inclusion of beta-D-thio-LNA in the flanks of an oligonucleotide results in good down-regulation, and is at least as good as the parent all beta-D-oxy-LNA gapmer.

Antisense Activity Assay: Ha-Ras Target

It was of our interest to further evaluate the antisense activity of oligonucleotides containing beta-D-thio-LNA in a gapmer design, and compare them with beta-D-oxy-LNA gapmers.

The oligonucleotides from table 6 were prepared. We decided to carry out the study with oligonucleotides of 16 nt in length and a gap of 8 nt, which contain 3 residues of beta-D-thio-LNA in each flank and a different extent of thiolation. 2748 is fully thiolated (PS), while 2749 is only thiolated in the gap (PO in the flanks and PS in the gap). The oligonucleotides were designed to target a motif of the mRNA of Ha-Ras. Different mismatch controls were also included, 2750 is fully thiolated and 2751 presents thiolation only in the gap, see table 6. Moreover, the corresponding beta-D-oxy-LNA gapmers (see table 6, 2742 is all PS, 2744 is the corresponding mismatch control; 2743 has PS in the gap, 2745 is the corresponding mismatch control) were also tested.

TABLE 6

Oligonucleotides (SEQ ID NOS 17-18, 8-9, 19-20 & 12-13, respectively, in order of appearance) containing beta-D-thio-LNA and beta-D-oxy-LNA used in the antisense activity experiments. Residue c is methyl-c both for DNA and LNA.

| ref | oligonucleotides | |
|---|---|---|
| 2749 | $T^S C^S C^S g_s t_s c_s a_s t_s c_s g_s c_s t_s C^S C^S T^S c$ | PO/PS |
| 2748 | $T^S_s C^S_s C^S_s g_s t_s c_s a_s t_s c_s g_s c_s t_s C^S_s C^S_s T^S_s c$ | All PS |
| 2743 | TCCg$_s$t$_s$c$_s$a$_s$t$_s$c$_s$g$_s$c$_s$t$_s$CCTc | PO/PS |
| 2742 | T$_s$C$_s$C$_s$g$_s$t$_s$c$_s$a$_s$t$_s$c$_s$g$_s$c$_s$t$_s$C$_s$C$_s$T$_s$c | All PS |
| 2751 | $T^S C^S T^S g_s t_s a_s a_s t_s a_s g_s c_s c_s C^S C^S C^S c$ | Mismatch control |
| 2750 | $T^S_s C^S_s T^S_s g_s t_s a_s a_s t_s a_s g_s c_s c_s C^S_s C^S_s C^S_s c$ | Mismatch control |
| 2745 | TCTg$_s$t$_s$a$_s$a$_s$t$_s$a$_s$g$_s$c$_s$c$_s$CCCc | Mismatch control |
| 2744 | T$_s$C$_s$T$_s$g$_s$t$_s$a$_s$a$_s$t$_s$a$_s$g$_s$c$_s$c$_s$C$_s$C$_s$C$_s$c | Mismatch control |

The inclusion of beta-D-thio-LNA in the flanks of an oligonucleotide results in good down-regulation levels.

Figure 5A:
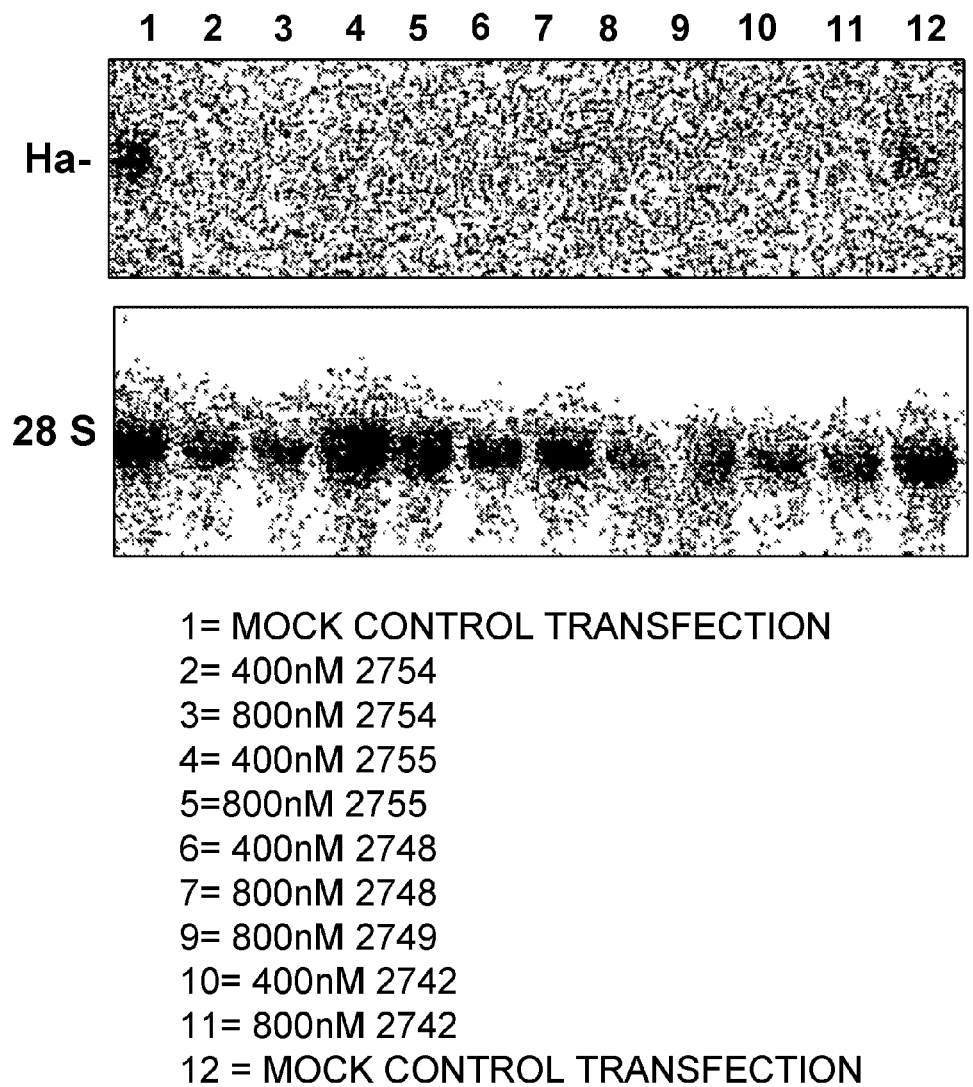
FIG. 5A: Northern blot of oligonucleotides containing beta-D-amino-LNA (2754 and 2755), beta-D-thio-LNA (2748 and 2749) or beta-D-oxy-LNA (2742) at 400 and 800 nM in 15PC3 cells transfected with Lipofectamine2000.
Figure 5B:
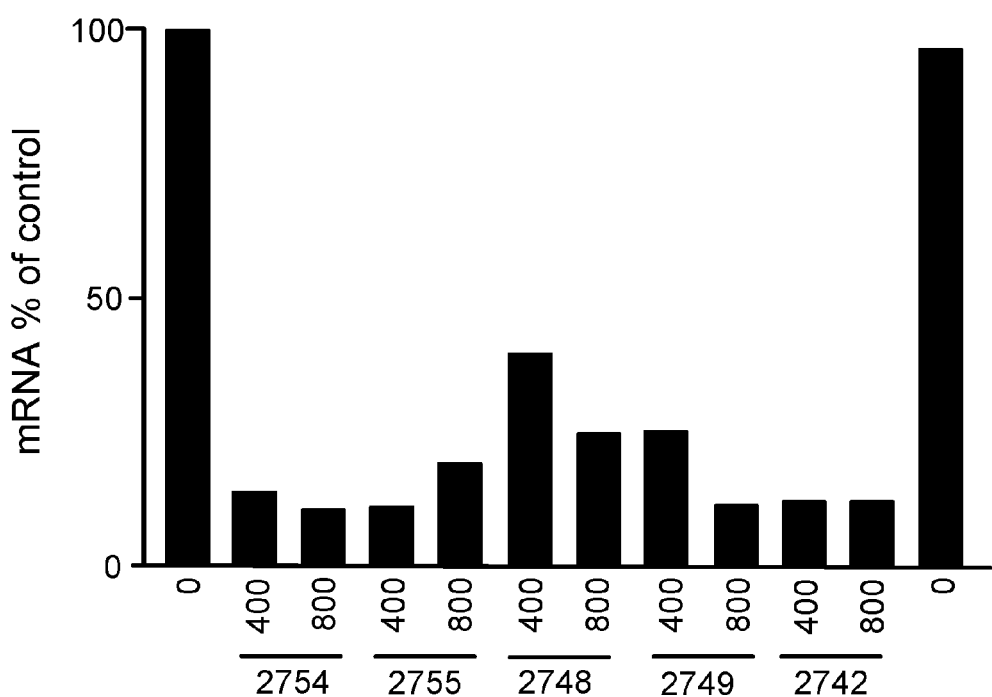
FIG. 5B: Quantification of Northern blot of oligonucleotides containing beta-D-amino-LNA (2754 and 2755), beta-D-thio-LNA (2748 and 2749) or beta-D-oxy-LNA (2742) at 400 and 800 nM in 15PC3 cells transfected with Lipofectamine2000.
Figure 5C:
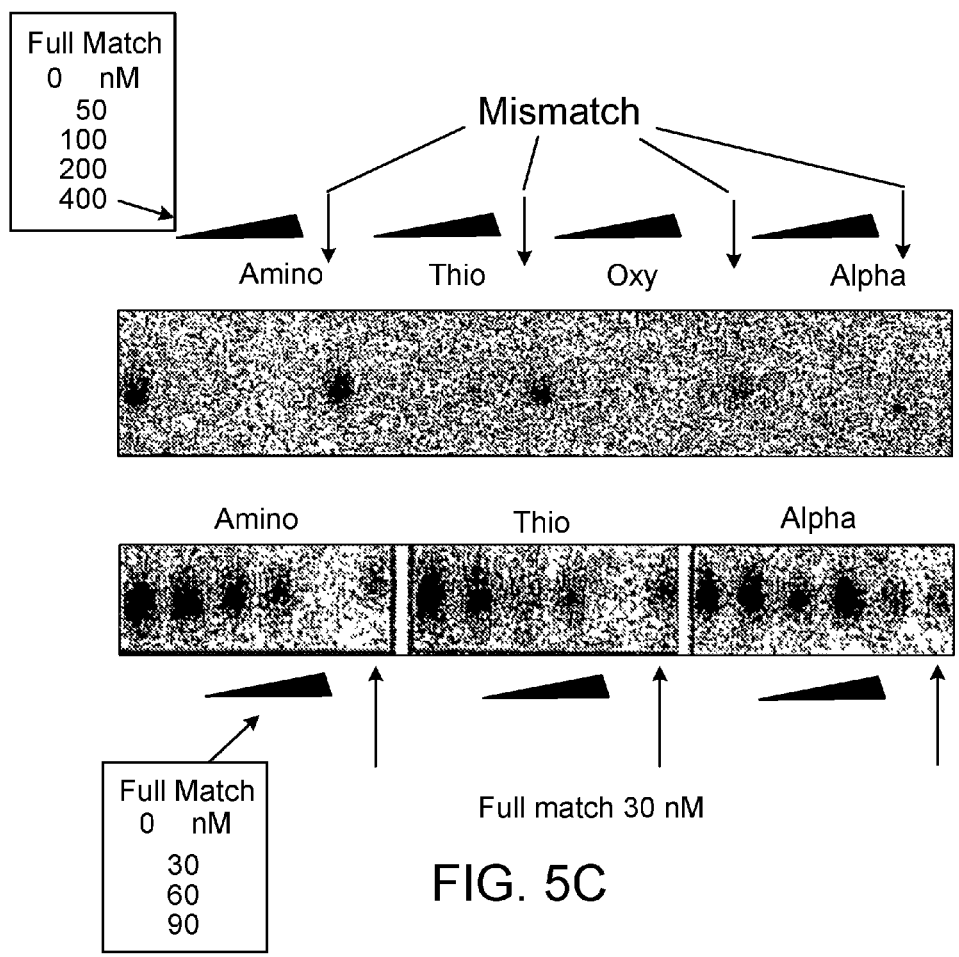
FIG. 5C: Northern blot of titration oligonucleotides containing beta-D-amino-LNA (2754 and 2755), beta-D-thio-LNA (2748 and 2749) or beta-D-oxy-LNA (2742).

From FIG. 5, we can see that oligonucleotides with beta-D-thio-LNA present good antisense activity at two different concentrations, 400 and 800 nM. No significant difference in down-regulation can be seen between oligonucleotides 2749 and 2748, which present a different degree in thiolation. However, 2749 presents better levels of down-regulation, both at 400 and 800 nM. We can conclude that the antisense activity of an oligonucleotide containing beta-D-thio-LNA lies in the range of the parent beta-D-oxy-LNA gapmer. From FIG. 6, a wider range of concentration was tested. There is a potent down-regulation between 50-400 nM for 2748. The specificity was also tested; at 30 nM there is a significant difference in down-regulation between the mismatch 2750 (less potent) and the match 2748.

Biodistribution

The biodistribution of oligonucleotides containing beta-D-thio-LNA (tritiated 2748) was also studied, both after i.v. injection and using Alzet osmotic minipumps.

2748 was administered to xenografted mice with 15PC3 tumors on the left side and MiaPacaII tumors on the right side as an intraveneous injection, and the analysis was carried out after 30 min circulation. From FIG. 7, the serum clearance for 2748 is very rapid, and the biodistribution looks very similar to the biodistribution pattern presented by the reference containing beta-D-oxy-LNA; the kidney and the liver (to lesser extent) are the main sites of uptake, when corrected for tissue weight.

Moreover, a group of 4 nude mice xenografted with 15PC3 tumors on the left side and MiaPacaII tumors on the right side were treated for 72 h with Alzet osmotic minipumps with a 2.5 mg/Kg/day dosage. After the treatment, the radioactivity present in the different tissues was measured. FIG. 8 shows the distribution of 2748 in the tissues as a total uptake and as a specific uptake. The main sites of uptake were liver, muscle, kidney, skin and bone. When corrected for tissue weight, kidney and liver were the main uptake sites.

RNaseH Assay

We also evaluated gapmer designs that contain beta-D-thio-LNA, as in table 5, for their ability to recruit RNaseH activity.

Figure 9:
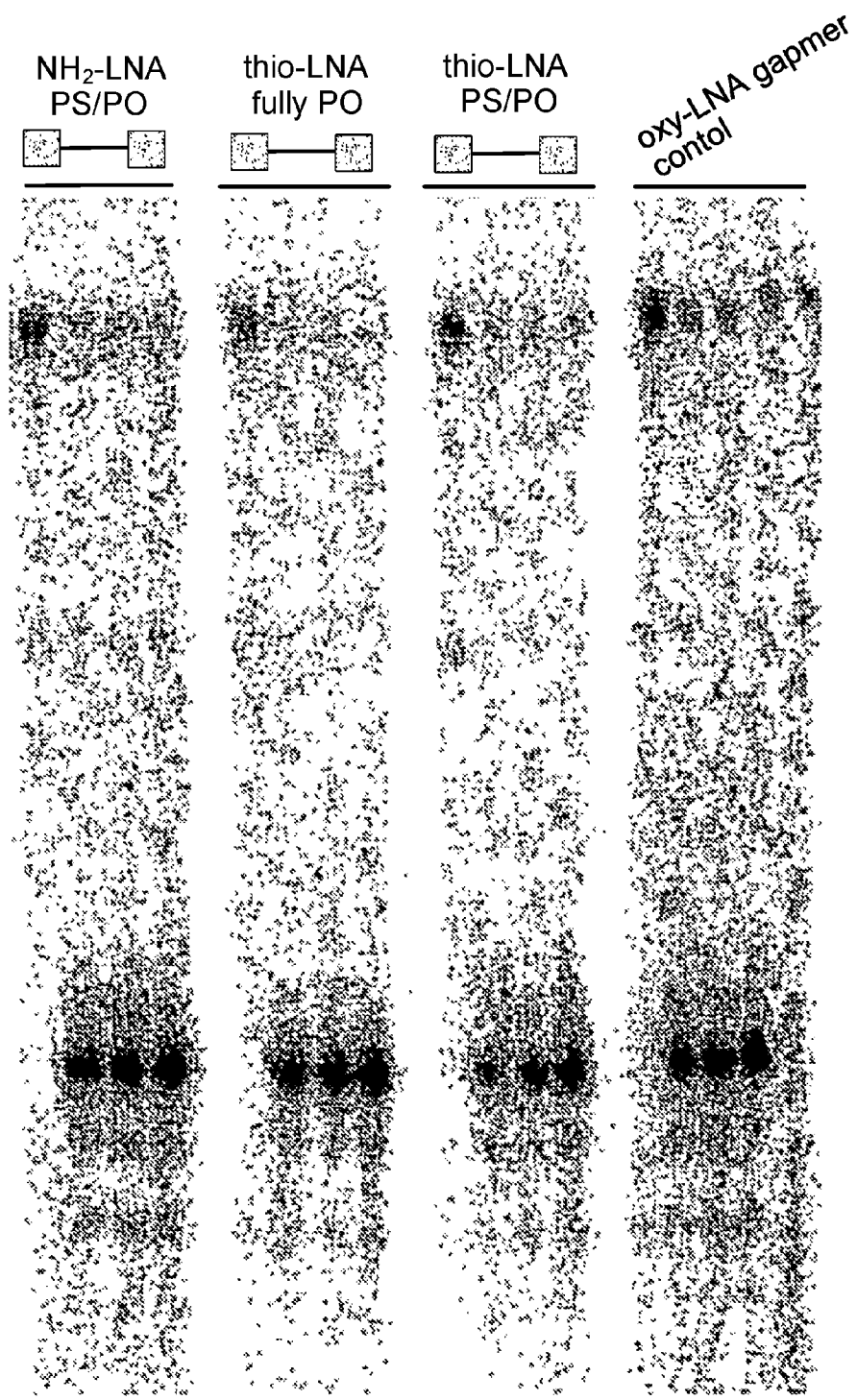
FIG. 9: Electrophoresis analysis of $^{32}$P-labelled target RNA degradation products mediated by RNaseH and an oligonucleotide containing beta-D-amino-LNA. Aliquots taken at 0, 10, 20 and 30 min for each design. In the drawings, the line is DNA, the rectangle beta-D-amino- or -thio-LNA.

From FIG. 9, we can see that a beta-D-thio-LNA gapmer recruits RnaseH activity.

Alpha-L-oxy LNA

Nuclease Stability

Figure 12:
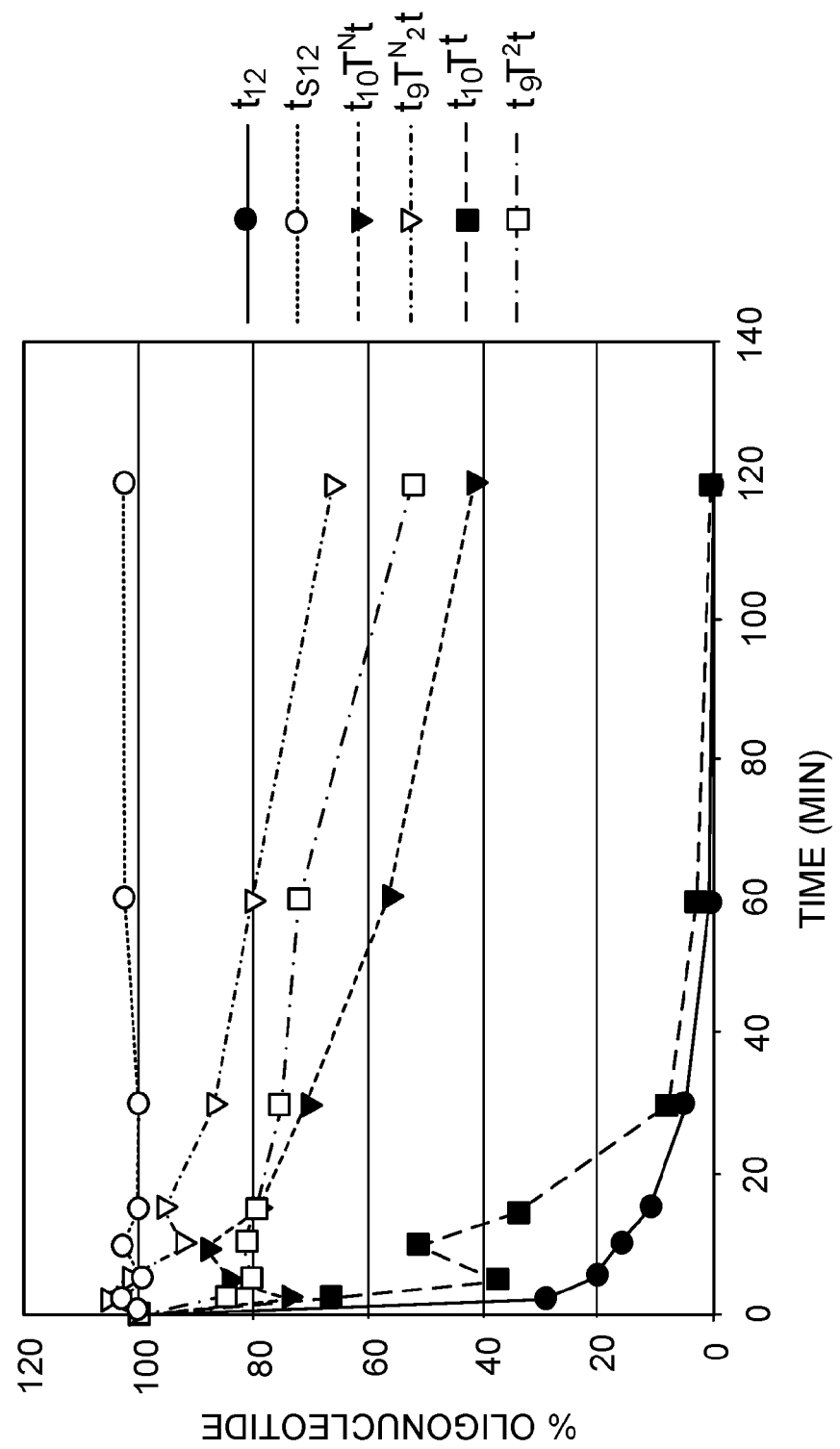
FIG. 12: Stability of oligonucleotides containing alpha-L-oxy-LNA against SVPD. (Capital letters are LNA, $T^\alpha$ stands for alpha-L-oxy-LNA and small letters are DNA. The oligonucleotide is synthesized on deoxynucleoside-support, t.)

The stabilization properties of alpha-L-oxy-LNA were also evaluated. The study was carried out with oligothymidylates by blocking the 3'-end with alpha-L-oxy-LNA. The oligonucleotide is synthesized on deoxynucleoside-support (t). From FIG. 12, we can see that the introduction of just one alpha-L-T ($T^\alpha$) at the 3'-end of the oligonucleotide represents already a gain of 40% stability (after 2 h digestion) with respect to the oxy-version, for which there was actually no gain. The addition of two modifications contributes even more to the stability of the oligonucleotide.

Furthermore, we investigated the effect on stability against S1-endonuclease of alpha-L-oxy-LNA for a 16mer fully modified oligothymidylates. The increased stability of these modified oligonucleotides relative to their deoxynucleotide and phosphorothioate backbone relatives was compared in order to carefully assess the contribution of the alpha-L-oxy-LNA modification.

Figure 13:
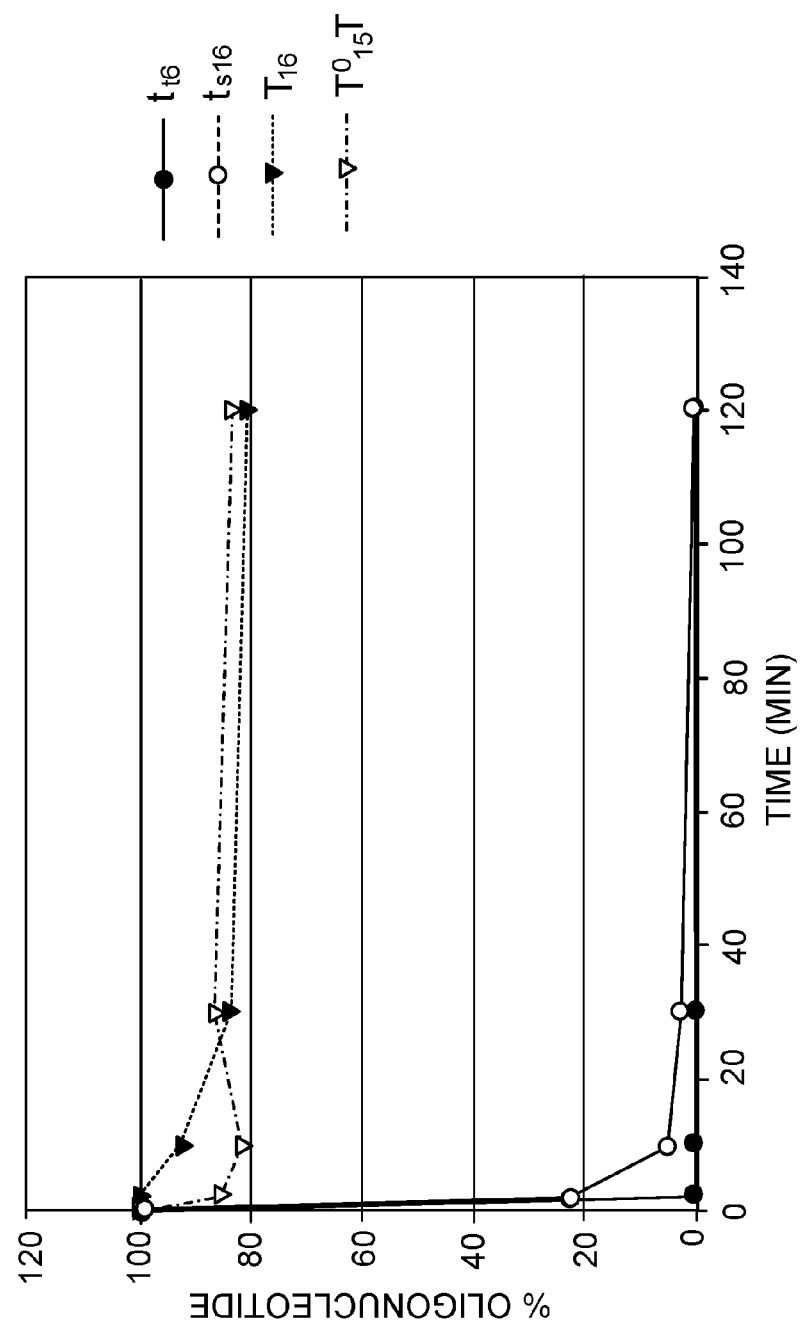
FIG. 13: Stability of different oligonucleotides ($t_{16}$, $t_{s12}$, $T_{16}$, $T^\alpha{}_{15}T$) against S1-endonuclease. (Capital letters are LNA, $T^\alpha$ stands for alpha-L-oxy-LNA and small letters are DNA. The oligonucleotide is synthesized on oxy-LNA-support, T.)

After 2 h digestion, most of the alpha-L-oxy-LNA oligonucleotide remained (over 80% of the full-length product remained), while neither the oligodeoxynucleotide nor the DNA phosphorothioate analogue could be detected after 30 min digestion (see FIG. 13). The same kinetic study against S1-endonuclease was carried out with a fully modified oxy-LNA oligonucleotide, which was also very resistant against the S1-endonuclease. Over an 85% of the full-length product remained after 2 h digestion (see FIG. 13).

In conclusion, beta-D-oxy-LNA, beta-D-amino-LNA, beta-D-thio-LNA and alpha-L-oxy-LNA stabilize oligonucleotides against nucleases. An order of efficiency in stabilization can be established: DNA phosphorothioates<<oxy-LNA<α-L-oxy-LNA<beta-D-amino-LNA<beta-D-thio-LNA.

Unassisted Cellular Uptake

Figure 14:
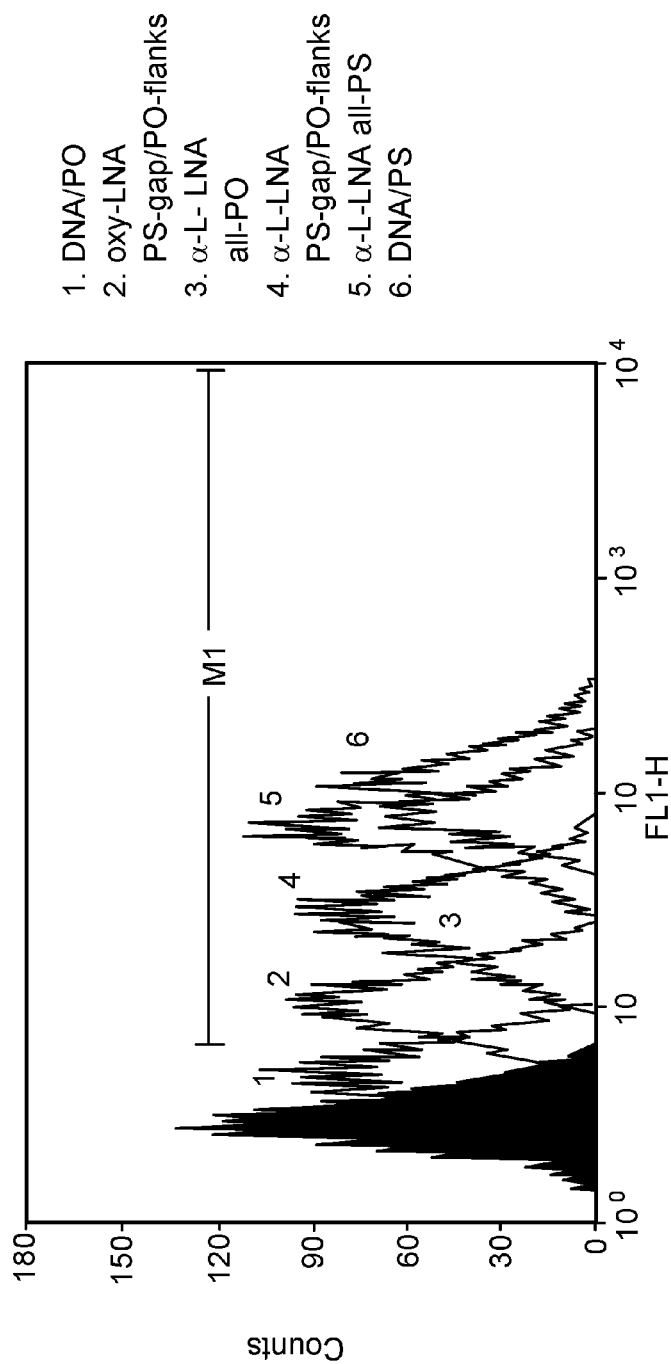
FIG. 14: FACS analysis of oligonucleotides containing alpha-L-oxy-LNA, and the corresponding controls.

The efficiency of FAM-labelled oligonucleotide uptake was measured as the mean fluorescence intensity of the transfected cells by FACS analysis. The uptake as measured from mean fluorescence intensity of transfected cells was dose dependent. Gapmers (16 nt in length and gap of 7 nt) containing α-L-oxy-LNA in the flanks were analysed and compared with the corresponding beta-D-oxy-LNA gapmer. α-L-oxy-LNA (in both flanks) showed higher uptake than the oligonucleotide containing only beta-D-oxy-LNA. Both all-PO and gapmer with PS-gap had good uptake efficiency; especially the all-PO gapmer was far superior than other all PO oligonucleotides tested so far, see FIG. 14 for FACS analysis.

Assisted Cellular Uptake and Subcellular Distribution

The uptake efficiency of FAM-labeled oligonucleotides containing alpha-L-oxy-LNA was measured as the mean fluorescence intensity of the transfected cells by FACS analysis. Two different transfection agents were tested (Lipofectamine 2000 and DAC30) in two different cancer cell lines (MiaPacaII and 15PC3).

agents, DAC30 and Lipofectamine, presented good transfection efficiency; however, Lipofectamine was superior. Lipofectamine showed 100% efficiency in all cases: for both oligonucleotides (2773 and 2774) and in both cell lines. Moreover, no significant differences in assisted transfection efficiency were observed between 2773 and 2774.

The FAM-labeled oligonucleotide 2774 was also used to assay the subcellular distribution of oligonucleotides containing alpha-L-oxy-LNA, see FIG. 2. Most of the staining was detected as nuclear fluorescence that appeared as bright spherical structures (the nucleoli is also stained) in a diffuse nucleoplasmic background, as well as some cytoplasmic staining in bright punctate structures. The observed distribution patterns were similar for 15PC3 and MiaPacaII.

The subcellular distribution of alpha-L-oxy-LNA was comparable to the one observed with beta-D-oxy-LNA, 2740.

Antisense Activity: Luciferase Target
Gapmers Containing Alpha-L-oxy-LNA

We also wanted to see the antisense activity in a gapmer oligonucleotides containing alpha-L-oxy-LNA (16 nt in length with a thiolated 7 nt gap). Two different designs were evaluated.

Figure 15:
FIG. 15: Gapmers including alpha-L-oxy-LNA (shadowed in gray).

First, we substituted two oxy-LNA residues for two alpha-L-oxy-LNAs in a gapmer against a motif of the mRNA of the firefly luciferase, and placed the alpha-L-oxy-LNA in the junctions, see FIG. 15.

Then, we substituted both flanks with alpha-L-oxy-LNA in the same construct, see FIG. 15.

Previously, different oligonucleotides were tested and compared with the corresponding FAM-labelled molecules, and no significant difference was appreciated between the free and FAM-labelled ones. Therefore, we included oligonucleotides from the Unassisted Cellular Uptake assay in the Luciferase assay study, assuming that the antisense activity will not be affected by the presence of the FAM group.

Figure 16:
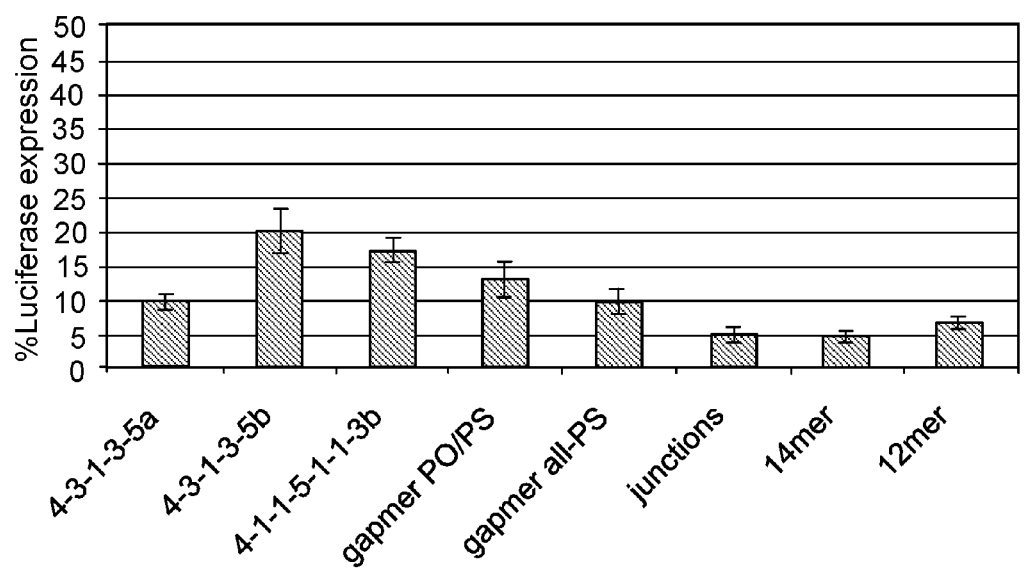
FIG. 16: Down-regulation of Luciferase expression of oligonucleotides containing alpha-L-oxy-LNA at 50 nM oligonucleotide concentration.

From FIG. 16, the oligonucleotide with alpha-L-oxy-LNA in the junctions shows potent antisense activity. It is actually 5-fold better than the corresponding all oxy-LNA gapmer (gap of 7 nt), and slightly better than a gapmer with an optimised 9 nt gap with oxy-LNA.

The second design (all alpha-L-oxy-LNAs in both flanks) presents at least as good down-regulation levels as the observed for beta-D-oxy-LNA gapmers. We can also conclude that the presence of the alpha-L-oxy-LNA in a gapmer construct shows good-antisense activity level.

TABLE 7

Oligonucleotides (SEQ ID NOS 21-22 & 3, respectively in order of appearance) containing alpha-L-oxy-LNA used in cellular uptake and subcellular distribution experiments. Residue c is methyl-c both for DNA and LNA.

|      |                | DAC30   |          | Lipofectamine 2000 |          |
| ---- | -------------- | ------- | -------- | ------------------ | -------- |
| ref  | oligonucleotides | % cells | % uptake | % cells            | % uptake |
| 2773 | $T^aC^aC^ag_st_sc_sa_st_sc_sg_sc_st_sC^aC^aT^ac$-FAM | —  | —  | 100 | 100 |
| 2774 | $T^a_sC^a_sC^a_sg_st_sc_sa_st_sc_sg_sc_st_sC^a_sC^a_sT^a_sc$-FAM | 80 | 30 | 100 | 100 |
| 2740 | $T_sC_sC_sg_st_sc_sa_st_sc_sg_sc_st_sC_sC_sT_sc$-FAM | 80 | 30 | 100 | 100 |

Oligonucleotides both fully thiolated (PS, 2774) and partially thiolated (PO in the flanks and PS in the gap, 2773) containing alpha-L-oxy-LNA listed in table 7 were transfected with good efficiency, see table 7. Both transfection alpha-L-oxy-LNA reveals to be a potent tool enabling the construction of different gapmers, which show good antisense activity. The placement of alpha-L-oxy-LNA in the junctions results in a very potent oligonucleotide.

Short-Sized Gapmers Containing Alpha-L-oxy-LNA

As a general rule, the length of the construct is usually designed to range from 15-25 nucleotide units, in order to ensure that optimal identification and binding takes place with a unique sequence in the mammalian genome and not with similar genetically redundant elements. Statistical analyses specify 11-15 base paired human sequences as the theoretical lower limits for sufficient recognition of a single genomic region. In practice, however, a longer oligonucleotide is commonly used to compensate for low melting transitions, especially for thiolated oligonucleotides that have lower affinity.

As a significant increase in affinity is achieved by the introduction of oxy-LNA or novel LNA relatives, the design of potent and short antisense oligonucleotides (<15 nt) should be enabled.

The alpha-L-oxy-LNA can play an important role in enabling the design of short molecules by maintaining the required high-affinity, but also an optimal gap size. 12 and 14 mers against a motif of the mRNA of the firefly luciferase were evaluated.

The results are shown in FIG. 16. The presence of alpha-L-oxy-LNA in the flanks of a 12 (gap of 7 nt) and 14 mer (gap of 8 nt) correspond to good levels of down-regulation. From FIG. 16.

In conclusion, alpha-L-oxy-LNA is a potent tool in enabling the design of short antisense oligonucleotides with significant down-regulation levels.

Mixmers Containing Alpha-L-oxy-LNA

Figure 17A:
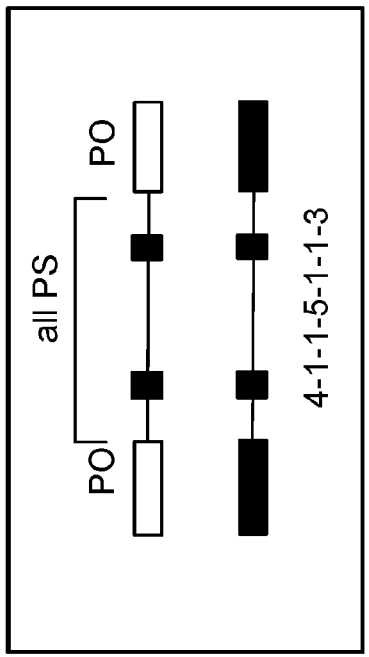
FIG. 17A: Mixmers (4-3-1-3-5) containing alpha-L-oxy-LNA. The numbers stand for the alternate contiguous stretch of DNA or LNA. In the drawing, the line is DNA, the rectangle beta-D-oxy-LNA, the gray shadow corresponds to alpha-L-oxy-LNA residues.
Figure 17B:
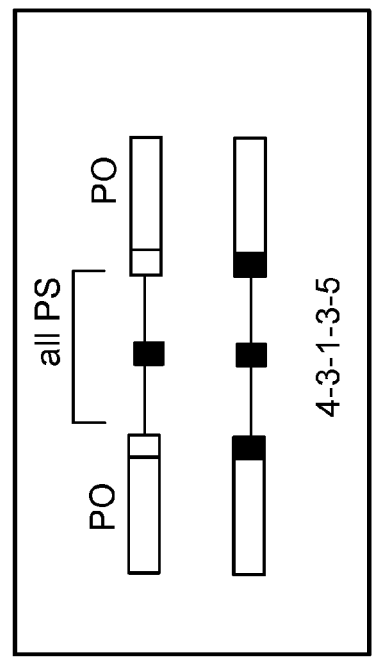
FIG. 17B: Mixmers (4-1-1-5-1-1-3) containing alpha-L-oxy-LNA. The numbers stand for the alternate contiguous stretch of DNA or LNA. In the drawing, the line is DNA, the rectangle beta-D-oxy-LNA, the gray shadow corresponds to alpha-L-oxy-LNA residues.

We also considered other designs containing alpha-L-oxy-LNA against a motif of the mRNA of the firefly luciferase, which we called mixmers. They consist of an alternate composition of DNA, alpha-L-oxy-LNA and beta-D-oxy-LNA. The following figure illustrates the chosen designs. We named the mixmers by the alternate number of units of each alpha-L-oxy-LNA, beta-D-oxy-LNA or DNA composition. See FIG. 17 and table 8 for the different designs.

The presence of just one beta-D-oxy-LNA residue (design 4-3-1-3-5) interrupting the stretch of DNAs in the gap results in a dramatic loss of down-regulation. Just by using alpha-L-oxy-LNA instead, the design shows significant down-regulation at 50 nM oligonucleotide concentration, see FIG. 16. The placement of alpha-L-oxy-LNA in the junctions and one alpha-L-oxy-LNA in the middle of the gap also shows down-regulation, see FIG. 16.

The interruption of the gap with two beta-D-oxy-LNAs (design 4-1-1-5-1-1-3) relates also with a loss in antisense activity. Again the fully substitution of beta-D-oxy-LNA for alpha-L-oxy-LNA gives significant antisense activity, see FIG. 16. alpha-L-oxy-LNA reveals to be a potent tool enabling the construction of different mixmers, which are able to present high levels of antisense activity.

Other Designs

Figure 18A:
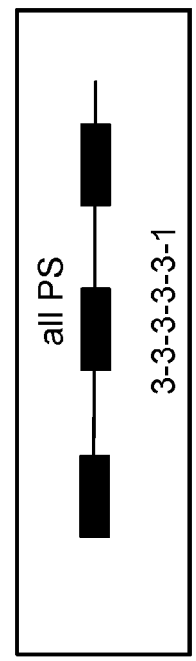
FIG. 18A: Mixmers (4-1-5-1-5) containing alpha-L-oxy-LNA. The numbers stand for the alternate contiguous stretch of DNA or alpha-L-oxy-LNA. In the drawing, the line is DNA, the gray shadow corresponds to alpha-L-oxy-LNA residues.
Figure 18B:
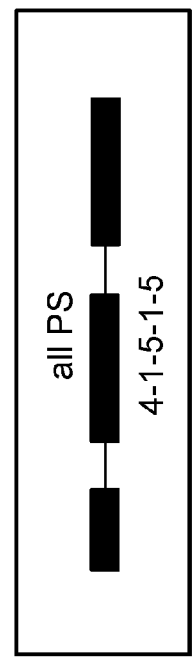
FIG. 18B: Mixmers (3-3-3-3-1) containing alpha-L-oxy-LNA. The numbers stand for the alternate contiguous stretch of DNA or alpha-L-oxy-LNA. In the drawing, the line is DNA, the gray shadow corresponds to alpha-L-oxy-LNA residues.

Other mixmers containing alpha-L-oxy-LNA were studied, see FIG. 18. Furthermore, mixmers, such as in table 8 and FIG. 17, but with no thiolation, were also tested.

Antisense Activity Assay: Ha-Ras Target

It was of our interest to further evaluate the antisense activity of oligonucleotides containing alpha-L-oxy-LNA in a gapmer design, and compare them with beta-D-oxy-LNA gapmers.

The oligonucleotides from table 9 were prepared. We decided to carry out the study with oligonucleotides of 16 nt in length and a gap of 8 nt, which contain 3 residues of alpha-L-oxy-LNA in each flank and a different extent of thiolation. 2776 is fully thiolated (PS), while 2775 is only thiolated in the gap (PO in the flanks and PS in the gap). The oligonucleotides were designed to target a motif of the mRNA of Ha-Ras. Different mismatch controls were also included, 2778 is fully thiolated and 2777 presents thiolation only in the gap, see table 9. Moreover, the corresponding beta-D-oxy-LNA gapmers (see table 9, 2742 is all PS, 2744 is the corresponding mismatch control; 2743 has PS in the gap, 2745 is the corresponding mismatch control) were also tested.

TABLE 8

Mixmers (SEQ ID NOS 23-26, respectively, in order of appearance) containing alpha-L-oxy-LNA used in this study (Capital letters for LNA and small letters for DNA, T" is alpha-L-oxy-LNA). Residue c is methyl-c both for LNA.

| ref | sequence | mixmer |
|---|---|---|
| 2023-q | TTCCg$_s$T$^a{}_s$c$_s$a$_s$t$_s$c$_s$g$_s$T$^a{}_s$c$_s$TTT | 4-1-1-5-1-1-3 a |
| 2023-r | T$^a$T$^a$C$^a$C$^a$g$_s$T$^a{}_s$c$_s$a$_s$t$_s$c$_s$g$_s$T$^a{}_s$c$_s$T$^a$T$^a$T | 4-1-1-5-1-1-3 b |
| 2023-t | TTCCg$_s$t$_s$c$_s$A$^a{}_s$t$_s$c$_s$g$_s$TCTTT | 4-3-1-3-5 a |
| 2023-u | TTCC$^a$g$_s$t$_s$c$_s$A$^a{}_s$t$_s$c$_s$g$_s$T$^a$CTTT | 4-3-1-3-5 b |

In design 4-1-1-5-1-1-3 (FIG. 17, table 8), we placed two alpha-L-oxy-LNA residues interrupting the gap, being the flanks beta-D-oxy-LNA. Furthermore, we interrupted the gap with two alpha-L-oxy-LNA residues, and substituted both flanks with alpha-L-oxy-LNA. The presence of alpha-L-oxy-LNA might introduce a flexible transition between the North-locked flanks (oxy-LNA) and the alpha-L-oxy-LNA residue by spiking in deoxynucleotide residues.

It is also interesting to study design 4-3-1-3-5 (FIG. 17, table 8), where an alpha-L-oxy-LNA residue interrupts the DNA stretch. In addition to the alpha-L-oxy-LNA in the gap, we also substituted two oxy-LNA residues at the edges of the flanks with two alpha-L-oxy-LNA residues.

TABLE 9

Oligonucleotides (SEQ ID NOS 27-28, 8-9, 29-30 & 12-13, respectively, in order of appearance), containing alpha-L-oxy-LNA and beta-D-oxy-LNA used in the antisense activity experiments. Residue c is methyl-c both for DNA and LNA.

| ref | oligonucleotides | |
|---|---|---|
| 2775 | T$^a$C$^a$C$^a$g$_s$t$_s$c$_s$a$_s$t$_s$c$_s$g$_s$c$_s$t$_s$C$^a{}^a$T$^a$c | PO/PS |
| 2776 | T$^a{}_s$C$^a{}_s$C$^a{}_s$g$_s$t$_s$c$_s$a$_s$t$_s$c$_s$g$_s$c$_s$t$_s$C$^a{}_s$C$^a{}_s$T$^a{}_s$c | All PS |
| 2743 | TCCg$_s$t$_s$c$_s$a$_s$t$_s$c$_s$g$_s$c$_s$t$_s$CCTc | PO/PS |
| 2742 | T$_s$C$_s$C$_s$g$_s$t$_s$c$_s$a$_s$t$_s$c$_s$g$_s$c$_s$t$_s$C$_s$C$_s$T$_s$c | All PS |
| 2777 | T$^a$C$^a$T$^a$g$_s$t$_s$a$_s$a$_s$t$_s$a$_s$g$_s$c$_s$c$_s$C$^a$C$^a$C$^a$c | Mismatch control |
| 2778 | T$^a{}_s$C$^a{}_s$T$^a{}_s$g$_s$t$_s$a$_s$a$_s$t$_s$a$_s$g$_s$C$_s$c$_s$C$^a{}_s$C$^a{}_s$C$^a{}_s$c | Mismatch control |
| 2745 | TCTg$_s$t$_s$a$_s$a$_s$t$_s$a$_s$g$_s$C$_s$c$_s$CCCc | Mismatch control |
| 2744 | T$_s$C$_s$T$_s$g$_s$t$_s$a$_s$a$_s$t$_s$a$_s$g$_s$c$_s$c$_s$C$_s$C$_s$C$_s$c | Mismatch control |

The inclusion of alpha-L-oxy-LNA in the flanks of an oligonucleotide results in good down-regulation levels. From FIG. 6, we can see that the oligonucleotide 2776 with alpha-L-oxy-LNA present good antisense activity at a different range of concentrations, 50 nM-400 nM. No significant difference in down-regulation can be seen between 2776 and 2742. We can conclude that the antisense activity of an oligonucleotide containing alpha-L-oxy-LNA is at least as good as the parent beta-D-oxy-LNA gapmer. The specificity was also tested; at 30 nM there is a significant difference in down-regulation between the mismatch 2778 (less potent) and the match 2776. Lower concentrations (5-40 nM) were also included from the table in FIG. 6. Potent down-regulation is observed even at 5 nM for 2776 in comparison with the corresponding beta-D-oxy-LNA control, 2742. The specificity is also remarkable, if we compare the antisense activity for 2776 at 20 nM (2.6% down-regulation) in comparison with the mismatch containing control 2778 (77% down-regulation).

RNaseH Assay

Figure 19A:
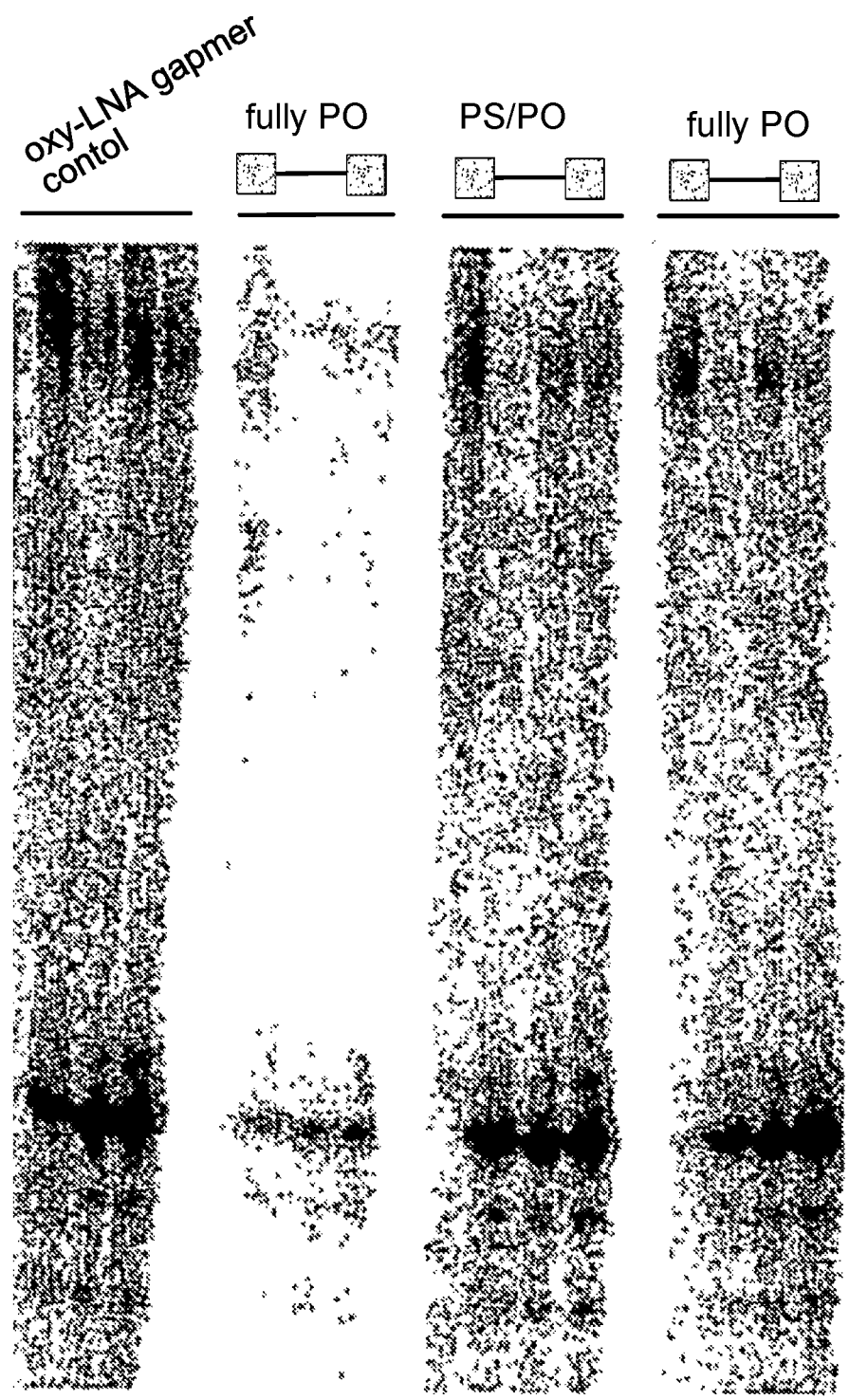
FIG. 19A: Electrophoresis analysis of $^{32}$P-labelled target RNA degradation products mediated by RNaseH and an oligonucleotide containing alpha-L-oxy-LNA. Aliquots taken at 0, 10, 20 and 30 min for each design. In the drawings, the line is DNA, the rectange beta-D-oxy-LNA, the gray shadow corresponds to alpha-L-oxy-LNA residues.
Figure 19B:
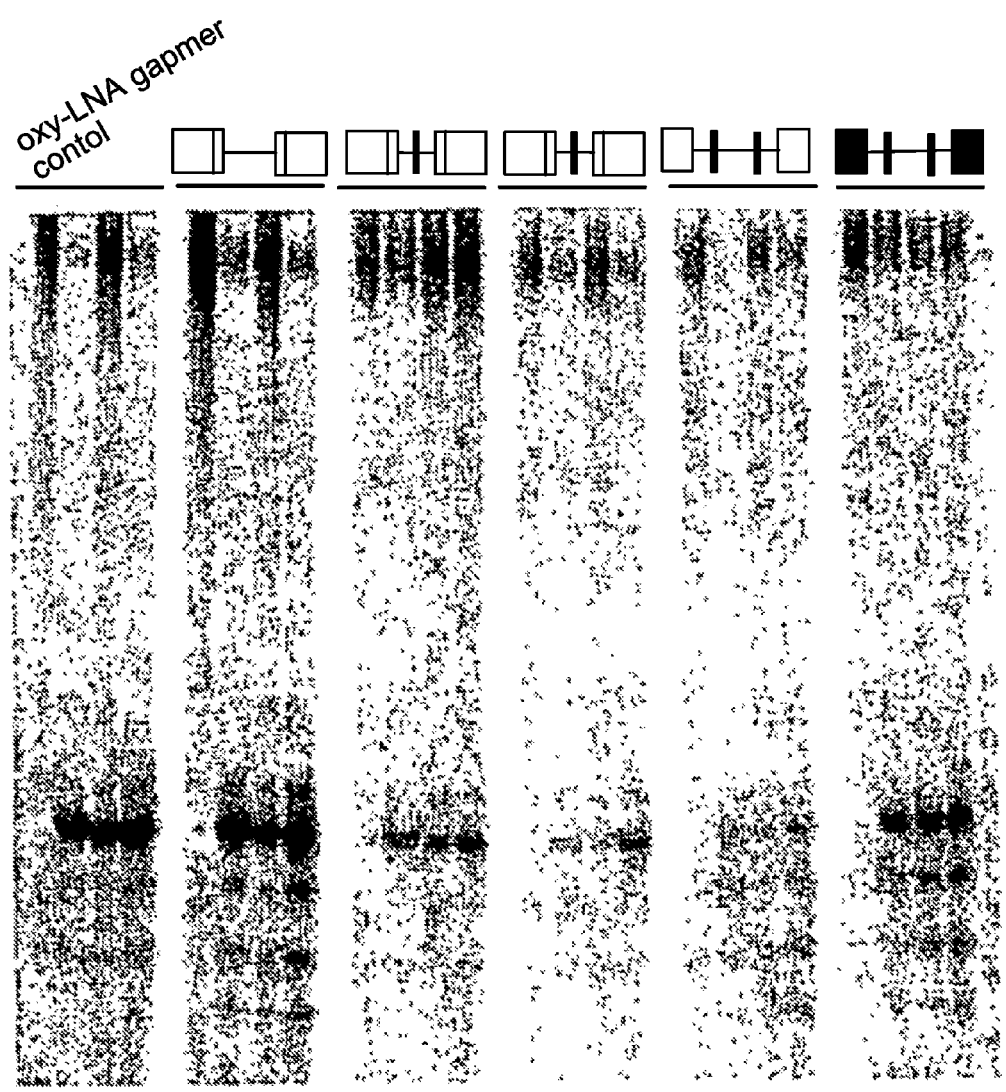
FIG. 19B: Electrophoresis analysis of $^{32}$P-labelled target RNA degradation products mediated by RNaseH and an oligonucleotide containing alpha-L-oxy-LNA. Aliquots taken at 0, 10, 20 and 30 min for each design. In the drawings, the line is DNA, the rectangle beta-D-oxy-LNA, the gray shadow corresponds to alpha-L-oxy-LNA residues.
Figure 20A:
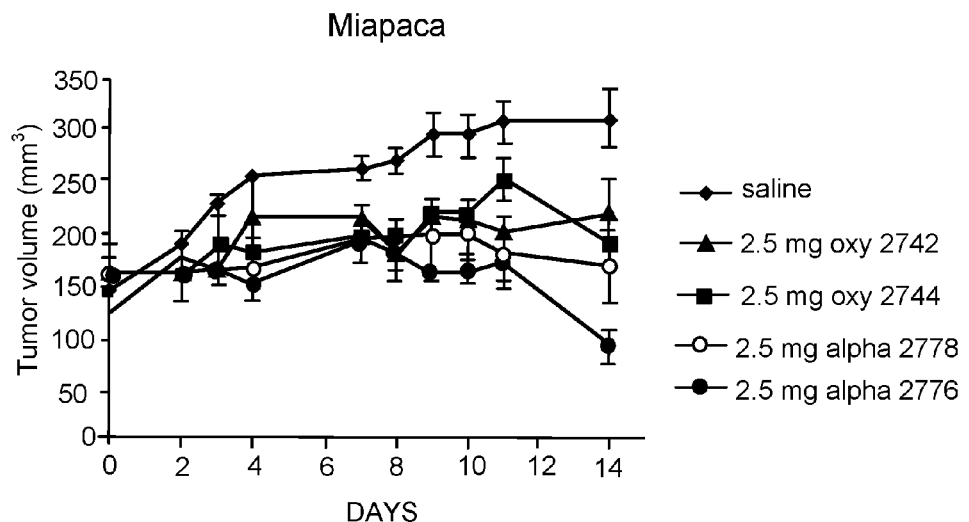
FIG. 20A: Tumor growth in nude mice treated with the indicated doses for 14 days using Alzet osmotic minipumps for MiaPacaII cells.
Figure 20B:
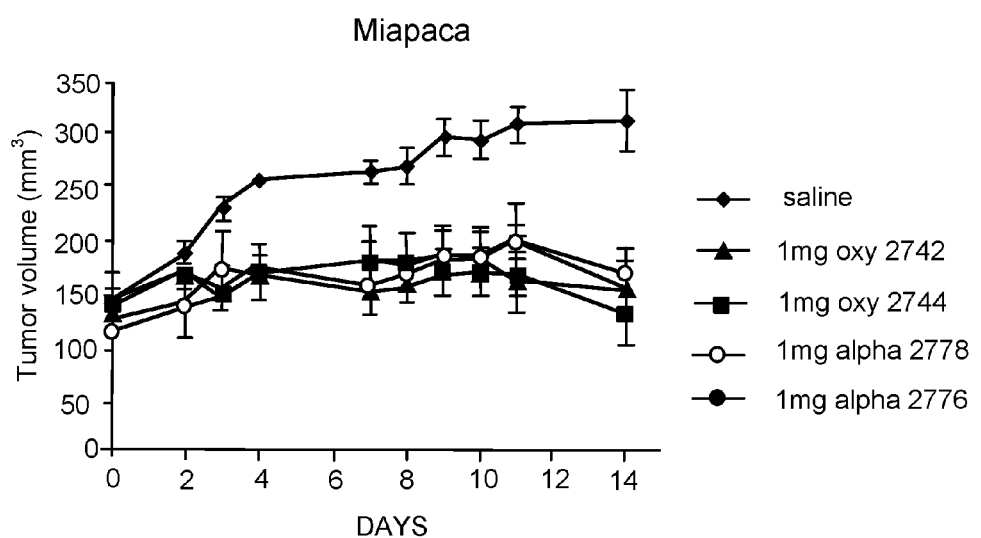
FIG. 20B: Tumor growth in nude mice treated with the indicated doses for 14 days using Alzet osmotic minipumps for MiaPacaII cells.
Figure 20C:
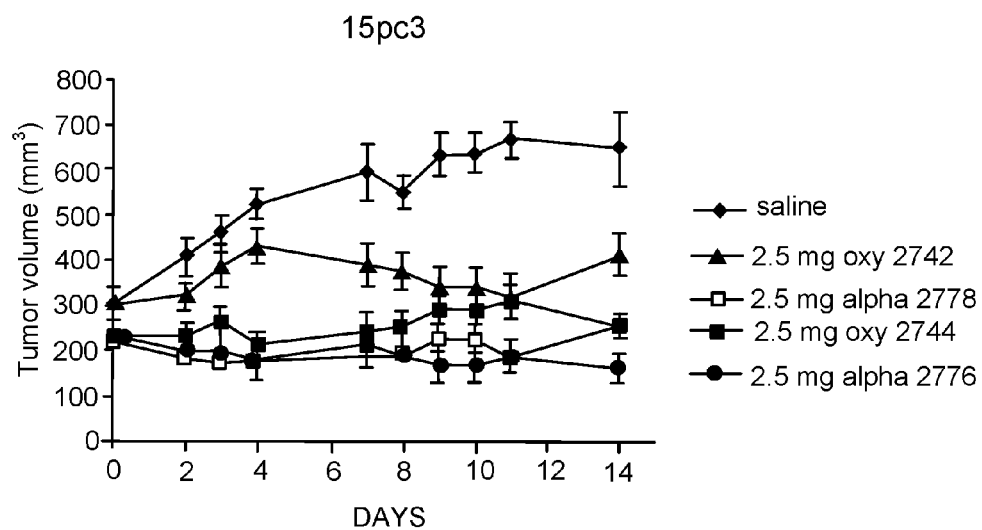
FIG. 20C: Tumor growth in nude mice treated with the indicated doses for 14 days using Alzet osmotic minipumps for 15PC3 cells.
Figure 20D:
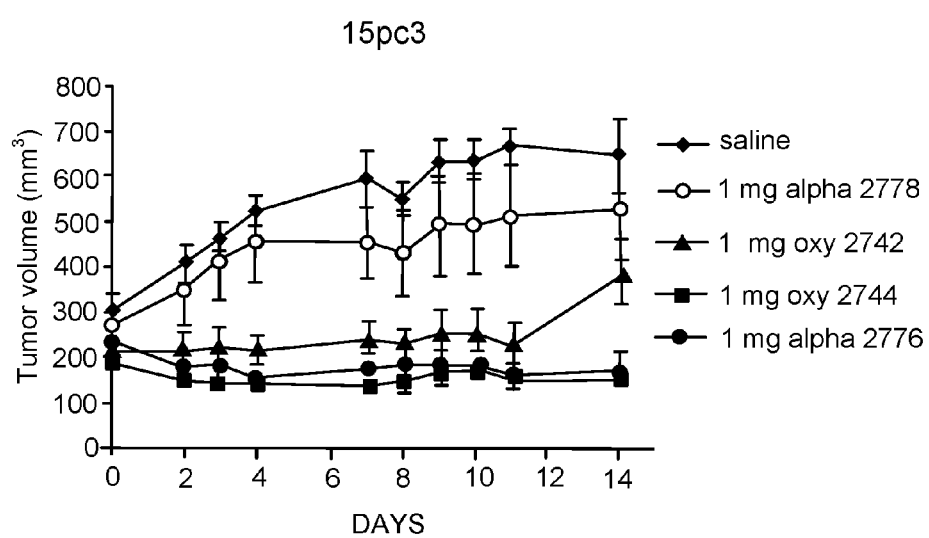
FIG. 20D: Tumor growth in nude mice treated with the indicated doses for 14 days using Alzet osmotic minipumps for 15PC3 cells.

We also evaluated gapmer designs that contain alpha-L-oxy-LNA for their ability to recruit RNaseH activity.

alpha-L-oxy-LNA gapmer and mixmer designs recruit RnaseH activity, see FIG. 19.

In Vivo Experiment

Nude mice were injected s.c. with MiaPaca II cells (right flank) and 15PC3 cells (left flank) one week prior to the start of oligonucleotide treatment to allow xenograft growth. The anti Ha-Ras oligonucleotides (2742 and 2776, table 10) and control oligonucleotides (2744 and 2778, table 10) were administrated for 14 days using Alzet osmotic minipumps (model 1002) implanted dorsally. Two dosages were used: 1 and 2.5 mg/Kg/day. During treatment the tumor growth was monitored. Tumor growth was almost inhibited completely at 2.5 mg/Kg/day and even at 1 mg/Kg/day dose with 2742 and 2776 in 15PC3 cells, FIG. 20. The specificity with control oligonucleotides (2744 and 2778, containing mismatches) increased as the dose decreased. At 1 mg/Kg/day dose the experiment presented a good specificity, particularly for alpha-L-oxy-LNA oligonucleotides (2742 and 2744). In MiaPacaII xenograft tumors, the effect of the oligonucleotides is in general comparable with those on the 15PC3 xenografts, except for the fact that the specificity seemed to be a bit lower. It can be concluded that the oligonucleotide containing alpha-L-oxy-LNA are as potent, or maybe even better, as the one containing beta-D-oxy-LNA in tumor growth inhibition in the concentration range tested.

TABLE 10

Oligonucleotides. (SEQ ID NOS 28, 30, 9 & 13, respectively, in order of appearance) containing alpha-L-oxy-LNA and beta-D-oxy-LNA used in the in vivo experiments. Residue c is methyl-c both for DNA and LNA.

| ref | oligonucleotides | |
|---|---|---|
| 2776 | $T^a_sC^a_sC^a_sg_st_sc_sa_st_sc_sg_sc_st_sC^a_sC^a_sT^a_sc$ | match |
| 2778 | $T^a_sC^a_sT^a_sg_st_sa_sa_st_sa_sg_sc_sc_sC^a_sC^a_sC^a_sa_sc$ | Mismatch control |

TABLE 10-continued

Oligonucleotides. (SEQ ID NOS 28, 30, 9 & 13, respectively, in order of appearance) containing alpha-L-oxy-LNA and beta-D-oxy-LNA used in the in vivo experiments. Residue c is methyl-c both for DNA and LNA.

| ref | oligonucleotides | |
|---|---|---|
| 2742 | $T_sC_sC_sg_st_sc_sa_st_sc_sg_sc_st_sC_sC_sT_sc$ | match |
| 2744 | $T_sC_sT_sg_st_sa_sa_st_sa_sg_sc_sc_sC_sC_sC_sc$ | Mismatch control |

Toxicity Levels

Figure 21A:
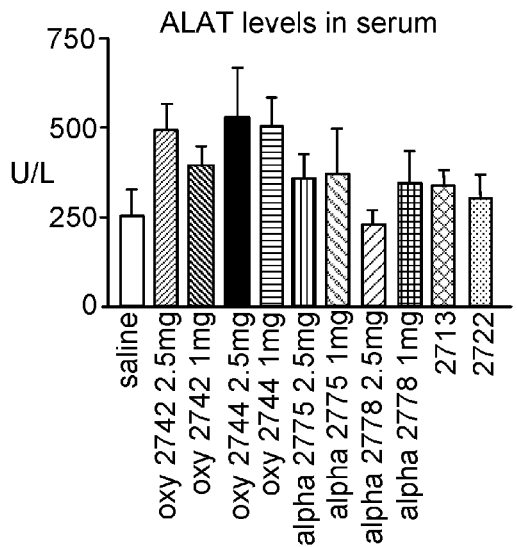
FIG. 21A: ASAT levels in mice serum after 14-day treatment using Alzet osmotic minipumps with the indicated oligonucleotides and at the indicated concentrations. 2722 and 2713 are oligonucleotides not relevant to this study.
Figure 21B:
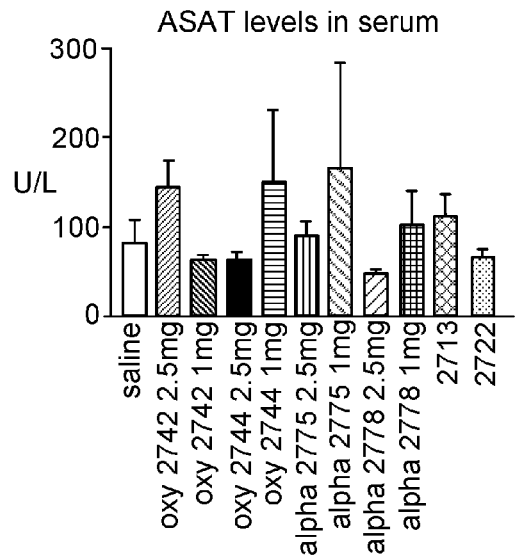
FIG. 21B: ALAT levels in mice serum after 14-day treatment using Alzet osmotic minipumps with the indicated oligonucleotides and at the indicated concentrations. 2722 and 2713 are oligonucleotides not relevant to this study.
Figure 21C:
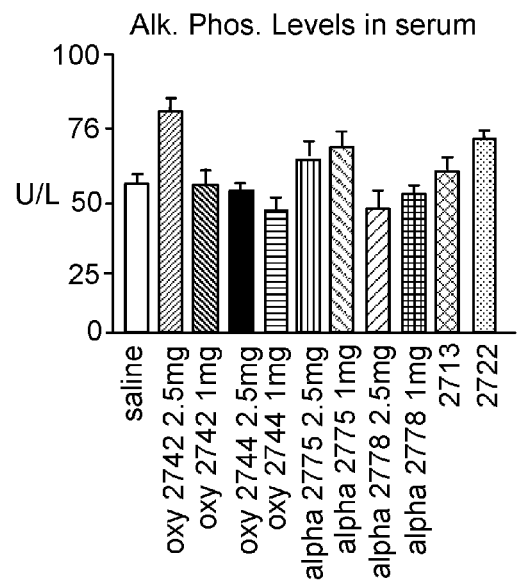
FIG. 21C: Alkaline phosphatase levels in mice serum after 14-day treatment using Alzet osmotic minipumps with the indicated oligonucleotides and at the indicated concentrations. 2722 and 2713 are oligonucleotides not relevant to this study.
Figures 21D, 22:
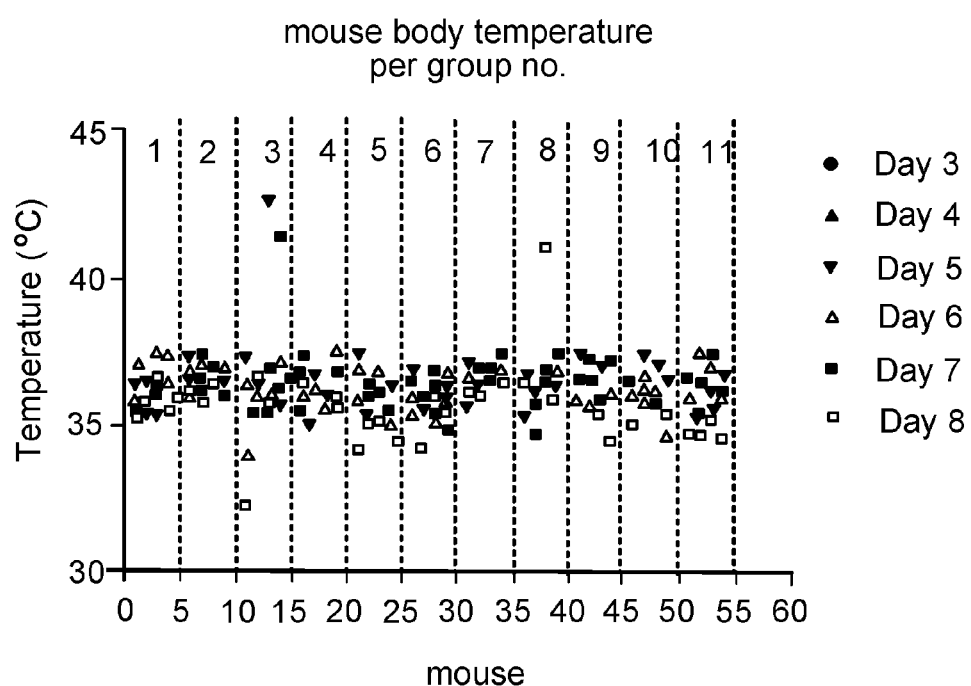
FIG. 21D: Dosages used in studies in FIGS. 21A-21C.
FIG. 22: Monitoring the body temperature of the mice during the in vivo experiment. 2722 and 2713 are oligonucleotides not relevant to this study.

The levels of aspartate aminotransferase (ASAT), alanine aminotransferase (ALAT) and alkaline phosphatase in the serum were determined, in order to study the possible effects of this 14-day treatment in the nude mice. Serum samples were taken from each mouse after the 14-day experiment. From FIG. 21, ALAT levels in the serum varied between 250-500 U/L. ASAT levels were in the range of 80-150 U/L. The mice did not seem externally to be sick, and no big changes in behavior were observed. During treatment the body temperature of the mice was also monitored (FIG. 22). The body temperature did not change significantly during the treatment, not even at high dose 2.5 mg/Kg/day, which is an indication that no major toxicity effects are occurring. In some cases, the body temperature of the mice was a bit higher, divided in two groups. These effects cannot be explained by the fact of one oligonucleotide behaving differently or one dosage being too high.

Specific Beta-D-oxy-LNA Constructs

Luciferase Target: Antisense Activity Assay

Figure 23:
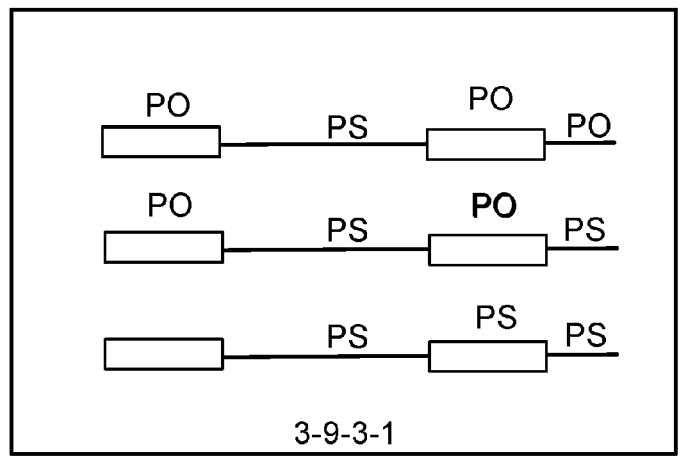
FIG. 23: Special constructs with beta-D-oxy-LNA. The numbers stand for the alternate contiguous stretch of DNA and beta-D-oxy-LNA. In the drawing, the line is DNA, the rectangle is beta-D-oxy-LNA.
Figure 24:
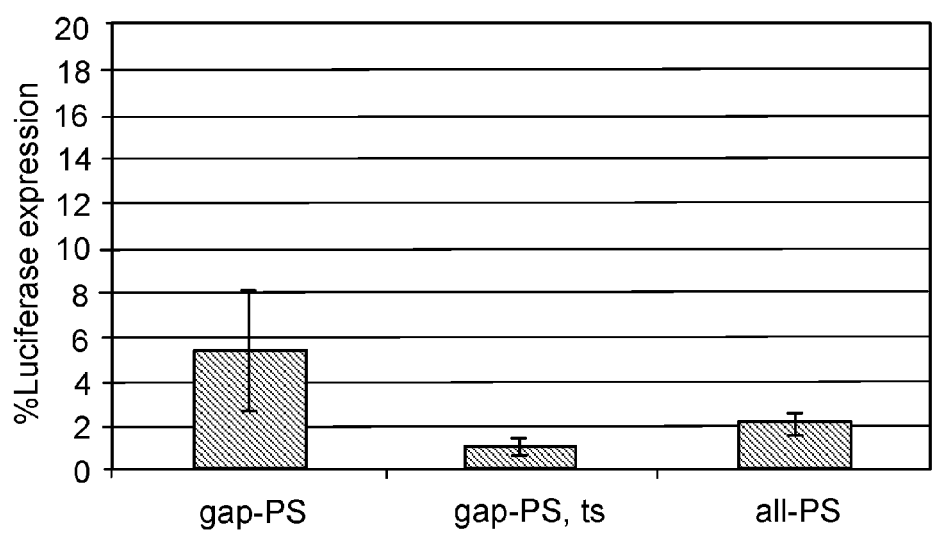
FIG. 24: Down-regulation of Luciferase expression of special constructs containing beta-D-oxy-LNA (designs 3-9-3-1) at 2 nM oligonucleotide concentration.

Design 3-9-3-1 has a deoxynucleoside residue at the 3'-end, see table 11 and FIG. 23. It shows significant levels of down-regulation, in the same range than an optimised (9 nt) fully thiolated gapmer. Moreover, only partial thiolation is needed for these mixmers to work as good as the fully thiolated gapmer, see FIG. 24.

TABLE 11

Special beta-D-oxy-LNA constructs (SEQ ID NOS 31-33, respectively, in order of appearance) (Capital letters for LNA and small letters for DNA). Residue c is methyl-c for LNA.

| ref | | sequence | mixmer |
|---|---|---|---|
| 2023-1; | 02574 | TTCc$_s$g$_s$t$_s$c$_s$a$_s$t$_s$c$_s$g$_s$t$_s$CTTt | 3-9-3-1 |
| 2023-k; | 02575 | TTCc$_s$g$_s$t$_s$c$_s$a$_s$t$_s$c$_s$g$_s$t$_s$CTT$_s$t | 3-9-3-1 |
| 2023-j; | 02576 | T$_s$T$_s$C$_s$c$_s$g$_s$t$_s$c$_s$a$_s$t$_s$c$_s$g$_s$t$_s$C$_s$T$_s$T$_s$t | 3-9-3-1 |

Other oligonucleotides containing novel LNA monomers (beta-D-amino-, beta-D-thio- and alpha-L-LNA) and bearing a deoxynucleoside residue at the 3'-end were tested in different assays, see tables 3, 6, 9 and 10 for more detail.

The invention claimed is:

1. A gapmer oligonucleotide 12 26 nucleotide units in length of formula A-B-C-D, wherein:

A represents a sequence of locked nucleotide units;

B represents a sequence of at least 6 continuous DNA nucleotide units;

C represents a locked nucleotide unit or a sequence of locked nucleotide units;

D represents a non-locked nucleotide unit or a sequence of non-locked nucleotide units, wherein the non-locked nucleotide unit of region D is a 2' substituted non-locked nucleotide, wherein the 2' substituent is selected from the group consisting of halogen or $C_1$-$C_9$ alkoxy.

2. The gapmer oligonucleotide according to claim 1, wherein at least one of the locked nucleotide units of regions A and/or C is a nucleotide of formula:

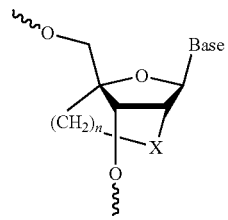

wherein X is O; one of the H's in $(CH_2)n$ is replaced with a $C_{1-6}$ alkyl substituent; n is 1; and Base is independently selected from the group consisting of cytosine, methyl cytosine, uracil, thymine, adenine and guanine.

3. The gapmer oligonucleotide according to claim 2, wherein one of the H's in $(CH_2)n$ is replaced with methyl.

4. The gapmer oligonucleotide according to claim 1 wherein at least one of the internucleoside linkages is a phosphorothioate linkage.

5. The gapmer oligonucleotide of claim 1 wherein all of the internucleotide linkages are phosphorothioate linkages.

6. The gapmer oligonucleotide according to claim 2 wherein at least one of the internucleotide linkages is a phosphorothioate linkages.

7. The gapmer oligonucleotide according to claim 2 wherein all of the internucleotide linkages are phosphorothioate linkages.

8. The gapmer oligonucleotide of claim 1 wherein in the central region B is 8-12 DNA nucleotides.

9. The gapmer oligonucleotide of claim 2 wherein in the central region B is 8-12 DNA nucleotides.

10. The gapmer oligonucleotide of claim 1, wherein region A has a length of 2-6 nucleotide units and region C has a length of 1-5 nucleotide units and region D has a length of 1-3 nucleotide units.

11. The gapmer oligonucleotide of claim 2, wherein region A has a length of 2-6 nucleotide units and region C has a length of 1-5 nucleotide units and region D has a length of 1-3 nucleotide units.

12. The gapmer oligonucleotide of claim 1, wherein region A has a length of 3-5 nucleotide units and region C has a length of 2-4 nucleotide units and region D has a length of 1-2 nucleotide units.

13. The gapmer oligonucleotide of claim 2, wherein region A has a length of 3-5 nucleotide units and region C has a length of 2-4 nucleotide units and region D has a length of 1-2 nucleotide units.

14. The gapmer oligonucleotide of claim 1, wherein the gapmer oligonucleotide has a length of 12-21 nucleotide units.

15. The gapmer oligonucleotide of claim 2, wherein the gapmer oligonucleotide has a length of 12-21 nucleotide units.

16. The gapmer oligonucleotide of claim 1, wherein the gapmer oligonucleotide has a length of 15-17 nucleotide units.

17. The gapmer oligonucleotide of claim 2, wherein the gapmer oligonucleotide has a length of 15-17 nucleotide units.

18. The gapmer oligonucleotide of claim 1, wherein the gapmer oligonucleotide has a length of 13, 14, 15, 16, 17 or 18 nucleotide units.

19. The gapmer oligonucleotide of claim 2, wherein the gapmer oligonucleotide has a length of 13, 14, 15, 16, 17 or 18 nucleotide units in length.

* * * * *